United States Patent
Carlos et al.

(10) Patent No.: US 10,981,871 B2
(45) Date of Patent: *Apr. 20, 2021

(54) METHODS FOR PREPARING N-(4-FLUOROBENZYL)-N-(1-METHYLPIPERIDIN-4-YL)-N'-(4-(2-METHYLPROPYLOXY)PHENYLMETHYL)CARBAMIDE AND ITS TARTRATE SALT AND POLYMORPHIC FORM C

(71) Applicant: ACADIA Pharmaceuticals Inc., San Diego, CA (US)

(72) Inventors: Marlon Carlos, Chula Vista, CA (US); Sagun Tandel, San Diego, CA (US); Roger Olsson, Bunkeflostrand (SE); Mikael Hillgren, Orebro (SE); Matthew J. Fleming, Zofingen (CH); Andreas Philipp Boudier, Zurich (CH); Beat T. Weber, Zofingen (CH)

(73) Assignee: ACADIA Pharmaceuticals Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/786,809

(22) Filed: Feb. 10, 2020

(65) Prior Publication Data
US 2020/0181087 A1    Jun. 11, 2020

Related U.S. Application Data

(63) Continuation of application No. 15/744,636, filed as application No. PCT/US2016/042933 on Jul. 19, 2016, now Pat. No. 10,597,363.

(60) Provisional application No. 62/194,725, filed on Jul. 20, 2015.

(51) Int. Cl.
C07D 211/58    (2006.01)

(52) U.S. Cl.
CPC .................. C07D 211/58 (2013.01)

(58) Field of Classification Search
CPC .................................................. C07D 211/58
USPC ........................................................ 546/224
See application file for complete search history.

(56) References Cited

U.S. PATENT DOCUMENTS

| | | |
|---|---|---|
| 3,983,234 A | 9/1976 | Sayers |
| 4,138,492 A | 2/1979 | Noverola et al. |
| 4,255,432 A | 3/1981 | Kluge et al. |
| 4,332,804 A | 6/1982 | Clark |
| 4,353,900 A | 10/1982 | Clark |
| 4,353,901 A | 10/1982 | Clark |
| 4,367,232 A | 1/1983 | Boix-Igleasias et al. |
| 4,853,394 A | 8/1989 | King |
| 5,025,013 A | 6/1991 | Barreau |
| 5,214,055 A | 5/1993 | Peglion et al. |
| 5,216,165 A | 6/1993 | Mobilio et al. |
| 5,461,066 A | 10/1995 | Gericke et al. |
| 5,595,872 A | 1/1997 | Wetterau, II et al. |
| 5,621,010 A | 4/1997 | Sueda |
| 5,707,798 A | 1/1998 | Brann |
| 5,795,894 A | 8/1998 | Shue |

(Continued)

FOREIGN PATENT DOCUMENTS

| | | |
|---|---|---|
| CA | 984843 A | 3/1976 |
| CN | 104844502 A | 8/2015 |

(Continued)

OTHER PUBLICATIONS

U.S. Appl. No. 09/800,096, Azacyclic compounds, filed Mar. 6, 2001, Issued, U.S. Pat. No. 6,815,458.
U.S. Appl. No. 10/409,782, Azacyclic compounds, filed Apr. 7, 2003, Issued, U.S. Pat. No. 6,756,393.
U.S. Appl. No. 13/053,079, Methods of treatment using selective 5-HT2A inverse agonists, filed Mar. 21, 2011, Issued, U.S. Pat. No. 9,765,053.
U.S. Appl. No. 14/628,156, Azacyclic compounds, filed Feb. 20, 2015, Issued, U.S. Pat. No. 9,296,694.
U.S. Appl. No. 10/759,561, Selective serotonin 2A/2C receptor inverse agonists as therapeutics for neurodegenerative diseases, filed Jan. 15, 2004, Issued, U.S. Pat. No. 7,601,740.

(Continued)

*Primary Examiner* — Nizal S Chandrakumar
(74) *Attorney, Agent, or Firm* — Goodwin Procter LLP

(57) ABSTRACT

Disclosed herein are methods for obtaining N-(4-fluorobenzyl)-N-(1-methylpiperidin-4-yl)-N'-(4-(2-methylpropyloxy)phenylmethyl) carbamide (pimavanserin) comprising the step of contacting an intermediate according to Formula (A) or a salt thereof, with an intermediate Formula B, or a salt thereof, to produce pimavanserin or a salt thereof wherein Y is —$OR_i$ or —$NR_{2a}R_{2b}$; $R_3$ is hydrogen or substituted or unsubstituted heteroalicyclyl, $R_4$ is substituted or unsubstituted aralkyl; X is —$OR_{22}$ or —$NR_{23}R_{24}$; (wherein $R_{22}$ is hydrogen or substituted or unsubstituted $C_{1-6}$alkyl and one of $R_{23}$ and $R_{24}$ is hydrogen and the other is hydrogen or N-methylpiperidin-4-yl); and $R_{21}$ is —$OCH_2CH(CH_3)_2$ or F; Also disclosed herein is the tartrate salt of N-(4-fluorobenzyl)-N-(1-methylpiperidin-4-yl)-N'-(4-(2-methylpropyloxy)phenylmethyl) carbamide and methods for obtaining the salt.

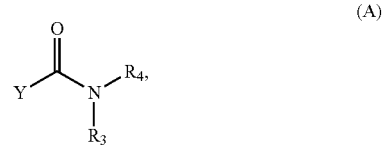

(A)

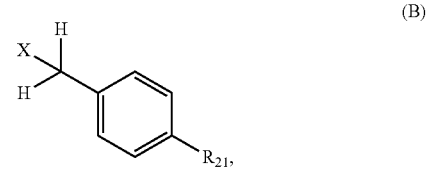

(B)

13 Claims, No Drawings

(56) References Cited

U.S. PATENT DOCUMENTS

| | | | |
|---|---|---|---|
| 5,837,730 A | 11/1998 | Javitt | |
| 5,869,488 A | 2/1999 | Shue | |
| 5,877,173 A | 3/1999 | Olney | |
| 5,912,132 A | 6/1999 | Brann | |
| 5,955,281 A | 9/1999 | Brann | |
| 6,107,324 A | 8/2000 | Behan | |
| 6,140,509 A | 10/2000 | Behan | |
| 6,150,393 A | 11/2000 | Behan | |
| 6,358,698 B1 | 3/2002 | Weiner et al. | |
| 6,451,343 B1 | 9/2002 | Glinecke et al. | |
| 6,479,480 B1 | 11/2002 | Moyes | |
| 6,486,153 B1 | 11/2002 | Castro Pineiro | |
| 6,670,137 B2 | 12/2003 | VanMechelen et al. | |
| 6,756,393 B2 | 6/2004 | Andersson et al. | |
| 6,815,458 B2 | 11/2004 | Andersson et al. | |
| 6,911,452 B2 | 6/2005 | Schlienger | |
| 7,022,698 B2 | 4/2006 | Hamied et al. | |
| 7,041,667 B1 | 5/2006 | Armour et al. | |
| 7,087,593 B2 | 8/2006 | Kelly et al. | |
| 7,115,634 B2 | 10/2006 | Thurieau et al. | |
| 7,217,719 B2 | 5/2007 | Schlienger | |
| 7,253,186 B2 | 8/2007 | Andersson et al. | |
| 7,351,707 B2 | 4/2008 | Schlienger | |
| 7,393,861 B2 | 7/2008 | Thurieau et al. | |
| 7,476,682 B2 | 1/2009 | Andersson et al. | |
| 7,538,222 B2 | 5/2009 | Andersson et al. | |
| 7,601,740 B2 | 10/2009 | Weiner et al. | |
| 7,659,285 B2 | 2/2010 | Weiner et al. | |
| 7,713,995 B2 | 5/2010 | Weiner et al. | |
| 7,732,462 B2 | 6/2010 | Weiner et al. | |
| 7,732,615 B2 | 6/2010 | Thygesen et al. | |
| 7,790,899 B2 | 9/2010 | Tolf et al. | |
| 7,816,383 B1 | 10/2010 | Bradford et al. | |
| 7,820,695 B2 | 10/2010 | Weiner et al. | |
| 7,858,789 B2 | 12/2010 | Thurieau et al. | |
| 7,863,296 B2 | 1/2011 | Weiner et al. | |
| 7,868,176 B2 | 1/2011 | Thygesen et al. | |
| 7,875,632 B2 | 1/2011 | Weiner et al. | |
| 7,923,564 B2 | 4/2011 | Thygesen et al. | |
| 7,994,193 B2 | 8/2011 | Weiner et al. | |
| 8,008,323 B2 | 8/2011 | Weiner et al. | |
| 8,110,574 B2 | 2/2012 | Thurieau et al. | |
| 8,227,487 B2 | 7/2012 | Weiner et al. | |
| 8,236,960 B2 | 8/2012 | Thygesen et al. | |
| 8,377,959 B2 | 2/2013 | Weiner et al. | |
| 8,618,130 B2 | 12/2013 | Weiner et al. | |
| 8,921,393 B2 | 12/2014 | Weiner et al. | |
| 9,050,343 B2 | 6/2015 | Peters et al. | |
| 9,211,289 B2 | 12/2015 | Weiner et al. | |
| 9,296,694 B2 | 3/2016 | Andersson et al. | |
| 9,446,037 B2 | 9/2016 | Mills et al. | |
| 9,486,453 B2 | 11/2016 | Javitt | |
| 9,566,271 B2 | 2/2017 | Weiner et al. | |
| 9,757,366 B2 | 9/2017 | Mills et al. | |
| 9,765,053 B2 | 9/2017 | Andersson et al. | |
| 10,028,944 B2 | 7/2018 | Weiner et al. | |
| 10,449,185 B2 | 10/2019 | Tejwani et al. | |
| 10,517,860 B2 | 12/2019 | Parkinson | |
| 10,525,046 B2 | 1/2020 | Weiner et al. | |
| 10,597,363 B2 | 3/2020 | Carlos et al. | |
| 10,646,480 B2 | 5/2020 | Tejwani et al. | |
| 10,849,891 B2 | 12/2020 | Tejwani et al. | |
| 2002/0156068 A1 | 10/2002 | Behan | |
| 2002/0165225 A1 | 11/2002 | Kankan et al. | |
| 2004/0006081 A1 | 1/2004 | Burrows | |
| 2004/0106600 A1 | 6/2004 | Andersson et al. | |
| 2004/0213816 A1 | 10/2004 | Weiner et al. | |
| 2004/0229908 A1 | 11/2004 | Nelson | |
| 2005/0014757 A1 | 1/2005 | Andersson et al. | |
| 2005/0148018 A1 | 7/2005 | Weiner et al. | |
| 2005/0244862 A1 | 11/2005 | Brann | |
| 2005/0256108 A1 | 11/2005 | Schlienger | |
| 2005/0261278 A1 | 11/2005 | Weiner et al. | |
| 2005/0261340 A1 | 11/2005 | Weiner et al. | |
| 2005/0288328 A1 | 12/2005 | Weiner et al. | |
| 2006/0094758 A1 | 5/2006 | Andersson et al. | |
| 2006/0106063 A1 | 5/2006 | Thhygesen et al. | |
| 2006/0111399 A1 | 5/2006 | Thhygesen et al. | |
| 2006/0194778 A1 | 8/2006 | Andersson et al. | |
| 2006/0194834 A1 | 8/2006 | Andersson et al. | |
| 2006/0199794 A1 | 9/2006 | Schlienger | |
| 2006/0199818 A1 | 9/2006 | Andersson et al. | |
| 2006/0199842 A1 | 9/2006 | Weiner et al. | |
| 2006/0204486 A1 | 9/2006 | Pyke et al. | |
| 2006/0205710 A1 | 9/2006 | Schlienger | |
| 2006/0205722 A1 | 9/2006 | Andersson et al. | |
| 2006/0205780 A1 | 9/2006 | Thygesen et al. | |
| 2006/0205781 A1 | 9/2006 | Thygesen et al. | |
| 2006/0264465 A1 | 11/2006 | Weiner et al. | |
| 2006/0264466 A1 | 11/2006 | Weiner et al. | |
| 2006/0286610 A1 | 12/2006 | Brann | |
| 2006/0292606 A1 | 12/2006 | Brann | |
| 2007/0260064 A1 | 11/2007 | Tolf et al. | |
| 2007/0264330 A1 | 11/2007 | Ragnar-Tolf | |
| 2008/0051429 A1 | 2/2008 | Van Kammen et al. | |
| 2008/0280886 A1 | 11/2008 | Gant et al. | |
| 2009/0053329 A1 | 2/2009 | Peters et al. | |
| 2009/0082342 A1 | 3/2009 | Uldam et al. | |
| 2009/0082388 A1 | 3/2009 | Hacksell | |
| 2009/0186921 A1 | 7/2009 | Andersson et al. | |
| 2014/0018348 A1 | 1/2014 | Javitt | |
| 2014/0162942 A1 | 6/2014 | Ghosal et al. | |
| 2014/0221395 A1 | 8/2014 | Dhanoa | |
| 2014/0329903 A1 | 11/2014 | Burstein et al. | |
| 2014/0349976 A1 | 11/2014 | Hacksell et al. | |
| 2015/0231126 A1 | 8/2015 | Peters | |
| 2015/0313888 A1 | 11/2015 | Mills et al. | |
| 2016/0237036 A1 | 8/2016 | Andersson et al. | |
| 2018/0037549 A1* | 2/2018 | Biljan | C07C 259/06 |
| 2019/0030015 A1 | 1/2019 | Weiner et al. | |
| 2019/0047955 A1 | 2/2019 | Carlos et al. | |
| 2019/0117636 A1 | 4/2019 | Burstein | |
| 2019/0216791 A1 | 7/2019 | Tejwani et al. | |
| 2019/0231767 A1 | 8/2019 | Parkinson | |
| 2019/0240211 A1 | 8/2019 | Parkinson | |
| 2020/0009122 A1 | 1/2020 | Tejwani et al. | |
| 2020/0061045 A1 | 2/2020 | Burstein | |
| 2020/0078346 A1 | 3/2020 | Parkinson | |
| 2020/0165202 A1 | 5/2020 | Carlos et al. | |
| 2020/0222381 A1 | 7/2020 | Tejwani et al. | |
| 2020/0237739 A1 | 7/2020 | Coate et al. | |
| 2020/0323836 A1 | 10/2020 | Weiner et al. | |

FOREIGN PATENT DOCUMENTS

| | | |
|---|---|---|
| CN | 104961672 A | 10/2015 |
| CN | 105111135 A | 12/2015 |
| CN | 105153016 A | 12/2015 |
| CN | 105418460 A | 3/2016 |
| CN | 105481757 A | 4/2016 |
| CN | 105820110 A | 8/2016 |
| CN | 106543072 A | 3/2017 |
| EP | 0005318 B1 | 11/1979 |
| EP | 0061333 B1 | 9/1982 |
| EP | 0260070 B1 | 3/1988 |
| EP | 0379441 A1 | 7/1990 |
| EP | 0548015 B1 | 6/1993 |
| EP | 0625507 B1 | 11/1994 |
| EP | 1576985 A1 | 9/2005 |
| HU | 157325 | 3/1998 |
| JP | 51052176 | 5/1976 |
| JP | 52085174 A | 7/1977 |
| WO | WO-94/27967 A1 | 12/1994 |
| WO | WO-97/08166 A1 | 3/1997 |
| WO | WO-97/11940 A1 | 4/1997 |
| WO | WO-97/38665 A2 | 10/1997 |
| WO | WO-97/38984 A1 | 10/1997 |
| WO | WO-98/11128 A1 | 3/1998 |
| WO | WO-9817646 A1 | 4/1998 |
| WO | WO-98/44921 A1 | 10/1998 |
| WO | WO-98/50534 A1 | 11/1998 |
| WO | WO-99/52927 A1 | 10/1999 |
| WO | WO-0023076 A1 | 4/2000 |
| WO | WO-0056335 A1 | 9/2000 |

(56) References Cited

FOREIGN PATENT DOCUMENTS

| WO | WO-0059497 A1 | 10/2000 |
|----|----|----|
| WO | WO-0069810 A1 | 11/2000 |
| WO | WO-0144191 A1 | 6/2001 |
| WO | WO-0166521 A1 | 9/2001 |
| WO | WO-0187839 A1 | 11/2001 |
| WO | WO-2001089498 A2 | 11/2001 |
| WO | WO-0224649 A1 | 3/2002 |
| WO | WO-2002038142 A2 | 5/2002 |
| WO | WO-0207646 A1 | 10/2002 |
| WO | WO-02079186 A2 | 10/2002 |
| WO | WO-03057698 A2 | 7/2003 |
| WO | WO-03062206 A2 | 7/2003 |
| WO | WO-03070246 A1 | 8/2003 |
| WO | WO-03086400 A1 | 10/2003 |
| WO | WO-04000808 A2 | 12/2003 |
| WO | WO-04039322 A2 | 5/2004 |
| WO | WO-04064753 A2 | 8/2004 |
| WO | WO-2004064738 A2 | 8/2004 |
| WO | WO-05053796 A1 | 6/2005 |
| WO | WO-05063254 A2 | 7/2005 |
| WO | WO-05112927 A1 | 12/2005 |
| WO | WO-06036874 A1 | 4/2006 |
| WO | WO 2006037043 A1 | 4/2006 |
| WO | WO-06104826 A2 | 10/2006 |
| WO | WO-2007124136 A1 | 11/2007 |
| WO | WO-2007133802 A2 | 11/2007 |
| WO | WO-2008116024 A2 | 9/2008 |
| WO | WO-2008141057 A1 | 11/2008 |
| WO | WO-2008144326 A2 | 11/2008 |
| WO | WO-2008144665 A1 | 11/2008 |
| WO | WO-2009035473 A2 | 3/2009 |
| WO | WO-2009039460 A2 | 3/2009 |
| WO | WO-2009039461 A2 | 3/2009 |
| WO | WO-2010111353 A1 | 9/2010 |
| WO | WO-2011047341 A2 | 4/2011 |
| WO | WO-2011085216 A2 | 7/2011 |
| WO | WO-2014085362 A1 | 6/2014 |
| WO | WO-2016201373 A1 | 12/2016 |
| WO | WO-2017011767 A2 | 1/2017 |
| WO | WO-2017015272 A1 | 1/2017 |
| WO | WO-2017165635 A1 | 9/2017 |
| WO | WO-2017/172757 A1 | 10/2017 |
| WO | WO-2018/118626 A1 | 6/2018 |
| WO | WO-2018/200977 A1 | 11/2018 |
| WO | WO-2019/046167 A1 | 3/2019 |
| WO | WO-2019177973 A1 | 9/2019 |
| WO | WO-2020092618 A1 | 5/2020 |

OTHER PUBLICATIONS

U.S. Appl. No. 11/416,527, Selective Serotonin 2A/2C Receptor Inverse Agonists As Therapeutics for Neurodegenerative Diseases, filed May 3, 2006, Issued, U.S. Pat. No. 7,732,462.
U.S. Appl. No. 11/416,855, Selective serotonin 2A/2C receptor inverse agonists as therapeutics for neurodegenerative diseases, filed May 3, 2006, Issued, U.S. Pat. No. 7,659,285.
U.S. Appl. No. 11/416,594, Selective serotonin 2A/2C receptor inverse agonists as therapeutics for neurodegenerative diseases, filed May 3, 2006, Issued, U.S. Pat. No. 7,713,995.
U.S. Appl. No. 12/759,662, Selective serotonin 2A/2C receptor inverse agonists as therapeutics for neurodegenerative diseases, filed Apr. 13, 2010, Issued, U.S. Pat. No. 7,994,193.
U.S. Appl. No. 12/759,664, Selective serotonin 2A/2C receptor inverse agonists as therapeutics for neurodegenerative diseases, filed Apr. 13, 2010, Issued, U.S. Pat. No. 8,008,323.
U.S. Appl. No. 13/169,893, Selective serotonin 2A/2C receptor inverse agonists as therapeutics for neurodegenerative diseases, filed Jun. 27, 2011, Issued, U.S. Pat. No. 8,227,487.
U.S. Appl. No. 13/539,011, Selective serotonin 2A/2C receptor inverse agonists as therapeutics for neurodegenerative diseases, filed Jun. 29, 2012, Issued, U.S. Pat. No. 8,377,959.
U.S. Appl. No. 13/750,778, Selective serotonin 2A/2C receptor inverse agonists as therapeutics for neurodegenerative diseases, filed Jan. 25, 2013, Issued, U.S. Pat. No. 8,618,130.
U.S. Appl. No. 14/086,838, Selective serotonin 2A/2C receptor inverse agonists as therapeutics for neurodegenerative diseases, filed Nov. 21, 2013, Issued, U.S. Pat. No. 8,921,393.
U.S. Appl. No. 14/537,793, Selective serotonin 2A/2C receptor inverse agonists as therapeutics for neurodegenerative diseases, filed Nov. 10, 2014, Issued, U.S. Pat. No. 9,211,289.
U.S. Appl. No. 14/935,246, Selective serotonin 2A/2C receptor inverse agonists as therapeutics for neurodegenerative diseases, filed Nov. 6, 2015, Issued, U.S. Pat. No. 9,566,271.
U.S. Appl. No. 15/397,582, Selective serotonin 2A/2C receptor inverse agonists as therapeutics for neurodegenerative diseases, filed Jan. 3, 2017, Issued, U.S. Pat. No. 10,028,944.
U.S. Appl. No. 16/019,485, Selective serotonin 2A/2C receptor inverse agonists as therapeutics for neurodegenerative diseases, filed Jun. 26, 2018, Issued, U.S. Pat. No. 10,525,046.
U.S. Appl. No. 16/687,467, Selective serotonin 2A/2C receptor inverse agonists as therapeutics for neurodegenerative diseases, filed Nov. 18, 2019, Pending, N/A.
U.S. Appl. No. 10/850,819, Selective serotonin receptor inverse agonists as therapeutics for disease, filed May 21, 2004, Issued, U.S. Pat. No. 7,820,695.
U.S. Appl. No. 11/134,769, Selective scrotonin receptor inverse agonists as therapeutics for disease, filed May 20, 2005, Issued, U.S. Pat. No. 7,863,296.
U.S. Appl. No. 12/378,385, Selective serotonin receptor inverse agonists as therapeutics for disease, filed Feb. 11, 2009, Issued, U.S. Pat. No. 7,875,632.
U.S. Appl. No. 11/235,558, N-(4-fluorobenzyl)-N-(1-methylpiperidin-4-yl)-N'-(4-(2-methylpropyloxy)phenylmethyl)carbamide and its tartrate salt and crystalline forms, filed Sep. 26, 2005, Issued, U.S. Pat. No. 7,732,615.
U.S. Appl. No. 11/235,381, Salts of N-(4-fluorobenzyl)-N-(1-methylpiperidin-4-yl-N'-(4-(2-methylpropyloxy)phenylmethyl)carbamide and their preparation, filed Sep. 26, 2005, Issued, U.S. Pat. No. 7,868,176.
U.S. Appl. No. 12/795,547, Synthesis of N-(4-fluorobenzyl)-N-(1-methylpiperidin-4-yl)-N'-(4-(2-methylpropyloxy)phenylmethyl)earbamide and its tartrate salt and crystalline forms, filed Jun. 7, 2010, Issued, U.S. Pat. No. 7,923,564.
U.S. Appl. No. 13/081,427, Synthesis of N-(4-fluorobenzyl)-N-(1-methylpiperidin-4-yl)-N'-(4-(2-methylpropyloxy)phenylmethyl)carbamide and its tartrate salt and crystalline forms, filed Apr. 6, 2011, Issued, U.S. Pat. No. 8,236,960.
U.S. Appl. No. 11/749,115, Synthesis of N-(4-fluorobenzyl)-N-(1-methylpiperidin-4-yl)-N'-(4-(2-methylpropyloxy)phenylmethyl)carbamide and its tartrate salt and crystalline forms, filed May 15, 2007, Issued, U.S. Pat. No. 7,790,899.
U.S. Appl. No. 13/754,769, Combination of pimavanscrin and risperidone for the treatment of psychosis, filed Jan. 30, 2013, Issued, U.S. Pat. No. 9,050,343.
U.S. Appl. No. 14/647,438, Methods for the treatment of Parkinson's disease psychosis using pimavanserin, filed May 26, 2015, Issued, 9,446,037.
U.S. Appl. No. 15/246,412, Methods for the treatment of Parkinson's disease psychosis using pimavanserin, filed Aug. 24, 2016, Issued, U.S. Pat. No. 9,757,366.
U.S. Appl. No. 15/744,636, Methods for preparing N-(4-fluorobenzyl)-N-(1-methylpiperidin-4-yl)-N'-(4-(2-methylpropyloxy)phenylmethyl)carbamide and its tartrate salt and polymorphic form, filed Jan. 12, 2018, Issued, U.S. Pat. No. 10,597,363.
U.S. Appl. No. 16/743,607, Methods for preparing N-(4-fluorobenzyl)-N-(1-methylpiperidin-4-yl)-N'-(4-(2-methylpropyloxy)phenylmethyl)carbamide and its tartrate salt and polymorphic form, filed Jan. 15, 2020, Pending, N/A.
U.S. Appl. No. 16/089,316, 5-HT2A serotonin receptor inverse agonists or antagonists for use in reducing amyloid-beta peptides and accumulation of amyloid plaques, filed Sep. 27, 2018, Pending, 20190117636.

(56) References Cited

OTHER PUBLICATIONS

U.S. Appl. No. 16/087,604, Combination of pimavanserin and cytochrome p450 modulators, filed Sep. 21, 2018, Pending, 20190240211.
U.S. Appl. No. 16/379,169, Combination of pimavanserin and cytochrome p450 modulators, filed Apr. 9, 2019, Issued, U.S. Pat. No. 10,517,860.
U.S. Appl. No. 16/684,883, Combination of pimavanscrin and cytochrome p450 modulators, filed Nov. 15, 2019, Pending, 20200078346.
U.S. Appl. No. 16/607,234, Pimavanserin for Treating Impulse Control Disorder, filed Oct. 22, 2019, Pending, 20200061045.
U.S. Appl. No. 16/471,543, Methods for the Treatment of Alzheimer's Disease Psychosis Using Pimavanserin, filed Jun. 19, 2019, Pending, N/A.
U.S. Appl. No. 16/363,378, Formulations of Pimavanserin, filed Mar. 25, 2019, Issued, U.S. Pat. No. 10,449,185.
U.S. Appl. No. 16/571,554, Formulations of Pimavanserin, filed Sep. 16, 2019, Issued, U.S. Pat. No. 10,646,480.
U.S. Appl. No. 16/836,086, Formulations of Pimavanserin, filed Mar. 31, 2020, Pending, N/A.
"ACP-103," *Drugs of the Future, Prous Science* (2006) vol. 31, No. 11, pp. 939-943.
"NUPLAZID™ (pimavanserin) Sponsor Background Information for a Meeting of the Psychopharmacologic Drugs Advisory Committee on Mar. 29, 2016," Acadia Pharmaceuticals Inc., 2016. Retrieved from the Internet (URL): <https://www.fda.gov/downloads/advisorycommittees/committeesmeetingmaterials/drugs/psychopharmacologicdrugsadvisorycommittee/ucm492453.pdf> (173 pages).
"Pimavanserin (Nuplazid) for parkinson's disease psychosis," Medical Letter on Drugs and Therapeutics, New Rochelle, NY, US (Jun. 2016) vol. 58, pp. 74-75.
Aarsland et al., "Decreased burden among caregivers of patients with Parkinson's disease psychosis (PDP) treated with pimavanserin, a selective 5-HT2A inverse agonist," (Meeting Abstract) *Neurology* (2015) vol. 84, No. 14, Suppl P6.044.
Abbas et al., "Pimavanserin tartrate: a 5-HT2A inverse agonist with potential for treating various neuropsychiatric disorders," *Expert Opinion on Pharmacotherapy* (2008) vol. 9, No. 18, pp. 3251-3259.
Adam, et al., "Effects of repeated ritanserin on middle-aged poor sleepers," *Psychopharmacology* (1989) 99:219-221.
Akin, et al., "Decreased serotonin 5-HT 2A receptor-stimulated phosphoinositide signaling in fibroblasts from melancholic depressed patients," *Neuropsychopharmacology* (2004) 29:2081-2087.
Antunes, et al., "The novel object recognition memory: neurobiology, test procedure, and its modifications," *Cogn. Process* (2012) 13:93-110.
Bakshi, et al., "Clozapine antagonizes phencyclidine-induced deficits in sensorimotor gating of the startle response," *The Journal of Pharmacology and Experimental Therapeutics* (1994) 271(2):787-794.
Bennett, et al., "Suppression of dyskinesias in advanced Parkinson's disease. II. Increasing daily clozapine doses suppress dyskinesias and improve parkinsonism symptoms," *Neurology* (1993) 43:1551-1554.
Biagi, et al., "1,2,3-Triazoles: Structural changes on two effective inhibitors of the prostaglandin synthesis in vitro," *Farmaco Ed. Sci.* (1988) 43:597-611.
Bibbiani, et al., "Serotonin 5-HT1A agonist improves motor complications in rodent and primate parkinsonian models," *Neurology* (2001) 57:1829-1834.
Blakley, et al., "Bidirectional changes in ethanol consumption in rats with site-specific antisense down-regulation of 5-hydroxytryptamine2A receptors in brain," *The Journal of Pharmacology and Experimental Therapeutics* (2001) 299(1):277-289.
Blier, et al., "Potential mechanisms of action of atypical antipsychotic medications in treatment-resistant depression and anxiety," *J. Clin. Psychiatry* (2005) 66(suppl 8):30-40.

Blier, et al., "Putative mechanisms of action of antidepressant drugs in affective and anxiety disorders and pain," *Journal of Psychiatry & Neuroscience* (2001) 26(1):37-43.
Bond et al., "Physiological effects of inverse agonists in transgenic mice with myocardial overexpression of the beta-adrenoceptor," *Nature* (1995) 374:272-276.
Borman et al., "5-HT2B receptors play a key role in mediating the excitatory effects of 5-HT in human colon in vitro," *Br. J. Pharmacol.* (2002) vol. 135, No. 5, pp. 1144-1151.
Brann, M. R. "Identification of ligands by selective amplification of cells transfected with receptors and marker enzymes," *Chemical Abstracts* (1998) 128: 111548.
Chaturvedi, D., "Perspectives on the Synthesis of Organic Carbamates," Tetrahedron 68:15-45 (2012).
Chaturvedi, D., "Recent Developments on the Carbamation of Amines," Curr. Org. Chem. 15:1593-1624 (2011).
Choi et al., "5HT2B receptor-mediated serotonin morphogenic functions in mouse cranial neural crest and myocardiac cells," *Development* (1997) vol. 124, pp. 1745-1755.
Cirrito et al., "Serotonin signaling is associated with lower amyloid-p levels and plaques in transgenic mice and humans," *PNAS* (2011) vol. 108, No. 36, pp. 14968-14973.
Cummings et al., "Pimavanserin for patients with Parkinson's disease psychosis: a randomised, placebo-controlled phase 3 trial," *Lancet* (2014) vol. 383, pp. 533-540.
DeClerck, et al., "Increase in slow-wave sleep in humans with the serotonin-S2 antagonist ritanserin," *Current Therapeutic Research* (1987) 41(4):427-432.
Delecluse, et al., "A case of tardive tremor successfully treated with clozapine," *Movement Disorders* (1998) 13(5):846-847.
Dine et al., "One-Pot, Solvent-Free Access to Unsymmetrical Ureas by Palladium-Catalysed Reductive Alkylation Using Molecular Hydrogen," Eur. J. Chem., 5445-5454 (2013).
Dube et al., "Carbonyldiimidazole-Mediated Lossen Rearrangement." Org. Lett. 11(24):5622-5625 (2009).
Dunn, et al., "Analgetic and antiinflammatory 7-aroylbenzofuran-5-ylacetic acids and 7-aroylbenzothiophene-5-ylacetic acids," *J. Med. Chem.* (1986) 29:2326-2329.
Durif, et al., "Low-dose clozapine improves dyskinesias in Parkinson's disease," *Neurology* (1997) 48:658-662.
Eichelbaum, et al., "Influence of pharmacogenetics on drug disposition and response," *Clinical and Experimental Pharmacology and Physiology* (1996) 23:983-985.
Everett, et al., "L-Dopa: Effect on concentrations of dopamine, norepinephrine, and serotonin in brains of mice," *Science* (1970) 168:849-850.
Factor, et al. "Clozapine for the treatment of drug-induced psychosis in Parkinson's disease: Results of the 12 week open label extension in the Psyclops trial," *Movement Disorders* (2001) 16(1):135-139.
Factor, et al., "Clozapine prevents recurrence of psychosis in Parkinson's disease," *Movement Disorders* (1992) 7(2):125-131.
Fava, M. et al. "A Phase 2, Randomized, Double-Blind, Placebo-Controlled Study of Adjunctive Pimavanserin in Patients with Major Depressive Disorder and an Inadequate Resonse to Therapy (Clarity)." J Clin Psychiatry. Sep. 24, 2019;80(6) (13 pages).
Fitzgerald et al., "Possible Role of Vavular Serotonin 5-HT2B Receptors in the Cardiopathy Associated with Fenfluramine," *Molecular Pharmacol.* (1999) vol. 57, pp. 75-81.
Friedman et al., "A Multi-Center, Placebo-Controlled, Double-Blind Trial to Examine the Safety and Efficacy of Pimavanserin in the Treatment of Psychosis in Parkinson's Disease," *Neurology* (2010) vol. 74, No. 9, Suppl. 2, pp. A299.
Friedman, et al., "Atypical antipsychotics in the treatment of drug-induced psychosis in Parkinson's disease," *Movement Disorders* (2000) 15(2):201-211.
Friedman, et al., "Low-dose clozapine for the treatment of drug-induced psychosis in Parkinson's disease," N. *Engl. J. Med.* (1999) 340(10):757-763.
Friedman, J. H. "Clozapine treatment of psychosis in patients with tardive dystonia: Report of three cases," *Movement Disorders* (1994) 9(3):321-324.

(56) References Cited

OTHER PUBLICATIONS

Gillman, P. K. "Monoamine oxidase inhibitors, opioid analgesics and serotonin toxicity," *British Journal of Anaesthesia* (2005) 95(4):434-441.
Goldman et al., "Genetic counseling and testing for Alzheimer disease: Joint practice guidelines of the American College of Medical Genetics and the National Society of Genetic Counselors," *Genetics in Medicine* (2011) vol. 13, No. 6, pp. 597-605.
Hatoum, H. T. et al., "The Use of the Occupational Disruptiveness Scale of the Neuropsychiatric Inventory-Nusing Home Version to Measure the Impact of Rivastigmine on the Disruptive Behavior of Nursing Home Residents with Alzheimer's Disease," *Journal of the American Medical Directors Association* (2005) vol. 6, No. 4, pp. 238-245.
Highlights of Prescribing Information Nuplazid™ (pimavanserin), Revised Apr. 2016. Retrieved from the Internet (URL): https://www.accessdata.fda.gov/drugsatfda_docs/label/2016/207318lbl.pdf (14 pages).
Highlights of Prescribing Information Nuplazid® (pimavanserin), Revised Jun. 2018. Retrieved from the Internet (URL): https://www.accessdata.fda.gov/drugsatfda_docs/label/2018/207318s005lbl.pdf (15 pages).
Highlights of Prescribing Information Nuplazid® (pimavanserin), Revised Mar. 2018. Retrieved from the Internet (URL): https://www.accessdata.fda.gov/drugsatfda_docs/label/2018/207318s002s004lbl.pdf (15 pages).
Idzikowski, et al. 1991. A dose response study examining the effects of ritanserin on human slow wave sleep. Br. J. Clin. Pharmac., 31:193-196.Idzikowski, et al., "A dose response study examining the effects of ritanserin on human slow wave sleep,"*Br. J. Clin. Pharmac.* (1991) 31:193-196.
International Search Report and Written Opinion for International Application No. PCT/US2013/071792, dated Jan. 1, 2014 (9 pages).
International Search Report and Written Opinion in corresponding PCT Patent Application No. PCT/US08/057557 dated Oct. 24, 2008 (10 pages).
International Search Report and Written Opinion in corresponding PCT Patent Application No. PCT/US2017/023795 dated May 29, 2017 (11 pages).
International Search Report and Written Opinion in corresponding PCT Patent Application No. PCT/US2017/024526 dated Jul. 5, 2017 (18 pages).
International Search Report and Written Opinion in corresponding PCT Patent Application No. PCT/US2017/066340 dated Mar. 5, 2018 (13 pages).
International Search Report and Written Opinion in corresponding PCT Patent Application No. PCT/US2018/029831 dated Jul. 11, 2018 (10 pages).
International Search Report and Written Opinion in corresponding PCT Patent Application No. PCT/US2018/048096 dated Oct. 30, 2018 (12 pages).
International Search Report and Written Opinion of the International Searching Authority for International Application No. PCT/US2019/021618 dated Jun. 12, 2019 (10 pages).
International Search Report and Written Opinion of the International Searching Authority for International Application No. PCT/US2019/058927 dated Jan. 23, 2020 (16 pages).
Ito et al., "Prediction of Human Drug Clearance from in Vitro and Preclinical Data Using Physiologically Based and Emperical Approaches," Pharm. Res., (2005) vol. 22, No. 1, pp. 103-112.
Kalgutkar, et al., "Selective inhibitors of monoamine oxidase (MAO-A and MAO-B) as probes of its catalytic site and mechanism," *Medicinal Research Reviews* (1995) 15(4)325-388.
Kondo et al., "Novel Ruthenium-Complex Catalyzed Synthesis of Ureas from Formamides and Amines," Organometallics 16:2562-2570 (1997).
Kotachi et al., "Ruthenium catalysed N.N'-Diarylurea Synthesis from N-Aryl Substituted Formamides and Aminoarenes," J. Chem. Soc., Chem. Comm., 7:549-550 (1990).

Leysen, et al. "Serotonergic component of neuroleptic receptors," *Nature* (1978) 272:168-171.
Liechti, et al., "Effects of MDMA (ecstasy) on prepulse inhibition and habituation of startle in humans after pretreatment with Citalopram, Haloperidol, or Ketanserin," *Neuropsychopharmacology* (2001) 24(3):240-252.
Linder, et al. "Pharmacogenetics: A laboratory tool for optimizing therapeutic efficiency," *Clinical Chemistry* (1997) 43(2):254-266.
Loudon et al., "Conversion of Aliphatic Amides into Amines with [I,I-Bis(trifluoroacetoxy)iodo]benzene. 1. Scope of Reaction," J. Org. Chem. 49:4272-4276 (1984).
Marek et al., "The Selective 5-HT2A receptor Antagonist MI00907 Enhances Antidepressant-Like Behavioral Effects of the SSRI Fluoxetine," *Neuropsychopharmacology* (2005) vol. 30, No. 12, pp. 2205-2215.
Marek, et al., "Synergistic action of 5-HT2A antagonists and selective serotonin reuptake inhibitors in neuropsychiatric disorders," *Neuropsychopharmacology* (2003) 28:402-412.
Medical Review(s), Application No. 207318Orig1s000, Center for Drug Evaluation and Research, Submission Date Sep. 1, 2015 [available online Jun. 3, 2016]. Retrieved from the Internet (URL): <https://www.accessdata.fda.gov/drugsatfda_docs/nda/2016/207318Orig1s000MedR.pdf> (173 pages).
Meltzer et al., "Co-therapy with pimavanserin and risperidone 2 mg provides an improved clinical profile," *Schizophrenia Research* (2008) vol. 98, pp. 16.
Meltzer et al., "Pimavanserin, a Serotonin(2A) Receptor Inverse Agonist, for the Treatment of Parkinson's Disease Psychosis," *Neuropsychopharmacology* (2010) vol. 35, No. 4, pp. 881-892.
Meltzer et al., "Serotonin Receptors: Their Key Role in Drugs to Treat Schizophrenia," *Progress in Neuro-Pyschopharmacology & Biol. Psych.* (2003) vol. 27, pp. 1159-1172.
Meltzer, et al., "Plasma clozapine levels and the treatment of L-DOPA-induced psychosis in Parkinson's disease," *Neuropsychopharmacology* (1995) 12(1):39-45.
Meltzer, H. Y. "The role of serotonin in antipsychotic drug action," *Neuropsychopharmacology* (1999) 21(2S): 106S-115S.
Morley et al., "Antibody to Amyloid p Protein Alleviates Imparied Acquisition, Retention, and Memory Processing in SAMP8 Mice," *Neurobiology of Learning and Memory* (2002), 78(1):125-138.
Naritomi et al., "Prediction of human hepatic clearance from in vivo animal experiments and in vitro metabolic studies with liver microsomes from animals and humans," *Drug Metab. Dispos.* (2001) vol. 29, No. 10, pp. 1316-1324.
NDA Approval/Supplement Approval, NDA 210793 NDA 207318/S-003, Letter Signed Jun. 28, 2018. Retrieved from the Internet (URL): https://www.accessdata.fda.gov/drugsatfda_docs/appletter/2018/210793Orig1s000,207318Orig1s003ltr.pdf (5 pages).
Nebigil et al., "Serotonin is a novel survival factor of cardiomyocytes: mitochondria as a target of 5-HT2B-receptor signaling," *FASEB J.* (2003) vol. 27, No. 10, pp. 1373-1375.
Ng, et al., "L-dopa-induced release of cerebral monoamines," *Science* (1970) 170:76-77.
Nordstrom, et al., "High 5-HT2 receptor occupancy in clozapine treated patients demonstrated by PET," *Psychopharmacology* (1993) 110:365-367.
Norton et al., "Caregivers of PDP patients have an increased risk of developing emotional and social distress that is decreased when PDP is treated with pimavanserin," (Meeting Abstract) *Journal of Parkinson's Disease* (Sep. 2016) vol. 6, No. S1, pp. 257, Abstract No. P42.11.
Norton et al., "Decreased burden among caregivers of patients with Parkinson's disease psychosis (PDP) treated with pimavanserin, a selective 5-HT2A inverse agonist," (Meeting Abstract) *Journal of Parkinson's Disease* (Sep. 2016) vol. 6, No. S1, p. 88, Abstract No. P12.08.
Obach et al., "The Prediction of Human Pharmacolinetic Parameters from Preclinical and in Vitro Metabolism Data," *J. Pharm. Exp. Therap.* (1997) vol. 283, No. 1, pp. 46-58.
Ogawa, et al., "Effects of R-102444 and its active metabolite R-96544, selective 5-HT2A receptor antagonists, on experimental acute and chronic pancreatitis: Additional evidence for possible

(56) References Cited

OTHER PUBLICATIONS involvement of 5-HT2A receptors in the development of experimental pancreatitis," *European Journal of Pharmacology* (2005) 521:156-163.

Paiva, et al., "Effects of ritanserin on sleep disturbances of dysthymic patients," *Psychopharmacology* (1988) 96:395-399.

Patel, et al., "The highly selective 5-hydroxytryptamine (5-HT)2A receptor antagonist, EMO 281014, significantly increases swimming and decreases immobility in male congenital learned helpless rats in the forced swim test," *Synapse* (2004) 52:73-75.

Pierce, et al., "5-hydroxytryptamine-induced synovial plasma extravasation is mediated via 5-hydroxytryptamine2A receptors on sympathetic efferent terminals," *The Journal of Pharmacology and Experimental Therapeutics* (1995) 275(1):502-508.

Poewe, W. "Psychosis in Parkinson's disease," *Movement Disorders* (2006) vol. 18, Suppl. 6, pp. S80-S87.

Pollak, et al., "Clozapine in drug-induced psychosis in Parkinson's disease," *Lancet* (1999) 353:2041-2042.

Price et al., "Pimavanserin, a 5-HT2A receptor inverse agonist, reverses psychosis-like behaviors in a rodent model of Alzheimer's disease," *Behavioural Pharmacology* (2002), 23:426-433.

R&D Focus Drug News (Jan. 24, 2000). Pimvaserin Acadia lead compounds identified.

R&D Focus Drug News (Nov. 12, 2001). Pimvaserin Acadia preclinical data.

Sadzot, et al., "Hallucinogenic drug interactions at human brain 5-HT2 receptors: Implications for treating LSD-induced hallucinogenesis," *Psychopharmacology* (1989) 98:495-499.

Saltzman, et al., "Cloning of the human serotonin 5-HT2 and 5-HT1C receptor subtypes," *Biochemical and Biophysical Research Communications* (1991) 181(3):1469-1478.

Saxena, et al., "Cardiovascular effects of serotonin agonists and antagonists," *Journal of Cardiovascular Pharmacology* (1990) 15(Supp. 7):S17-S34.

Shanmugam, S. "Granulation Techniques and Technologies: Recent Progresses," *BioImpacts* (2015) vol. 5, No. 1, pp. 55-63.

Stoner et al., "Integrated oral bioavailability projection using in vitro screening data as a selection tool in drug discovery," *Int. J. Pharm.* (2004) vol. 269, No. 1, pp. 241-249.

Swedish Search Report for Patent Application No. 1730232-4 dated Mar. 28, 2018 (10 pages).

Vanover et al., "Pharmacological Characterization of AC-90179 [2-(4-Methoxy-phenyl)-N-(4-methyl-benzyl)-N-(1-methyl-piperidiny-4-yl)-acetamide Hydrochloride]: A Selective Serotonin 2A Receptor Inverse Agonist," *J. Pharmacology & Experimental Therapeutics* (2004) vol. 310, No. 3, pp. 943-951.

Vanover, Kimberly E. et al., "Pharmacokinetics, tolerability, and safety of ACP-103 following single or multiple oral dose administration in healthy volunteers," *Journal of Clinical Phamacol.* (2007) vol. 47, No. 6, pp. 704-714.

Vinogradova et al., Palladium Catalyzed Cross-Coupling of Aryl Chlorides and Triflates with Socium Cyanate: A Practical Synthesis of Unsymmetrical Ureas, J. Am. Chem. Soc. 134:11132-11135 (2012).

Yoshimura et al., "Hypervalent Iodine Catalyzed Hofmann Rearrangement of Carboxamides Using Oxone as Terminal Oxidant," JOC 77:11399-11404 (2012).

Yoshimura et al., (Tosylimino)phenyl-λ3-iodane as a Reagent for the Synthesis of Metyl Carbamates via Hofmann Rearrangement of Aromatic and Aliphatic Carboxamides, Journal of Organic Chemistry 77:2087-2091 (2012).

U.S. Appl. No. 17/080,731, Formulations of Pimavanserin, filed Oct. 26, 2020, Pending, N/A.

Bekris et al. "Cerebrospinal Fluid Ab42 Levels and APP processing pathway genes in Parkinson's disease," Movement Disorders, 2015, vol. 30, No. 7, pp. 936-944, 2015.

Buddhala et al. "Correlation between descreased CSF a-synuclein and Ab1-42 in Parkinson disease," Neurobiology of Aging, 2015, vol. 36, pp. 476-484, 2015.

Lashley et al. "Cortical a-synuclein load is associated with amyloid-b plaque burden in subset of Parkinson disease patients," Acta Neuropathol. 2008, 115, 417-425.

Ye at al. "Improving response inhibition in Parkinson's disease with Atomoxetine." Biological Psychiatry, Apr. 15, 2015, 77, 740-748.

Anonymous, "Use of Liquids and/or Soft Foods as Vehicles for Drug Administration: General Considerations for Selection and in Vitro Methods for Product Quality Assessments Guidance for Industry," Jul. 13, 2018 (Jul. 13, 2018), XP055676101, Retrieved from the Internet: URL:https://www.fda.gov/media/114872/downl <http://www.fda.gov/media/114872/downl> [retrieved on Mar. 12, 2020].

Aizenstein et al., "Frequent Amyloid Deposition Without Significant Cognitive Impairment Among the Elderly," Arch. Neurol. 65(11):1509-1517 (2008).

Bhana et al., "A Review of its Use in the Management of the Behavioural and Psychological Symptoms of Dementia," Drugs & Aging 16(6):451-471 (2000).

Cummings et al., "Pimavanserin: Potential Treatment for Dementia-Related Psychosis." J. Prev. Alzheimers Dis. 5(4): 253-258 (2018).

Lane et al., "Alzheimer's Disease," Eur. J. Neurol. 25:59-70 (2018).

Matsumura et al., "A New Method for Synthesis of Unsymmetrical Ureas Using Electrochemically Prepared Trifluoroethyl Carbamates," J. Org. Chem. 65:1549-1551 (2000).

Basha, 1988, "Synthesis of N,N'-disubstituted Ureas from Carbamates," Tetrahedron Letters, vol. 29, Issue 21, pp. 2525-2526.

Bogolubsky et al., 2014, "Bis(2,2,2-trifluoroethyl) carbonate as a condensing agent in one-pot parallel synthesis of unsymmetrical aliphatic ureas", ACS Combinatorial Science, vol. 16, Issue 6, pp. 303-308.

Bogolubsky et al., 2014, "Bis(2,2,2-trifluoroethyl) carbonate as a condensing agent in one-pot parallel synthesis of unsymmetrical aliphatic ureas", pp. S1-S67, retrieved from http://pubs.acs.org/doi/suppl/10.1021/co500025f/supl_file_co500025f_si_001.pdf, Table S2, pp. S9, entry 47.

Database CA [online] Chemical Abstracts Service, Columbus, Ohio, US; 2016, Wang et al., "Intermediate of pimavanserin and its analog, preparation method thereof and preparation method of pimavanserin and its analog", XP002761533, retrieved from STN Database accession No. 2016:451070 (reference date: Mar. 23, 2016).

Database CA [online] Chemical Abstracts Service, Columbus, Ohio, US; 2016, Zheng, Xuchun et al: "A process for preparing pimavanserin tartrate", XP002761538, retrieved from STN Database accession No. 2016:1261850 (reference date: Aug. 3, 2016).

Database WPI Week 201622, Derwent Publications Ltd., London, GB; AN 2016-17318M, XP002761536 (reference date: Aug. 19, 2015).

Database WPI Week 201623, Derwent Publications Ltd., London, GB; AN 2015-708058, XP002761532 (reference date: Oct. 7, 2015).

Database WPI Week 201635, Derwent Publications Ltd., London, GB; AN 2016-02257F, XP002761534 (reference date: Dec. 2, 2015).

Database WPI Week 201640, Derwent Publications Ltd., London, GB; AN 2016-01442V, XP002761535 (reference date: Dec. 16, 2015).

Database WPI Week 201641, Derwent Publications Ltd., London, GB; AN 2016-24419S, XP002761537 (reference date: Apr. 13, 2016).

European Patent Office, Communication pursuant to Article 94(3) EPC, European Patent Application No. 16745321.6, dated Sep. 23, 2019, pp. 1-4.

European Patent Office, Communication pursuant to Rule 114(2) EPC with Third Party Observation, European Patent Application No. 16745321.6, dated Aug. 19, 2019, pp. 1-9.

Hacksell et al., 2014, "On the Discovery and Development of Pimavanserin: A Novel Drug Candidate for Parkinson's Psychosis," Neurochem. Res., vol. 39, pp. 2008-2017.

Han et al., 2007, "Synthesis of Carbamates and Ureas Using Zr(IV)-Catalyzed Exchange Processes," Organic Letters, vol. 9, No. 8, pp. 1517-1520.

(56) References Cited

OTHER PUBLICATIONS

Hegarty et al., 1995, "Functions Containing a Carbonyl Group and Two Heteroatoms Other Than a Halogen or Chalcogen," pp. 501-502, in Chapter 6.16, Comprehensive Organic Functional Group Transformations, vol. 6 (First Edition), Pergamon.
International Search Report and Written Opinion dated Oct. 14, 2016 of Internatinoal Patent Application No. PCT/US2016/042933 (published as WO 2017/015272) (13 pages).
Matsumura et al., 2000, "A New Method for Synthesis of Unsymmetrical Ureas Using Electrochemically Prepared Trifluoroethyl Carbamates," J. Org. Chem., vol. 65, Issue 5, pp. 1549-1551.
Sandler et al., 1986, "Subsection E Reaction of Amine with Urethanes and Carbamates," pp. 161-162, in Chapter 6—Ureas, Organic Functional Group Preparations, vol. 2 (Second Edition), Academic Press.
Sartori et al., 2005, "Product Class 8: Acyclic and Cyclic Ureas," in Science of Synthesis, 18: Category 3, Compounds with Four and Three Carbon Heteroatom Bonds, Thieme Verlagsgruppe, Stuttgart, New York, pp. 665-758.
Thavonekham, A Practical Synthesis of Ureas from Phenyl Carbamates, Synthesis, 1994, 11, pp. 1189-1194.
Volk et al: "Synthesis of methyl ethyl and phenyl 4 2 methylpropoxy benzyl carbamates", IP.com Disclosure No. IPCOM000244271D, The IP.com Prior Art Database (Nov. 27, 2015).

\* cited by examiner

METHODS FOR PREPARING N-(4-FLUOROBENZYL)-N-(1-METHYLPIPERIDIN-4-YL)-N'-(4-(2-METHYLPROPYLOXY)PHENYLMETHYL) CARBAMIDE AND ITS TARTRATE SALT AND POLYMORPHIC FORM C

CROSS-REFERENCE TO RELATED APPLICATIONS

This application is a continuation of U.S. application Ser. No. 15/744,636, filed Jan. 12, 2018, which is a U.S. National Stage Application of International Application No. PCT/US2016/042933, filed Jul. 19, 2016, which claims the benefit of U.S. Provisional Application No. 62/194,725, filed Jul. 20, 2015, the disclosure of each of which is incorporated by reference herein in its entirety.

BACKGROUND

Field

The present disclosure relates to the fields of medicine and chemistry. More particularly, the present disclosure relates one or more methods of obtaining N-(4-fluorobenzyl)-N-(1-methylpiperidin-4-yl)-N'-(4-(2-methylpropyloxy)-phenylmethyl) carbamide, its tartrate salt, and polymorphs, intermediates and syntheses and uses thereof.

Description of the Related Art

N-(4-fluorobenzyl)-N-(1-methylpiperidin-4-yl)-N'-(4-(2-methylpropyloxy)-phenylmethyl)carbamide, also known as pimavanserin, is described in WO 2004/064738, WO 2006/037043, WO 2007/124136 and WO 2008/144326, each of which is incorporated herein by reference in its entirety. These publications describe routes to prepare pimavanserin. Although the routes described are sufficient to produce pimavanserin, there may be other routes providing other opportunities.

SUMMARY

Disclosed herein include methods of preparing pimavanserin.

Disclosed herein are also intermediate products obtainable from the methods of preparing pimavanserin.

Disclosed herein are methods of preparing pimavanserin comprising contacting an intermediate according to Formula (A),

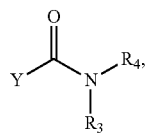
(A)

or a salt thereof, with an intermediate according to Formula (B).

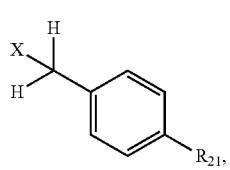
(B)

or a salt thereof, to produce pimavanserin.

In certain embodiments, Y is selected from $-OR_1$ or $-NR_{2a}R_{2b}$.

$R_1$, $R_{2a}$, $R_{2b}$, independently of each other are selected from the group consisting of hydrogen, substituted or unsubstituted $C_{1-6}$ alkyl, substituted or unsubstituted aryl or $R_{2a}$ and $R_{2b}$ taken together with the nitrogen to which they are attached form a substituted or unsubstituted heteroalicyclyl, substituted or unsubstituted aryl or a substituted or unsubstituted heteroaryl.

$R_3$ is selected from hydrogen or substituted or unsubstituted heteroalicyclyl.

$R_4$ is selected from substituted or unsubstituted aralkyl.

X is selected from the group consisting of $-OR_{22}$ and $-NR_{23}R_{24}$.

$R_{21}$ is selected from $-OCH_2CH(CH_3)_2$ or F.

$R_{22}$ is selected from hydrogen and substituted or unsubstituted $C_{1-6}$ alkyl.

One of $R_{23}$ and $R_{24}$ is hydrogen and the other of $R_{23}$ and $R_{24}$ is N-methylpiperidin-4-yl, or both $R_{23}$ and $R_{24}$ are hydrogen.

In some embodiments, $R_3$ is substituted or unsubstituted heteroalicyclyl; $R_{21}$ is $-OCH_2CH(CH_3)_2$; $R_{23}$ is hydrogen; and $R_{24}$ is hydrogen.

In other embodiments, $R_3$ is hydrogen; $R_{21}$ is F; and one of $R_{23}$ and $R_{24}$ is hydrogen and the other of $R_{23}$ and $R_{24}$ is N-methylpiperidin-4-yl.

In certain embodiments of the methods provided herein, $R_1$ is selected from the group consisting of methyl, ethyl, propyl, butyl, pentyl, trifluoroethyl and phenyl.

In certain embodiments, $R_{2a}$ and $R_{2b}$ independently of each other are selected from the group consisting of hydrogen, methyl, ethyl, propyl, butyl, pentyl, trifluoroethyl, p-nitrophenyl and phenyl. In some embodiments, $R_{2a}$ and $R_{2b}$ taken together with the nitrogen to which they are attached form a substituted or unsubstituted imidazolyl, substituted or unsubstituted benzotriazole, substituted or unsubstituted pyrrolyl, substituted or unsubstituted morpholinyl.

In some embodiments, the intermediate according to Formula (A) is a compound according to Formula (A2):

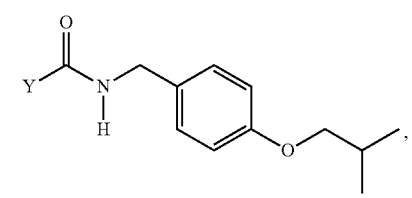
(A2)

and the intermediate according to Formula (B) is a compound according to Formula (B2):

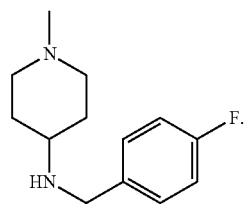
(B2)

In some embodiments, the intermediate according to Formula (A) is a compound according to Formula (A3):

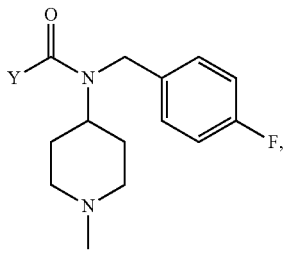
(A3)

and the intermediate according to Formula (B) is a compound according to Formula (B3):

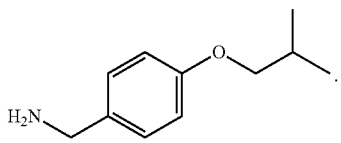

In some embodiments, Y is —$OR_1$ and $R_1$ is selected from the group consisting of methyl, ethyl, propyl, butyl, pentyl, trifluoroethyl and phenyl. In some embodiments, $R_1$ is phenyl.

In some embodiments, Y is $NR_{2a}R_{2b}$, wherein $R_{2a}$ and $R_{2b}$ taken together with the nitrogen to which they are attached form a substituted or unsubstituted imidazolyl.

Disclosed herein is also a method of synthesizing the compound according to Formula (I), i.e., N-(1-methylpiperidin-4-yl)-N-(4-fluorophenylmethyl)-N'-(4-(2-methylpropyloxy) phenylmethyl) carbamide, i.e., pimavanserin, as a tartrate salt, comprising reacting N-(1-methylpiperidin-4-yl)-N-(4-fluorophenylmethyl)-N'-(4-(2-methylpropyloxy) phenylmethyl) carbamide with tartaric acid in the presence of a solvent, e.g., ethanol. In certain embodiments, the tartrate salt is a hemi-tartrate salt. In some embodiments the pimavanserin tartrate is a hemi-tartrate having a molecular weight of 1005.2.

In other aspects, provided herein is a compound according to Formula (A):

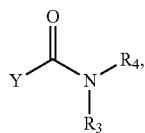
(A)

or salt, hydrate, solvate, polymorph, or stereoisomers thereof, wherein Y, $R_3$ and $R_4$ are as defined below.

In some embodiments, Y is selected from —$OR_1$ or —$NR_{2a}R_{2b}$.

$R_1$, $R_{2a}$, $R_{2b}$, independently of each other are selected from the group consisting of hydrogen, substituted or unsubstituted $C_{1-6}$ alkyl, substituted or unsubstituted aryl, substituted or unsubstituted aralkyl, or $R_{2a}$ and $R_{2b}$ taken together with the nitrogen to which they are attached form a substituted or unsubstituted heteroalicyclyl, substituted or unsubstituted aryl or a substituted or unsubstituted heteroaryl.

$R_3$ is selected from hydrogen or substituted or unsubstituted heteroalicyclyl.

$R_4$ is selected from substituted or unsubstituted aralkyl.

In some embodiments, the compound according to Formula (A) is selected from the group consisting of Formula (C)-(F):

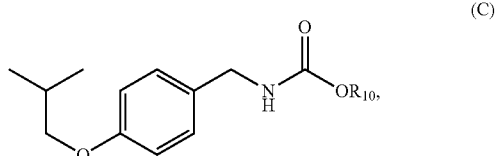
(C)

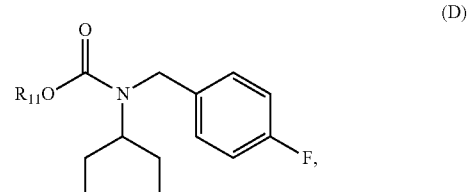
(D)

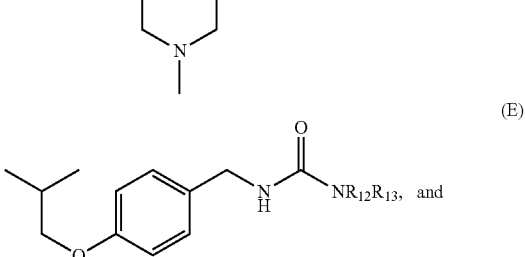
(E)

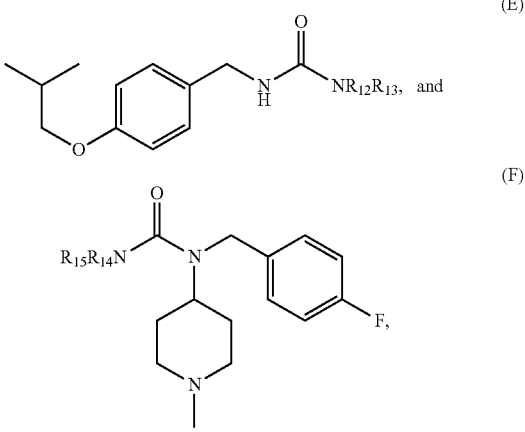
(F)

wherein $R_{10}$, $R_{11}$, $R_{12}$, $R_{13}$, $R_{14}$ and $R_{11}$ are as defined below.

In some embodiments, $R_{10}$ and $R_{11}$ are selected from hydrogen, substituted or unsubstituted $C_{1-6}$ alkyl, substituted or unsubstituted aryl, and substituted or unsubstituted aralkyl.

In some embodiments, $R_{12}$, $R_{13}$, $R_{14}$, and $R_{15}$ independently of each other are selected from hydrogen, substituted or unsubstituted $C_{1-6}$ alkyl, and substituted or unsubstituted aralkyl.

In certain embodiments, $R_{12}$ and $R_{13}$ taken together with the nitrogen to which they are attached form a substituted or unsubstituted heteroalicyclyl, substituted or unsubstituted aryl or a substituted or unsubstituted heteroaryl.

In certain embodiments, $R_{14}$ and $R_{15}$ taken together with the nitrogen to which they are attached form a substituted or unsubstituted heteroalicyclyl, substituted or unsubstituted aryl or a substituted or unsubstituted heteroaryl.

In some embodiments, $R_{10}$ is selected from methyl, ethyl, trifluoroethyl, pentyl, and phenyl; $R_{11}$ is selected from methyl, ethyl, trifluoroethyl, pentyl, and phenyl; $R_{12}$, $R_{13}$, $R_{14}$, $R_{15}$ are hydrogen.

In some embodiments, $R_{12}$ and $R_{13}$ taken together with the nitrogen to which they are attached form an imidazolyl or benzotriazole.

In some embodiments, $R_{14}$ and $R_{15}$ taken together with the nitrogen to which they are attached form an imidazolyl or benzotriazole.

In certain embodiments, the compound is a compound according to Formula (C) or (D), wherein $R_{10}$ and $R_{11}$ are each selected from phenyl.

DETAILED DESCRIPTION

Definitions

Unless defined otherwise, all technical and scientific terms used herein have the same meaning as is commonly understood by one of ordinary skill in the art. All patents, applications, published applications and other publications referenced herein are incorporated by reference in their entirety. In the event that there is a plurality of definitions for a term herein, those in this section prevail unless stated otherwise.

As used herein, any "R" group(s) such as, without limitation, $R_1$, $R_2$, $R_3$, $R_4$, $R_5$, $R_8$, $R_9$, and $R_{10}$, represent substituents that can be attached to the indicated atom. A non-limiting list of R groups includes but are not limited to hydrogen, alkyl, alkenyl, alkynyl, cycloalkyl, cycloalkenyl, cycloalkynyl, aryl, heteroaryl, and heteroalicyclyl. If two "R" groups are covalently bonded to the same atom or to adjacent atoms, then they may be "taken together" or "combined to" as defined herein to form a cycloalkyl, aryl, heteroaryl or heteroalicyclyl group. For example, without limitation, if $R_a$ and $R_b$ of an $NR_aR_b$ group are indicated to be "taken together" or "combined to", it means that they are covalently bonded to one another at their terminal atoms to form a ring that includes the nitrogen:

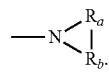

Whenever a group is described as being "unsubstituted or substituted," if substituted, the substituent(s) (which may be present one or more times, such as 1, 2, 3 or 4 times, valencies permitting) are independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

When a substituent is deemed to be "substituted," the substituent itself is substituted with one or more of the indicated substituents. When the referenced substituent is substituted, it is meant that one or more hydrogen atoms on the referenced group may be replaced with a group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

The protecting groups that may form the protective derivatives of the above substituents are known to those of skill in the art and may be found in Greene and Wuts, Protective Groups in Organic Synthesis, 3$^{rd}$ Ed., John Wiley & Sons, New York, N.Y., 1999, which is hereby incorporated by reference in its entirety.

As used herein, "$C_m$ to $C_n$," "$C_m$-$C_n$," or "$C_{m-n}$" in which "m" and "n" are integers refers to the number of carbon atoms in the relevant group. That is, the group can contain from "m" to "n", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$—, $CH_3CH(CH_3)CH_2$— and $(CH_3)_3C$—. If no "m" and "n" are designated with regard to a group, the broadest range described in these definitions is to be assumed.

As used herein, "alkyl" refers to a straight or branched hydrocarbon chain group that is fully saturated (no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms, such as "$C_{1-6}$". The alkyl group could also be a lower alkyl having 1 to 4 carbon atoms. The alkyl group of the compounds may be designated as "$C_1$-$C_4$ alkyl," "$C_{1-4}$ alkyl" or similar designations. By way of example only, "$C_1$-$C_4$ alkyl" or "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like. When an alkyl is substituted, it can be substituted with one substituent or more than one substituent, where substituents are individually and independently selected from alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

As used herein, "alkenyl" refers to an alkyl group that contains in the straight or branched hydrocarbon chain one or more double bonds. If more than one double bond is present, the double bonds may be conjugated or not conjugated. The alkenyl group may have 2 to 20 carbon atoms (whenever it appears herein, a numerical range such as "2 to 20" refers to each integer in the given range; e.g., "2 to 20 carbon atoms" means that the alkenyl group may consist of 2 carbon atom, 3 carbon atoms, 4 carbon atoms, etc., up to and including 20 carbon atoms, although the present definition also covers the occurrence of the term "alkenyl" where no numerical range is designated). One or more substituents on a substituted alkenyl are individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

As used herein, "alkynyl" refers to an alkyl group that contains in the straight or branched hydrocarbon chain one or more triple bonds. The alkynyl group may have 2 to 20 carbon atoms (whenever it appears herein, a numerical range such as "2 to 20" refers to each integer in the given range; e.g., "2 to 20 carbon atoms" means that the alkynyl group may consist of 2 carbon atom, 3 carbon atoms, 4 carbon atoms, etc., up to and including 20 carbon atoms, although the present definition also covers the occurrence of the term "alkynyl" where no numerical range is designated). An alkynyl group may be unsubstituted or substituted. When substituted, the substituent(s) may be selected from the same groups disclosed above with regard to alkenyl group substitution.

As used herein, "hetero" may be attached to a group and refers to one or more carbon atom(s) and the associated hydrogen atom(s) in the attached group have been independently replaced with the same or different heteroatoms selected from nitrogen, oxygen, phosphorus and sulfur.

As used herein, "heteroalkyl," by itself or in combination with another term, refers to a straight or branched alkyl group consisting of the stated number of carbon atoms, where one or more carbon atom(s), such as 1, 2, 3 or 4 carbon atom(s), and the associated hydrogen atom(s) have been independently replaced with the same or different heteroatoms selected from nitrogen, oxygen and sulfur. The carbon atom(s) being replaced may be in the middle or at the end of the alkyl group. Examples of heteroalkyl include, but are not limited to, —S-alkyl, —O-alkyl, —NH-alkyl, alkyl-O-alkyl, etc.

As used herein, "aryl" refers to a carbocyclic (all carbon) ring or two or more fused rings (rings that share two adjacent carbon atoms) that have a fully delocalized pi-electron system. Examples of aryl groups include, but are not limited to, benzene, naphthalene and azulene. An aryl group may be substituted. When substituted, hydrogen atoms are replaced by substituent group(s) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. When substituted, substituents on an aryl group may form a non-aromatic ring fused to the aryl group, including a cycloalkyl, cycloalkenyl, cycloalkynyl, and heterocyclyl.

As used herein, "heteroaryl" refers to a monocyclic or multicyclic aromatic ring system (a ring system with fully delocalized pi-electron system), in which at least one of the atoms in the ring system is a heteroatom, that is, an element other than carbon, including but not limited to, nitrogen, oxygen and sulfur. Examples of "heteroaryl" include, but are not limited to, furan, thiophene, phthalazine, pyrrole, oxazole, thiazole, imidazole, pyrazole, isoxazole, isothiazole, triazole, thiadiazole, pyridine, pyridazine, pyrimidine, pyrazine, tetrazole, and triazine. A heteroaryl may be substituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. When substituted, substituents on a heteroaryl group may form a non-aromatic ring fused to the aryl group, including a cycloalkyl, cycloalkenyl, cycloalkynyl, and heterocyclyl.

An "aralkyl" or "arylalkyl" is an aryl group connected, as a substituent, via an alkylene group. The alkylene and aryl group of an aralkyl may be substituted. Examples include but are not limited to benzyl, substituted benzyl, 2-phenylethyl, 3-phenylpropyl, and naphthylalkyl. In some cases, the alkylene group is a lower alkylene group.

A "heteroaralkyl" or "heteroarylalkyl" is heteroaryl group connected, as a substituent, via an alkylene group. The alkylene and heteroaryl group of heteroaralkyl may be substituted. Examples include but are not limited to 2-thienylmethyl, 3-thienylmethyl, furylmethyl, thienylethyl, pyrrolylalkyl, pyridylalkyl, isoxazolylalkyl, pyrazolylalkyl and imidazolylalkyl, and their substituted as well as benzo-fused analogs. In some cases, the alkylene group is a lower alkylene group.

An "alkylene" is a straight-chained tethering group, forming bonds to connect molecular fragments via their terminal carbon atoms. The alkylene may have 1 to 20 carbon atoms. The alkylene may also be a medium size alkylene having 1 to 10 carbon atoms, such as "$C_{1-6}$". The alkylene could also be a lower alkylene having 1 to 4 carbon atoms. The alkylene may be designated as "$C_1$-$C_4$ alkylene", "$C_{1-4}$ alkylene" or similar designations. Non-limiting examples include, methylene (—$CH_2$—), ethylene (—$CH_2CH_2$—), propylene (—$CH_2CH_2CH_2$—), and butylene (—$(CH_2)_4$—) groups. In the case of methylene, the two connected fragments are connected to the same carbon atom. A lower alkylene group may be substituted.

As used herein, "heteroalkylene" by itself or in combination with another term refers to an alkylene group consisting of the stated number of carbon atoms in which one or more of the carbon atoms, such as 1, 2, 3 or 4 carbon atom(s), are independently replaced with the same or different heteroatoms selected from oxygen, sulfur and nitrogen. Examples of heteroalkylene include, but not limited to —$CH_2$—O—, —$CH_2$—$CH_2$—O—, —$CH_2$—$CH_2$—$CH_2$—O—, —$CH_2$—NH—, —$CH_2$—$CH_2$—NH—, —$CH_2$—$CH_2$—$CH_2$—NH—, —$CH_2$—$CH_2$—NH—$CH_2$—, —O—$CH_2$—$CH_2$—O—$CH_2$—$CH_2$—O—, —O—$CH_2$—$CH_2$—O—$CH_2$—$CH_2$—, and the like.

As used herein, "alkylidene" refers to a divalent group, such as =CR'R", which is attached to one carbon of another group, forming a double bond. Alkylidene groups include, but are not limited to, methylidene (=$CH_2$) and ethylidene (=CHCH$_3$). As used herein, "arylalkylidene" refers to an alkylidene group in which either R' or R" is an aryl group. An alkylidene group may be substituted.

As used herein, "alkoxy" refers to the group —OR wherein R is an alkyl, e.g., methoxy, ethoxy, n-propoxy, 1-methylethoxy (isopropoxy), cyclopropoxy, n-butoxy, isobutoxy, sec-butoxy, tert-butoxy, amoxy, tert-amoxy and the like. An alkoxy may be substituted.

As used herein, "alkylthio" refers to the formula —SR wherein R is an alkyl defined as above, e.g., methylmercapto, ethylmercapto, n-propylmercapto, 1-methyl ethyl mercapto (isopropylmercapto), n-butylmercapto, iso-butylmercapto, sec-butylmercapto, tert-butylmercapto, and the like. An alkylthio may be substituted.

As used herein, "aryloxy" and "arylthio" refers to RO— and RS—, in which R is an aryl as defined above, e.g., phenoxy, naphthalenyloxy, azulenyloxy, anthracenyloxy, naphthalenylthio, phenylthio and the like. Both an aryloxy and arylthio may be substituted.

As used herein, "alkenyloxy" refers to the formula —OR wherein R is an alkenyl as defined above, e.g., vinyloxy, propenyloxy, n-butenyloxy, iso-butenyloxy, sec-pentenyloxy, tert-pentenyloxy, and the like. The alkenyloxy may be substituted.

As used herein, "acyl" refers to a hydrogen, alkyl, alkenyl, alkynyl, or aryl connected, as substituents, via a carbonyl group. Examples include formyl, acetyl, propanoyl, benzoyl, and acryl. An acyl may be substituted.

As used herein, "cycloalkyl" refers to a completely saturated (no double bonds) mono- or multi-cyclic hydrocarbon ring system. When composed of two or more rings, the rings may be joined together in a fused, bridged or spiro-connected fashion. Cycloalkyl groups may range from $C_3$ to $C_{10}$, in other embodiments it may range from $C_3$ to $C_6$. A cycloalkyl group may be unsubstituted or substituted. Typical cycloalkyl groups include, but are in no way limited to, cyclopropyl, cyclobutyl, cyclopentyl, cyclohexyl, and the like. If substituted, the substituent(s) may be an alkyl or selected from those indicated above with regard to substitution of an alkyl group unless otherwise indicated. When substituted, substituents on a cycloalkyl group may form an aromatic ring fused to the cycloalkyl group, including an aryl and a heteroaryl.

As used herein, "cycloalkenyl" refers to a cycloalkyl group that contains one or more double bonds in the ring although, if there is more than one, they cannot form a fully delocalized pi-electron system in the ring (otherwise the group would be "aryl," as defined herein). When composed of two or more rings, the rings may be connected together in a fused, bridged or spiro-connected fashion. A cycloalkenyl group may be unsubstituted or substituted. When substituted, the substituent(s) may be an alkyl or selected from the groups disclosed above with regard to alkyl group substitution unless otherwise indicated. When substituted, substituents on a cycloalkenyl group may form an aromatic ring fused to the cycloalkenyl group, including an awl and a heteroaryl.

As used herein, "cycloalkynyl" refers to a cycloalkyl group that contains one or more triple bonds in the ring. When composed of two or more rings, the rings may be joined together in a fused, bridged or spiro-connected fashion. Cycloalkynyl groups may range from $C_8$ to $C_{12}$. A cycloalkynyl group may be unsubstituted or substituted. When substituted, the substituent(s) may be an alkyl or selected from the groups disclosed above with regard to alkyl group substitution unless otherwise indicated. When substituted, substituents on a cycloalkynyl group may form an aromatic ring fused to the cycloalkynyl group, including an aryl and a heteroaryl.

As used herein, "heteroalicyclic" or "heteroalicyclyl" refers to a 3- to 18 membered-ring which consists of carbon atoms and from one to five heteroatoms selected from the group consisting of nitrogen, oxygen and sulfur. The heteroalicyclic or heteroalicyclyl groups may range from $C_3$ to $C_{10}$, in other embodiments it may range from $C_3$ to $C_9$ and in other embodiments it may range from $C_3$ to $C_8$. The "heteroalicyclic" or "heteroalicyclyl" may be monocyclic, bicyclic, tricyclic, or tetracyclic ring system, which may be joined together in a fused, bridged or spiro-connected fashion; and the nitrogen, carbon and sulfur atoms in the "heteroalicyclic" or "heteroalicyclyl" may be oxidized; the nitrogen may be quaternized; and the rings may also contain one or more double bonds provided that they do not form a fully delocalized pi-electron system throughout all the rings. Heteroalicyclyl groups may be unsubstituted or substituted. When substituted, the substituent(s) may be one or more groups independently selected from the group consisting of alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, C-amido, N-amido, S-sulfonamido, N-sulfonamido, isocyanato, thiocyanato, isothiocyanato, nitro, silyl, haloalkyl, haloalkoxy, trihalomethanesulfonyl, trihalomethanesulfonamido, and amino, including mono- and di-substituted amino groups, and the protected derivatives thereof. Examples of such "heteroalicyclic" or "heteroalicyclyl" include but are not limited to, azepinyl, azetidinyl, dioxolanyl, imidazolinyl, imidazolinolyl morpholinyl, oxetanyl, oxiranyl, piperidinyl N-oxide, piperidinyl (e.g. 1-piperidinyl, 2-piperidinyl, 3-piperidinyl and 4-piperidinyl), pyrrolidinyl, (e.g. 1-pyrrolidinyl, 2-pyrrolidinyl and 3-pyrrolidinyl), piperazinyl, pyranyl, 4-piperidonyl, tetrahydrofuranyl, tetrahydropyranyl, pyrazolidinyl, 2-oxopyrrolidinyl, thiamorpholinyl, thiamorpholinyl sulfoxide, and thiamorpholinyl sulfone. When substituted, substituents on a heteroalicyclyl group may form an aromatic ring fused to the heteroalicyclyl group, including an aryl and a heteroaryl.

A "(cycloalkyl)alkyl" is a cycloalkyl group connected, as a substituent, via an alkylene group. The alkylene and cycloalkyl of a (cycloalkyl)alkyl may be substituted. Examples include but are not limited cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

A "(cycloalkenyl)alkyl" is a cycloalkenyl group connected, as a substituent, via an alkylene group. The alkylene and cycloalkenyl of a (cycloalkenyl)alkyl may be substituted. In some cases, the alkylene group is a lower alkylene group.

A "(cycloalkynyl)alkyl" is a cycloalkynyl group connected, as a substituent, via an alkylene group. The alkylene and cycloalkynyl of a (cycloalkynyl)alkyl may be substituted. In some cases, the alkylene group is a lower alkylene group.

As used herein, "halo" or "halogen" refers to F (fluoro), Cl (chloro), Br (bromo) or I (iodo).

As used herein, "haloalkyl" refers to an alkyl group in which one or more of the hydrogen atoms are replaced by halogen. Such groups include but are not limited to, chloromethyl, fluoromethyl, difluoromethyl, trifluoromethyl and 1-chloro-2-fluoromethyl, 2-fluoroisobutyl. A haloalkyl may be substituted.

As used herein, "haloalkoxy" refers to a RO-group in which R is a haloalkyl group. Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted.

A "C-carboxy" group refers to a "—C(=O)OR" group in which R can be the same as defined with respect to O-carboxy. A C-carboxy may be substituted.

A "trihalomethanesulfonyl" group refers to an "$X_3CSO_2$—" group" wherein X is a halogen.

A dashed bond, represents an optional unsaturation between the atoms forming the bond. This bond may be unsaturated (e.g., C=C, C=N, C=O) or saturated (e.g., C—C, C—N, C—O). When a dashed bond is present in a ring system it may form part of an aromatic ring system.

A "nitro" group refers to a "—$NO_2$" group.

A "cyano" group refers to a "—CN" group.

A "cyanato" group refers to an "—OCN" group.

An "isocyanato" group refers to a "—NCO" group.

A "thiocyanato" group refers to a "—SCN" group.

A "carbonyl" group refers to a "—C(=O)—" group.

A "thiocarbonyl" group refers to a "—C(=S)—" group.

An "oxo" group refers to a "=O" group.

An "isothiocyanato" group refers to an "—NCS" group.

A "sulfinyl" group refers to an "—S(=O)—R" group in which R can be the same as defined with respect to O-carboxy. A sulfinyl may be substituted.

A "sulfonyl" group refers to an "$SO_2R$" group in which R can be the same as defined with respect to O-carboxy. A sulfonyl may be substituted.

An "S-sulfonamido" group refers to a "—$SO_2NR_AR_B$" group in which $R_A$ and $R_B$ independently of each other can be the same as defined with respect to the R group as defined for O-carboxy, or combined to form a ring system selected from the group consisting of substituted or unsubstituted $C_{3-8}$ cycloalkyl, substituted or unsubstituted $C_{3-8}$ cycloalkenyl, substituted or unsubstituted $C_{3-8}$ cycloalkyl, substituted or unsubstituted $C_{3-8}$ cycloalkenyl, substituted or unsubstituted heteroalicyclyl, substituted or unsubstituted aryl, and substituted or unsubstituted heteroaryl. An S-sulfonamido may be substituted.

An "N-sulfonamido" group refers to a "$RSO_2N(R_A)$—" group in which R and $R_A$ independently of each other can be the same as defined with respect to the R group as defined for O-carboxy. An N-sulfonamido may be substituted.

A "trihalomethanesulfonamido" group refers to an "$X_3CSO_2N(R)$—" group with X as halogen and R can be the same as defined with respect to O-carboxy. A trihalomethanesulfonamido may be substituted.

A "C-amido" group refers to a "—C(=O)$NR_AR_B$" group in which $R_A$ and $R_B$ independently of each other can be the same as defined with respect to the R group as defined for O-carboxy, or combined to form a ring system selected from the group consisting of substituted or unsubstituted $C_{3-8}$ cycloalkyl, substituted or unsubstituted $C_{3-8}$ cycloalkenyl, substituted or unsubstituted $C_{3-8}$ cycloalkyl, substituted or unsubstituted $C_{3-8}$ cycloalkenyl, substituted or unsubstituted heteroalicyclyl, substituted or unsubstituted aryl, and substituted or unsubstituted heteroaryl. A C-amido may be substituted.

An "N-amido" group refers to a "RC(=O)$NR_A$—" group in which R and $R_A$ independently of each other can be same as defined with respect to the R group as defined for O-carboxy. An N-amido may be substituted.

An "ester" refers to a "—C(=O)OR" group in which R can be the same as defined with respect to O-carboxy. An ester may be substituted.

A lower alkoxyalkyl refers to an alkoxy group connected via a lower alkylene group. A lower alkoxyalkyl may be substituted.

An "amino" refers to "$RNH_2$" (primary amines), "$R_2NH$" (secondary amines), and "$R_3N$" (tertiary amines). An amino group may be substituted.

An aminoalkyl refers to an amino group connected via a alkylene group. A aminoalkyl may be substituted.

Any unsubstituted or monosubstituted amine group on a compound herein can be converted to an amide, any hydroxyl group can be converted to an ester and any carboxyl group can be converted to either an amide or ester using techniques well-known to those skilled in the art (see, for example, Greene and Wuts, Protective Groups in Organic Synthesis, $3^{rd}$ Ed., John Wiley & Sons, New York, N.Y., 1999).

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

Herein are thus described methods of obtaining pimavanserin as well as novel compounds used as intermediates in the preparation of pimavanserin. Pimavanserin, salts and polymorphs thereof, as well as methods of obtaining pimavanserin has previously been described in for example WO 2004/064738, WO 2006/037043, WO 2007/124136 and WO 2008/144326.

Pimavanserin has the chemical formula (I)

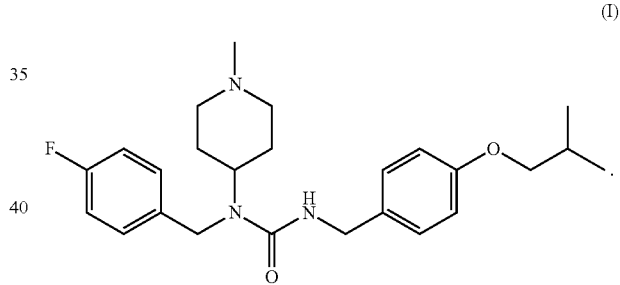

Optionally pimavanserin can be referred to as (N-(4-fluorophenylmethyl)-N-(1-methylpiperidin-4-yl)-N'-(4-(2-methyl propyl oxy)phenylmethyl)carbamide).

The compound of formula I can be obtained by the methods described herein in high purity and yields. High purity is herein defined as a purity of at least 70%, such as at least 80%, such as at least 90%, such as at least 92%, such as at least 94%, such as at least 96%, such as at least 98%, such as at least 99%. According to some embodiments herein pimavanserin is obtained as a tartrate salt. According to some embodiments the pimavanserin tartrate is pimavanserin hemi-tartrate. According to some embodiments the pimavanserin tartrate is polymorphic Form C.

In some embodiments pimavanserin tartrate is obtained in a purity of at least 96%, e.g. at least 98% based on HPLC (high performance liquid chromatography).

In some embodiments pimavanserin tartrate in polymorphic Form C is obtained in a purity of at least 98%, e.g. at least 99% based on HPLC.

According to methods disclosed herein pimavanserin is possible to produce in large scale. Some of the routes described herein have shown particular usefulness when it comes to producing pimavanserin in large scale manufacturing, i.e., suitable for preparing pharmaceutical compositions of pimavanserin.
Pimavanserin has previously been synthesized according to the method disclosed in Scheme I.
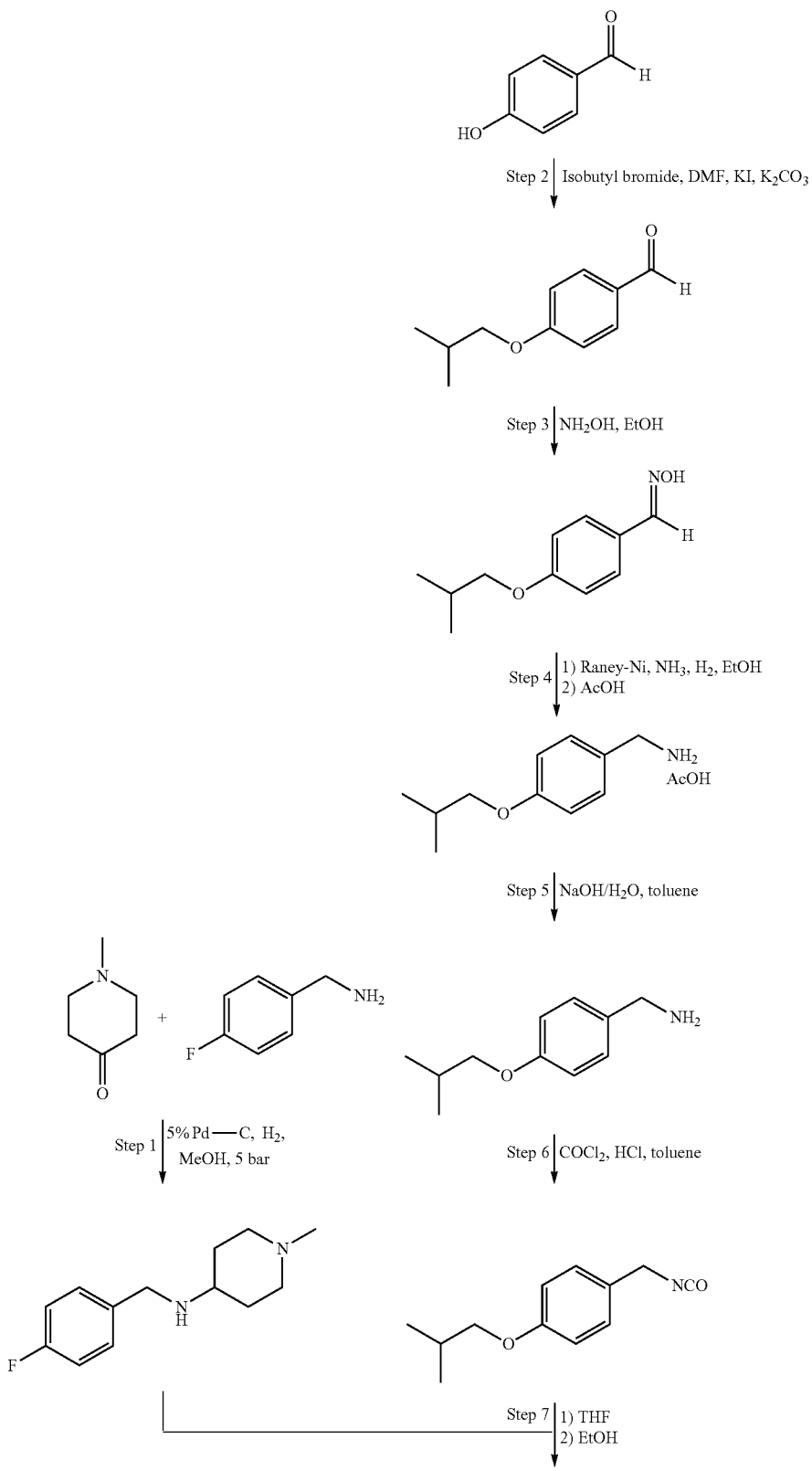
Scheme I: Previous Synthesis of Pimavanserin

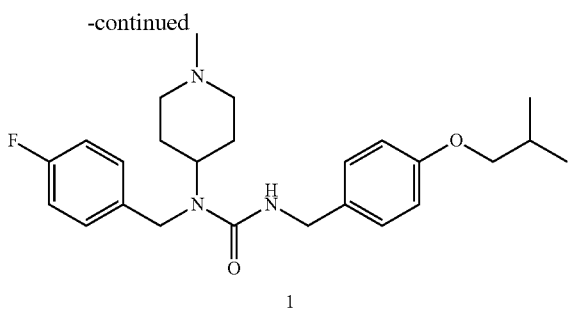

1

As demonstrated in the examples provided herein, there are other methods suitable to prepare pimavanserin. Such methods may, for example, result in an improved manufacturing process, e.g., scalability for large scale production, improved purity, improved sourcing of materials, and/or improved environmental profile, etc.

In some aspects disclosed herein, methods of preparing pimavanserin use starting materials that differ from those in Scheme I.

For instance, starting materials used in the methods described herein, such as those designated as SM1 (N-(4-fluorobenzyl)-1-methylpiperidin-4-amine) and SM2 ((4-isobutoxyphenyl)methanamine), may be obtained by any route and thereafter, e.g., as disclosed herein, converted in one or more steps into pimavanserin. Some useful routes for preparing SM1 and SM2 are disclosed in the exemplary section.

Examples of methods of producing pimavanserin are summarized below.

Pimavanserin (1) may be manufactured by reacting SM1 with a carbamate derivative of SM2, as depicted in Scheme II.

Scheme II: SM1 plus SM2 Carbamate Pimavanserin Synthesis

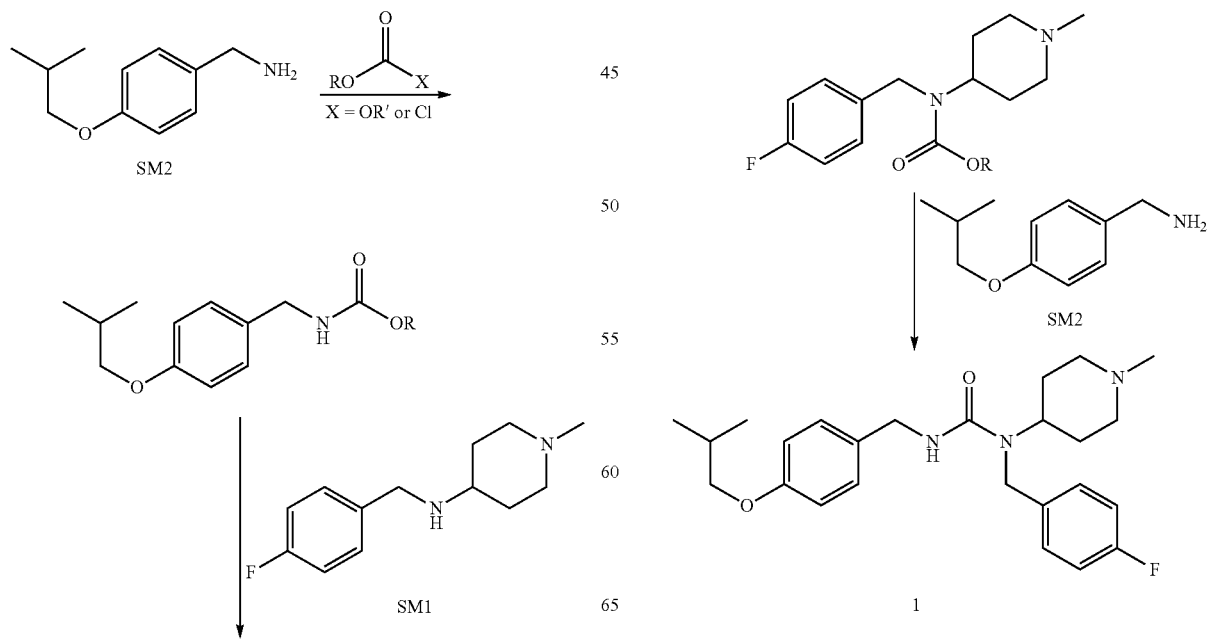

Alternatively, pimavanserin may be manufactured by reacting SM2 with a carbamate derivative of SM1, as depicted in Scheme III.

Scheme III: SM2 plus SM1 Carbamate Pimavanserin Synthesis

More specifically, pimavanserin may be manufactured via activation of a dialkyl carbonate or a diaryl carbonate, e.g., by reacting SM1 and SM2, or the freebase of SM2b with a suitable carbonate such as dimethyl carbonate, ethylmethyl carbonate, diethyl carbonate, disuccinimidyl carbonate, dimethyl 2,2'-(carbonylbis(oxy))dibenzoate or diphenyl carbonate in order to obtain, and optionally isolate a carbamate of either SM1 or SM2, e.g., as shown in the following structures (where "Me" is methyl and "Ph" is phenyl).

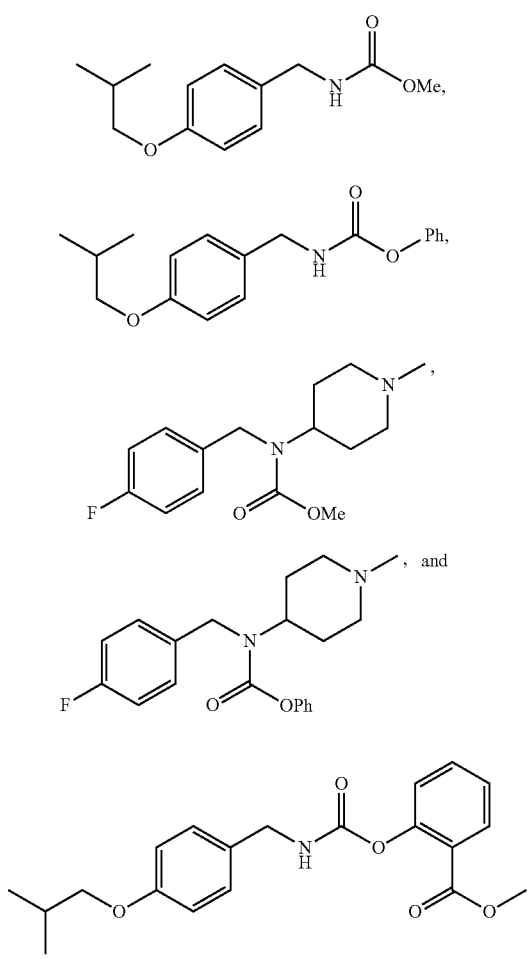

I1, I1.1, I2, I2.1, I2.3 or another suitable carbamate is then reacted with SM2 or SM1 respectively to obtain pimavanserin. In addition to the carbonates mentioned above, other suitable carbonates may be used. In some embodiments dimethyl carbonate (DMC) is used. DMC is useful as it generates methanol as by-product and the catalyst may be recycled resulting in an environmentally beneficial route. Additionally, a route employing DMC could be preferred compared to the conventional process both economically and for process safety reasons. In some embodiments diphenyl carbonate is used, in which case the easily separated co-product is phenol. In some embodiments the reaction is run using the carbonate as a solvent and in some embodiments another suitable solvent is used, e.g., toluene and THF. To improve yields and conversions, catalysts such as NaO$^t$Bu and Zr(O$^t$Bu)$_4$ are used. In some embodiments co-catalysts such as 2-hydroxypyridine and 4-methyl-2-hydroxyquinoline are used. In some embodiments the carbamate of SM1 or SM2 (or free-based SM2b) may be prepared by reacting SM1 or SM2 respectively with a slight excess (e.g., 1.1 to 2 eq) of diphenyl carbonate in a suitable solvent such as toluene or acetonitrile. The mixture may then be stirred for at suitable time such as 1-24 h at a suitable temperature such as room temperature. In one embodiment SM2 or SM2b (which may be freebased) is converted to a carbonate according to any of the methods described above.

Pimavanserin may also be manufactured via a chloroformate reagent, e.g., by reacting either SM1 or SM2 (or free-based SM2b) with a suitable chloroformate such as an alkyl chloroformate (e.g., methyl chloroformate, ethyl chloroformate, trifluoroethyl chloroformate), or an aryl chloroformate (e.g., phenyl chloroformate) in order to obtain, and optionally isolate a carbamate of either SM1 or SM2, as shown above (I1, I1.1, I2, and I2.1) and in the following structures:

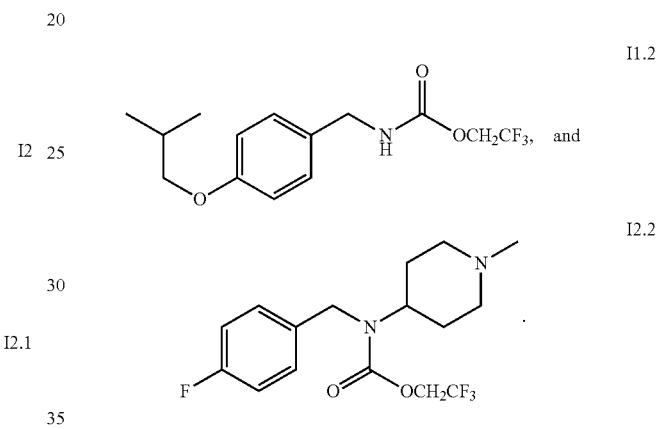

I1, I1.1, I1.2, I2, I2.1 I2.2 or another suitable carbamate is thereafter reacted with SM2 or SM1 respectively to obtain pimavanserin. The carbamate of SM1 may for example be prepared by dissolving SM1 in a suitable amount of toluene or THF and adding a suitable base such as potassium carbonate (e.g., dissolved in water) or sodium hydride suspended in THF. Suitable equivalents of base are for example 1-2 eq. To the mixture containing SM1 a suitable chloroformate such as phenyl chloroformate (e.g., 1-2 eq) whereafter the mixture for example may be stirred at a suitable temperature, such as room temperature, for a suitable time such as 6-36 h. The carbamate of SM2 or SM2b may for example be prepared by adding a slight excess of phenyl chloroformate to SM2 or SM2b (which is free-based, e.g., using sodium hydroxide in toluene) dissolved in a suitable solvent such as toluene or THF, wherein the mixture additionally comprises an excess (e.g., 1-2 eq) of a suitable base such as triethyl amine, sodium hydroxide or sodium carbonate. The mixture is for example maintained at a low temperature, such as −3 to 10° C., or at temperature of about 20-50° C. (depending on what base is used) for about 1 hour or longer in order to generate the carbamate of SM2 or SM2b in high purity (e.g., >90%). In addition to the chloroformates mentioned above other suitable chloroformates may be used.

In one embodiment the formed carbamate is the carbamate of formula I1.1,

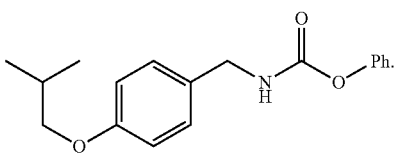

I1.1

The carbamate of formula I1.1 is characterized for example by a DSC melting point at 99° C. and an exothermic event of 48 J/g at about 191° C., which were determined using a DSC822e Differential Scanning calorimeter (Mettler Toledo, Columbus Ohio) following the manufacturer's recommended standard procedures and conditions.

In one embodiment, SM2 or SM2b is synthesized by one of the routes depicted in Scheme IV. These routes have the advantage of using isobutyl alcohol as a reagent instead of the previously used isobutyl bromide (e.g., Scheme 1), which is an alkylating agent known to be a health hazard and a potential genotoxin. In one embodiment SM2 or SM2b is synthesized using the starting materials isobutyl alcohol and 4-fluorobenzonitrile.

facilitated sourcing, improved environmental profile, reduced cost and require less complicated handling of reagents as compared to the conventionally used route currently used to form pimavanserin. In contrast to the prior syntheses of pimavanserin (e.g., Scheme 1), the use of carbamate intermediates avoids the direct employment of phosgene, which is a toxic reagent. Phosgene in GMP production is generally to be avoided as known to those skilled in the art. The carbamates routes, for example, the route described herein where SM2 or SM2b, generated from 4-fluorobenzonitrile and isobutanol, and brought in contact with phenyl chloroformate to generate I1.1, which thereafter is converted to pimavanserin, or a salt thereof, such as a pharmaceutically acceptable salt thereof, e.g. a hemi-tartrate salt, have several advantages already mentioned and result in a cheaper and shorter process, and avoid toxic starting materials. The process can be run as a single operation, or multiple operations and hence provide further flexibility in view of potential production sites. For example, using 4-fluorobenzonitrile as starting material provides a facilitated process as it is possible to generate SM2 and SM2b in "one pot". As mentioned there is no need for isobutyl

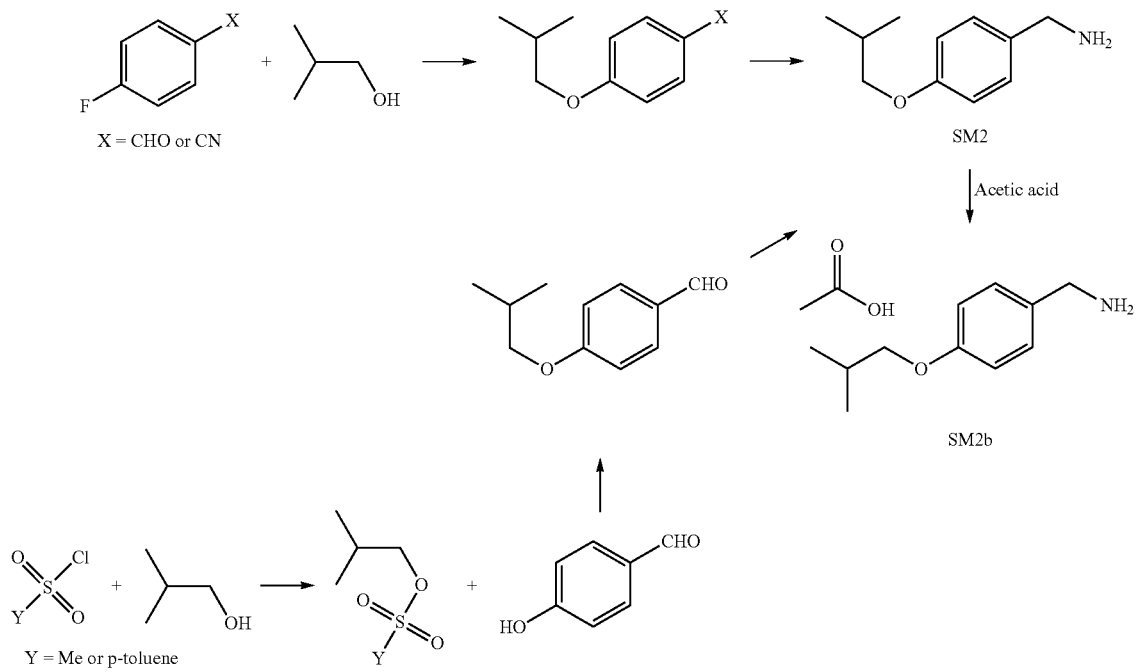

Scheme IV: Alternative Synthesis of SM2 Intermediates

In some embodiments the conversion into I1.1 is complete and in some embodiments minor amounts (e.g., less than 5%, such as less than 3%, such as less than 1%, such as less than 0.5%) of the impurity 1,3-bis(4-isobutoxybenzyl)urea, and less than 10%, such as less than 5%, such as less than 3%, such as less than 1% of the impurity phenol are observed. Typically the yield of I1.1 is at least 85%, such as at least 88%, such as at least 90%.

One of I1, I1.1, I1.2, I2, I2.1 I2.2 (carbamate intermediates) is thereafter reacted with the appropriate SM1, SM2 (SM2b or the freebase of SM2b), to obtain pimavanserin.

The carbamate routes, i.e., those routes forming pimavanserin via a carbamate intermediate provide benefits such as bromide and the process requires less process steps to generate SM2 and/or SM2b compared to other disclosed routes of preparing pimavanserin. The process can be run to generate pimavanserin tartrate as polymorph C without isolating any intermediate product prior to the salt and/or polymorph generation.

Examples of suitable solvents for generating the carbamate intermediates are polar and non-polar aprotic solvents. More specific examples are acetonitrile, tetrahydrofuran, 2-methyl tetrahydrofuran, dimethylformamide, hexane, chloroform, dichloromethane, ethers (e.g., diethyl ether, diisopropyl ether, methyl tert-butyl ether), ethyl acetate, toluene, ethyl acetate, isopropyl acetate, and water. According to some aspects the solvent should be less than 50 vol % compared to the other constituents in order to obtain improved conversion of the starting materials. In some embodiments toluene or isopropyl acetate is selected as the solvent.

Although the reaction may be run without an additional agent, such as a catalyst, some embodiments include one or more additional agent(s) such as a base, e.g., triethyl amine, diisopropyl amine, pyridine or alkali metal carbonates, such as sodium carbonate, potassium carbonate, sodium hydroxide, potassium hydroxide, sodium phosphate or potassium phosphate. The agent(s) may provide improved conversion time.

Although the reaction may be run without the above listed additional agent(s) at room temperature, it is generally considered that an increased temperature provides a faster completion rate, however additional amounts of impurities may be generated. Examples of suitable agents are a base, such as triethyl amine or alkali metal salts, such as sodium carbonate or potassium carbonate. The agent when used in suitable amounts such as 0.1-5 eq, for example 0.5-1.5 eq, such as 1 eq improved the conversion time and resulted in improved yield. In some embodiments potassium carbonate is selected as the catalyst as it has shown to reduce the amount of the impurity 1,3-bis(4-isobutoxybenzyl)urea. In some embodiments the potassium carbonate is used in 0.4-1 eq. In some embodiments the temperatures used to carry out the formation of the carbamate intermediate are from −3° C. to 50° C., for example between 5-25° C., such as between 15-23° C. Additionally, heating is used in some embodiments in order to achieve phase separation, and suitable temperatures are above 40° C., 50° C., 60° C., 70° C., 80° C., 90° C., 100° C. or 110° C. In some embodiments the temperature is kept at about 65° C., 85° C., or 105° C. In some embodiments room temperature is used.

In some embodiments coupling of the carbamate intermediates with a second starting material is carried out using a slight excess of one of the starting materials, for example a 1:1.1 to 1:1.5 ratio. In some embodiments disclosed herein an excess of either starting material is used, Alternatively a 1:1 ratio of the carbamate intermediate and the second starting material is used in order to limit formation of impurities, as well as unreacted starting materials in the crude product. The carbamate may be an isolated intermediate or an intermediate generated in-situ (i.e. not isolated).

In some embodiments conversion of the starting materials into pimavanserin, using the above described conditions, is completed within 24 h, such as within 3-8 hours, such as within 4-6 hours.

In one embodiment, I1.1 (e.g., obtained via reacting SM2 with phenyl chloroformate or diphenyl carbonate) was mixed (1:1) with SM1 in toluene and about 0.5 eq potassium carbonate ($K_2CO_3$) in order to generate pimavanserin. The HPLC purity of the obtained pimavanserin can be above 99%, such as above 99.5%, such as about 99.6%, such as about 99.7%, such as about 99.8%, such as about 99.9%; and the yield can be above 90%, such as above 92%, such as about 94%, such as about 96%. Additionally, pimavanserin obtained via phenyl chloroformate or diphenyl carbonate routes are above 85% or about 90% or more.

In one embodiment the carbamate intermediate is obtained using a carbonate reagent, for example diphenyl carbonate. In one embodiment the carbamate intermediate is obtained using a chloroformate reagent, for example phenyl chloroformate.

Generating pimavanserin using any of the above described carbamate routes (i.e., those employing a carbamate intermediate) may be done by mixing the carbamate with SM1 or SM2 (depending on what carbamate intermediate is used). Generally the reaction can be carried out at a temperature of up to 100° C. In some embodiments the temperature is 50-60° C. In some embodiments one or more additional agent(s), for example a base such as an alkali metal carbonate (e.g., sodium carbonate or potassium carbonate), or an organic base such as triethyl amine is used. In some embodiments potassium carbonate is used as it reduces the conversion time. Generally the reaction is carried out within 24 hours, but using an alkali metal carbonate such as potassium carbonate as an additional agent has made it possible to reduce the reaction time to about 4-6 h.

Examples of suitable solvents for generating pimavanserin are polar and non-polar aprotic solvents. More specific examples are acetonitrile, tetrahydrofuran, 2-methyl tetrahydrofuran, dimethylformamide, hexane, chloroform, dichloromethane, ethers (e.g., diethyl ether, diisopropyl ether or methyl tert-butyl ether), ethyl acetate, toluene, ethyl acetate, isopropyl acetate or water. In some embodiments toluene or isopropyl acetate is used as solvent.

Pimavanserin may also be manufactured via reaction of SM2 or SM1 with carbonyldiimidazole (CDI) or 1,1' carbonylbisbenzotriazole, forming intermediates I4, I4.1, I6 and I6.1 respectively. The intermediates may be isolated and characterized and accordingly have the following formulas:

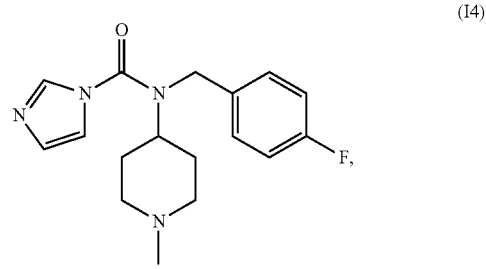

(I4)

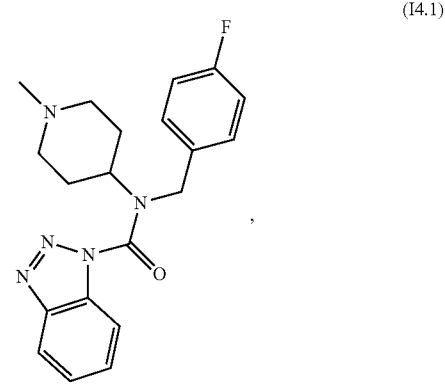

(I4.1)

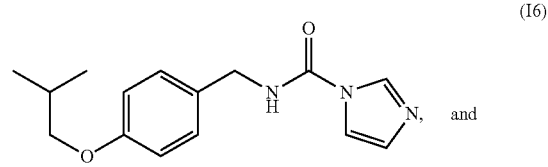

(I6)

and

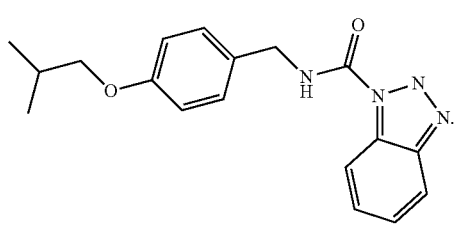

(I6.1)

I4, I4.1, is reacted with SM1; alternatively I6 or I6.1 is reacted with SM2 to obtain pimavanserin. In some embodiments the process to produce pimavanserin goes via the formation of I6. The intermediate I6 may for example be prepared by dissolving SM2b in water containing sodium hydroxide (about 30%), and adding toluene, followed by heating the mixture to obtain separated layers and then separating the layers, e.g., by distillation. To CDI (slight excess, e.g., 1.2-1.8 eq) in toluene was added the previously obtained SM2 while the temperature was kept around room temperature. Layer separation was performed once the reaction had gone to completion by addition of water at a temperature below 15° C., and I6 obtained from the organic phase by conventional methods. The intermediate may be isolated or telescoped directly into the next step where it is converted into pimavanserin by adding SM1 and heating (e.g., at about 50° C.) the mixture in toluene followed by aqueous work-up and collecting pimavanserin in the organic phase.

Advantages using CDI, are for example operational safety and surprisingly a simplified process (e.g., fewer impurities) making the route preferred compared to the conventional process shown in Scheme 1.

Pimavanserin may also be manufactured via reaction of SM2 with di-tert-butyl dicarbonate (Boc₂O), forming intermediate I7. The intermediate may be isolated as a compound having the formula:

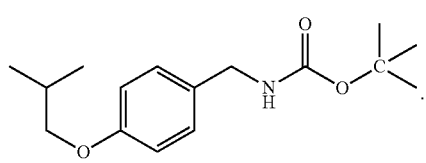

I7

Intermediate I7 thereafter may be reacted with SM1 with catalytic amounts of DMAP (4-dimethylaminopyridine) to obtain pimavanserin.

Pimavanserin may also be manufactured via reaction with a suitable urea derivative or carbamate derivative. SM1 or SM2 may be reacted with a urea derivative such as urea and thereafter optionally isolated or reacted with SM2 or SM1 respectively in order to obtain pimavanserin. A similar option would be to react SM2 with urea and 3-methylbutan-1-ol to give isopentyl (4-isobutoxybenzyl)carbamate (I8) which can be converted to an isocyanate intermediate, 1-isobutoxy-4-(isocyanotomethyl)benzene (I9), by distillation at temperature 160-180° C. The isocyanate I9 can be reacted with SM1 to obtain pimavanserin.

Pimavanserin may also be manufactured via treatment of SM1 or SM2 with a suitable carbamate. Examples of suitable carbamates are alkyl carbamates such as methyl carbamate, and ethyl carbamate. Consequently intermediates of for example formulae (I10) and (I11) may be isolated or directly reacted with SM2 or SM1 respectively in order to obtain pimavanserin.

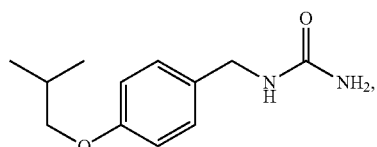

I10

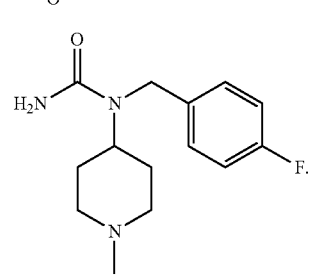

I11

Intermediates I10 and I11 can then be reacted with a suitable aldehyde or hydroxyl moiety.

Publications such as J. Am. Chem. Soc., 1923, 45, 1816; Chem Ber 1965, 98, 1097; and Org Prep Proc 1986, 18, 149, in general, disclose reactions conditions and procedures suitable to generate ureas and carbamates.

The methods described above to generate pimavanserin may be further complemented by obtaining pimavanserin in different salt forms, such as tartrate salt. Of general interest are routes for obtaining SM1 and SM2 respectively. For example obtaining SM1 and SM2 respectively from different starting material would be of interest and within the capacity of those skilled in the art. For example obtaining SM1 as a salt such as a hydrochloric or tartaric salt may confer benefits. A described advantages in view of sourcing and toxicity may also impact the selection of raw materials and for example (4-isobutoxyphenyl)methanamine may be prepared using different raw materials, for example 4-fluorobenzonitrile and isobutanol, or 4-hydroxybenzaldehyde and isobutyl bromide, or isobutyl methanesulfonate, or 4-fluorobenzaldehyde and isobutanol. In some embodiments the 4-fluorobenzonitrile and isobutanol is used to generate (4-isobutoxyphenyl)methanamine which may be used in preparing pimavanserin according to many of the routes described herein.

Some embodiments described herein relate to a method of preparing pimavanserin (N-(4-fluorophenylmethyl)-N-(1-methylpiperidin-4-yl)-N'-(4-(2-methylpropyloxy)phenylmethyl)carbamide), the method comprising:

contacting an intermediate according to Formula (A),

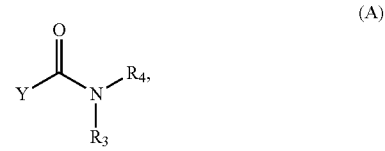

(A)

or a salt thereof, with an intermediate according to Formula (B), or a salt thereof,

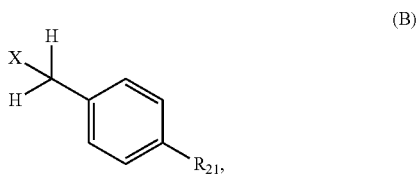

(B)

or a salt thereof, to produce pimavanserin, wherein Y, $R_3$, $R_4$, X and $R_{21}$ are as defined below.

Y is selected from —$OR_1$ or —$NR_{2a}R_{2b}$.

$R_1$, $R_{2a}$, $R_{2b}$, independently of each other are selected from the group consisting of hydrogen, substituted or unsubstituted $C_{1-6}$ alkyl, substituted or unsubstituted aryl; or $R_{2a}$ and $R_{2b}$ taken together with the nitrogen to which they are attached form a substituted or unsubstituted heteroalicyclyl, substituted or unsubstituted aryl or a substituted or unsubstituted heteroaryl.

$R_3$ is selected from hydrogen or substituted or unsubstituted heteroalicyclyl.

$R_4$ is selected from substituted or unsubstituted aralkyl.

X is selected from the group consisting of —$OR_{22}$ and —$NR_{23}R_{24}$.

$R_{21}$ is selected from —$OCH_2CH(CH_3)_2$ or F.

$R_{22}$ is selected from hydrogen and substituted or unsubstituted $C_{1-6}$ alkyl.

One of $R_{23}$ and $R_{24}$ is hydrogen and the other is N-methylpiperidin-4-yl, or both $R_{23}$ and $R_{24}$ are hydrogen.

Some embodiments relate to a method wherein $R_1$ is selected from the group consisting of methyl, ethyl, propyl, butyl, pentyl, trifluoroethyl and phenyl.

Some embodiments relate to a method wherein $R_{2a}$ and $R_{2b}$ independently of each other are selected from the group consisting of hydrogen, methyl, ethyl, propyl, butyl, pentyl, trifluoroethyl, p-nitrophenyl and phenyl, or $R_{2a}$ and $R_{2b}$ taken together with the nitrogen to which they are attached form a substituted or unsubstituted imidazolyl, substituted or unsubstituted benzotriazole, substituted or unsubstituted pyrrolyl, substituted or unsubstituted morpholinyl. The substituted or unsubstituted imidazolyl may according to some embodiments be selected from $1\lambda^2$-imidazole and 1-methyl-$1\lambda^4,2\lambda^2$-imidazole.

Some embodiments relate to a method wherein the intermediate according to Formula (A) is a compound according to Formula (A2)

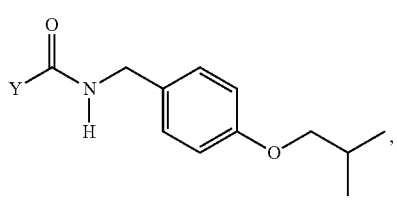

(A2)

and the intermediate according to Formula (B) is a compound according to Formula (B2)

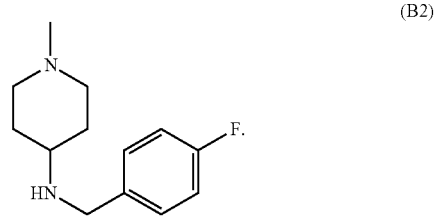 [SMILES: CN1CCC(NCc2ccc(F)cc2)CC1]

(B2)

In some embodiments, the intermediate according to Formula (A) is a compound according to Formula (A3)

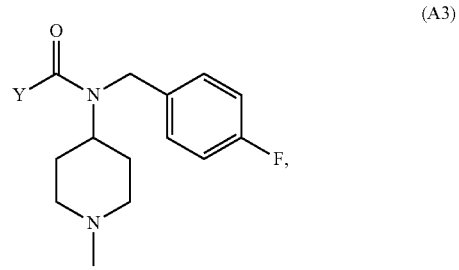

(A3)

and the intermediate according to Formula (B) is a compound according to Formula (B3)

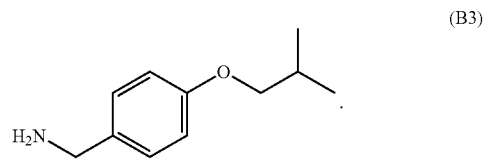

(B3)

Some embodiments relate to Y being —$OR_1$, for example $R_1$ is methyl, ethyl, propyl, butyl, pentyl, trifluoroethyl and phenyl. In some embodiments $R_1$ is phenyl. In some embodiments the compound according to Formula (A2) or (A3) (where Y is —O-phenyl) is obtained using diphenyl carbonate or phenyl chloroformate.

Some embodiments relate to Y being $NR_{2a}R_{2b}$, wherein $R_{2a}$ and $R_{2b}$ taken together with the nitrogen to which they are attached form a substituted or unsubstituted imidazolyl. In some embodiments the compound according to Formula (A2) or (A3) (where Y is $NR_{2a}R_{2b}$) is obtained using CDI.

Some embodiments described herein relate to a method of preparing pimavanserin (N-(4-fluorophenylmethyl)-N-(1-methylpiperidin-4-yl)-N'-(4-(2-methylpropyloxy)phenylmethyl)carbamide), the method comprising forming a an intermediate according to Formula (A),

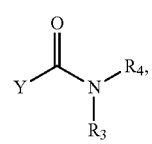

(A)

or salts, hydrates, solvates, polymorphs, and stereoisomers thereof, wherein Y, $R_3$ and $R_4$ are as defined below:

Y is selected from —$OR_1$ or —$NR_{2a}R_{2b}$;

$R_1$, $R_{2a}$, $R_{2b}$, independently of each other are selected from the group consisting of hydrogen, substituted or unsubstituted $C_{1-6}$ alkyl, substituted or unsubstituted aryl or $R_{2a}$ and $R_{2b}$ taken together with the nitrogen to which they are attached form a substituted or unsubstituted heteroalicyclyl, substituted or unsubstituted aryl or a substituted or unsubstituted heteroaryl; $R_3$ is selected from hydrogen and substituted or unsubstituted heteroalicyclyl, and $R_4$ is selected from substituted or unsubstituted aralkyl.

In some embodiments the compound according to Formula (A) is selected from a compound according to Formula (C)-(F)

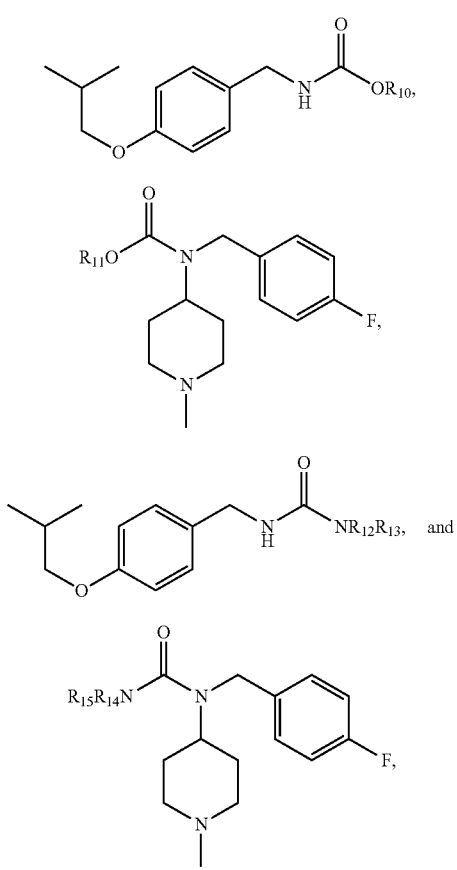

wherein $R_{10}$ and $R_{11}$ independently of each other are selected from hydrogen, substituted or unsubstituted $C_{1-6}$ alkyl, substituted or unsubstituted aryl, and substituted or unsubstituted aralkyl; and $R_{12}$, $R_{13}$, $R_{14}$, and $R_{15}$ independently of each other are selected from hydrogen, substituted or unsubstituted $C_{1-6}$ alkyl, and substituted or unsubstituted aralkyl.

In certain embodiments wherein compound according to Formula (A) is a compound according to Formula (E), $R_{12}$ and $R_{13}$ taken together with the nitrogen to which they are attached form a substituted or unsubstituted heteroalicyclyl, or a substituted or unsubstituted heteroaryl.

In certain embodiments wherein compound according to Formula (A) is a compound according to Formula (F), $R_{14}$ and $R_{15}$ taken together with the nitrogen to which they are attached form a substituted or unsubstituted heteroalicyclyl, or a substituted or unsubstituted heteroaryl.

In some embodiments $R_{10}$ is selected from the group consisting of methyl, ethyl trifluoroethyl, pentyl, and phenyl. In some embodiments $R_{11}$ is selected from the group consisting of methyl, ethyl, trifluoroethyl, pentyl, and phenyl. In some embodiments $R_{12}$, $R_{13}$, $R_{14}$, $R_{15}$ are hydrogen. In some embodiments $R_{12}$ and $R_{13}$ taken together with the nitrogen to which they are attached form an imidazolyl or benzotriazole. In some embodiments $R_{14}$ and $R_{15}$ taken together with the nitrogen to which they are attached form an imidazolyl or benzotriazole.

In some embodiments the intermediate is a compound according to Formula (C) or (D).

In some embodiment $R_{10}$ is phenyl. In some embodiments the intermediate is a compound according to Formula (C) and $R_{10}$ is phenyl.

In some embodiments $R_{11}$ is phenyl. In some embodiments the intermediate is a compound according to Formula (D) and $R_{11}$ is phenyl.

In some embodiments the method comprises contacting 4-fluorobenzonitrile and isobutyl alcohol to provide 4-isobutoxy-benzonitrile, converting 4-isobutoxy-benzonitrile to (4-isobutoxyphenyl)methanamine, contacting (4-isobutoxyphenyl)methanamine with phenylchloroformate, or diphenylcarbonate, to give phenyl (4-isobutoxybenzyl)carbamate, and contacting the phenyl (4-isobutoxybenzyl)carbamate with N-(4-fluorobenzyl)-1-methylpiperidin-4-amine providing N-(4-fluorobenzyl)-N-(1-methylpiperidin-4-yl)-N'-(4-(2-methylpropyloxy)phenylmethyl)carbamide. In some embodiments N-(4-fluorobenzyl)-N-(1-methylpiperidin-4-yl)-N'-(4-(2-methylpropyloxy)phenylmethyl)carbamide is obtained as a tartrate salt.

Accordingly the intermediate compounds described herein are used in the preparation of pimavanserin and/or pimavanserin tartrate.

The compound of formula I (pimavanserin) has a low solubility in water. Accordingly, in some embodiments, salt forms of the compound are provided that are water soluble and hence have enhanced bioavailability and improved processing characteristics for the preparation and formulation of drug compositions. Examples of suitable salts are tartrate, citrate, fumarate, maleate, maliate, phosphate, succinate, sulphate, and edisylate.

It was found that a hemi-tartrate of N-(4-fluorobenzyl)-N-(1-methylpiperidin-4-yl)-N'-(4-(2-methylpropyloxy)phenylmethyl)carbamide is particularly suitable. Accordingly, one embodiment provides N-(4-fluorobenzyl)-N-(1-methylpiperidin-4-yl)-N'-(4-(2-methylpropyloxy) phenylmethyl carbamide hemi-tartrate (pimavanserin tartrate) according to the formula IV,

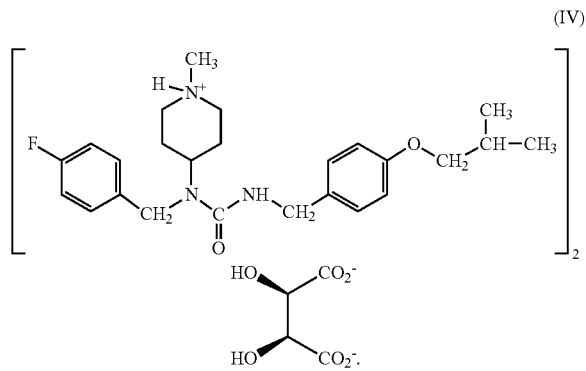

Accordingly, some embodiments disclosed herein relate to preparing a compound of formula IV (pimavanserin tartrate) by the methods described herein.

The compound of formula IV may be prepared as an integrated part of the process for synthesizing the compound of formula I as described above by using tartaric acid as the salt forming acid. Alternatively, the tartrate salt may be formed by reaction of the isolated compound of formula I with tartaric acid.

In one embodiment, N-(4-fluorobenzyl)-N-(1-methylpiperidin-4-yl)-N'-(4-(2-methylpropyloxy) phenylmethylcarbamide hemi-tartrate is formed by adding tartaric acid to the compound of formula I, and isolating the hemi-tartrate of the compound of formula I. The hemi-tartrate may be isolated through precipitation by cooling, solvent removal, adding an anti-solvent, or a combination of these methods. In one embodiment, one or more solvents are added in one of the steps in the reaction that have a low solubility for the hemi-tartrate, such as isopropyl acetate, a ketone (such as acetone or 2-butanone or MEK), and/or tetrahydrofuran. The hemi-tartrate precipitates and forms a suspension, which may be stirred for up to 3 days before filtering off the solid from the reaction mixture preferably at ambient conditions. The solid residue may be washed, and then dried at temperatures up to 50° C., if desired, under vacuum.

The hemi-tartrate of formula IV is obtained in high yields and purity. The mother liquors can be used to isolate more hemi-tartrate of formula IV in the usual manner. The hemi-tartrate may be further purified by conversion to the free base of formula I and isolating a solution of the base, which is then used to re-precipitate the hemi-tartrate by the addition of tartaric acid.

In some embodiments pimavanserin tartrate is obtained in a purity of at least 96%, e.g. at least 98% based on HPLC (high performance liquid chromatography). A suitable HPLC method is for example using a Waters system such as Waters alliance LC-System/Agilent 1100, 1200, 1260 and a detector 2487, PDA (2996)/DAD, VWD. A suitable column is Waters XBridge C18, 15 cm×4.6 mm, 5 µm. A, or equivalent, suitable test solution can be a 100 µg/ml solution containing the sample dissolved in 50 vol % aqueous solution (pH 9.0) (eluent A) and 50 vol % of a solution of acetonitrile and 20 vol % methanol (eluent B). Additional setup parameters may for example be the following: Flow rate: 1.0 ml/min, Temperature of column oven: 40° C., Temperature of auto sampler: 5° C., Wavelength: 210 nm. A mixture of eluent A (90 vol %) and eluent B (10 vol %) may for example be used. As a standard pimavanserin tartrate (or polymorphic Form C whichever is appropriate) may be used. The purity may be directly obtained from the software accompanying the equipment.

In some embodiments, the hemi-tartrate of the compound of formula I is obtained by reaction with tartaric acid where both reagents are dissolved in ethanol. It was surprisingly discovered that efficient removal of impurities can be obtained by precipitation of the tartrate from ethanol.

Pimavanserin tartrate can be obtained in many polymorphic forms as described in WO2006/037043. For example, the procedure described using MEK generates polymorph C of pimavanserin. Polymorphic Form C has been found to be a thermostabile form of pimavanserin and is for example characterized by having an endotherm with an onset of between 167 and 177 C.° as obtained by differential scanning calorimetry (DSC) in accordance with USP <891>. The DSC was obtained using a Mettler-Toledo 822, using a 4-6 mg sample and 40 µl aluminium crucible with a lid and pin hole. The analysis is performed under nitrogen (10 ml/min) at a heating rate of 10° C./min between 80° C.-210° C. Optionally polymorphic Form C may be characterized by powder diffraction (pXRD), see FIG. 4 of WO2006/037043.

In some embodiments polymorphic Form C is obtained in a purity of at least 98%, e.g. at least 99% based on HPLC, for example using the method described hereinabove.

In some embodiments polymorphic Form C is obtained through direct formation from pimavanserin (as defined in Formula (I). Hence there is no need of isolating and purifying pimavanserin, or pimavanserin tartrate, as it is possible to form polymorphic Form C directly. It is possible to obtain polymorphic Form C in a purity of at least 96%, such as at least 98%, such as at least 99% via the direct formation from pimavanserin. Obtaining polymorphic Form C via direct formation from pimavanserin is considered a benefit of the process disclosed herein.

Stability and Pharmaceutical Formulations

As mentioned above, the pimavanserin and pimavanserin tartrate are each suitable as an active pharmaceutical ingredient (API) or pro-drug in pharmaceutical formulations to inhibit an activity of a monoamine receptor, preferably a serotonin receptor of the 5-HT2A subclass. Pimavanserin tartrate has very good solubility in aqueous systems and the free base is deliberated at physiological pH ranges, providing a high bioavailability. Pimavanserin tartrate possesses high storage stability.

The amount of pimavanserin tartrate required in a formulation substantially depends on type of formulation and desired dosages during administration time periods. The amount in an oral formulation may be from 0.1 to 500 mg, preferably from 0.5 to 300 mg, and more preferably from 1 to 100 mg, such as 10 to 60 such as 20 to 40 mg. Oral formulations may be solid formulations such as capsules, tablets, pills and troches, or liquid formulations such as aqueous suspensions, elixirs and syrups. Solid and liquid formulations also encompass incorporation of the compound of formula IV into liquid or solid food. Liquids also encompass solutions of pimavanserin tartrate for parenteral applications such as infusion or injection.

Pimavanserin may be formulated as a powder (e.g., micronized particles), granules, suspensions or solutions, or may be combined together with other pharmaceutically acceptable ingredients in admixing the components and optionally finely dividing them, and then filling capsules, composed for example from hard or soft gelatine, compressing tablets, pills or troches, or suspending or dissolving them in carriers for suspensions, elixirs and syrups. Coatings may be applied after compression to form pills.

Pharmaceutically acceptable ingredients are well known for the various types of formulations and may be for example binders such as natural or synthetic polymers, excipients, lubricants, surfactants, sweetening and flavouring agents, coating materials, preservatives, dyes, thickeners, adjuvants, antimicrobial agents, antioxidants and carriers for the various formulation types.

Examples for binders are gum tragacanth, acacia, starch, gelatine, and biological degradable polymers such as homo- or co-polyesters of dicarboxylic acids, alkylene glycols, polyalkylene glycols and/or aliphatic hydroxyl carboxylic acids; homo- or co-polyamides of dicarboxylic acids, alkylene di amines, and/or aliphatic amino carboxylic acids; corresponding polyester-polyamide-co-polymers, polyanhydrides, polyorthoesters, polyphosphazene and polycarbonates. The biological degradable polymers may be linear, branched or crosslinked. Specific examples are poly-glycolic acid, poly-lactic acid, and poly-d,l-lactide/glycolide. Other examples for polymers are water-soluble polymers such as polyoxaalkylenes (e.g., polyoxaethylene, polyoxapropylene and mixed polymers thereof), poly-acrylamides and hydroxylalkylated polyacrylamides, poly-maleic acid and esters or -amides thereof, poly-acrylic acid and esters or -amides thereof, poly-vinylalcohol and esters or -ethers thereof, poly-vinylimidazole, poly-vinylpyrrolidon, and natural polymers like chitosan.

Examples for excipients are phosphates such as dicalcium phosphate.

Examples for lubricants are natural or synthetic oils, fats, waxes, or fatty acid salts like magnesium stearate.

Surfactants may be anionic, cationic, amphoteric, or neutral. Examples for surfactants are lecithin, phospholipids, octyl sulfate, decyl sulfate, dodecyl sulfate, tetradecyl sulfate, hexadecyl sulfate and octadecyl sulfate, sodium oleate or sodium caprate, 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or di-stearate, glycerol mono- or di-oleate and glycerol mono- or di-palmitate, and polyoxyethylene stearate.

Examples for sweetening agents are sucrose, fructose, lactose or aspartam.

Examples for flavouring agents are peppermint, oil of wintergreen or fruit flavours like cherry or orange flavour.

Examples for coating materials are gelatine, wax, shellac, sugar or biological degradable polymers.

Examples for preservatives are methyl or propylparabens, sorbic acid, chlorobutanol, phenol and thimerosal.

Examples for adjuvants are fragrances.

Examples for thickeners are synthetic polymers, fatty acids and fatty acid salts and esters and fatty alcohols.

Examples for antioxidants are vitamins, such as vitamin A, vitamin C, vitamin D or vitamin E, vegetable extracts or fish oils.

Examples for liquid carriers are water, alcohols such as ethanol, glycerol, propylene glycol, liquid polyethylene glycols, triacetin and oils. Examples for solid carriers are talc, clay, microcrystalline cellulose, silica, alumina and the like.

The pharmaceutical formulation may also contain isotonic agents, such as sugars, buffers or sodium chloride.

Pimavanserin or pimavanserin tartrate may also be formulated as effervescent tablet or powder, which disintegrates in an aqueous environment to provide a drinking solution.

A syrup or elixir may contain the pimavanserin or pimavanserin tartrate, sucrose or fructose as sweetening agent, a preservative like methylparaben, a dye, and a flavouring agent.

Slow release formulations may also be prepared from the compound of pimavanserin or pimavanserin tartrate in order to achieve a controlled release of the active agent in contact with the body fluids in the gastro intestinal tract, and to provide a substantial constant and effective level of the active agent in the blood plasma. Pimavanserin or pimavanserin tartrate may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

Pimavanserin or pimavanserin tartrate is also useful for administering a combination of therapeutic effective agents to an animal. Such a combination therapy can be carried out in using at least one further therapeutic agent which can be additionally dispersed or dissolved in a formulation. The pimavanserin or pimavanserin tartrate and its formulations respectively can be also administered in combination with other therapeutic agents that are effective to treat a given condition to provide a combination therapy One embodiment is a method of delivering pimavanserin to a host, comprising administering to the host an effective amount of pimavanserin. A further embodiment is the use of the pimavanserin or pimavanserin tartrate for the manufacture of a medicament useful in the inhibition of an activity of a monoamine receptor, preferably a serotonin receptor of the 5-HT2A subclass.

EXAMPLES

Experimental Procedures and Instrumentation

Examples of instrumentation and methods used to assist in the preparation of compounds described herein are:

NMR Equipment: VARIAN INOVA 400 mhz.

GC-MS Equipment: TRACE GC THERMO FINNIGAN (Method: Column: ZB-SMS, 30×0.25 mm, 0.25 µm. Temp gradient: 50° C. for 2 min then to 320° C. at 20° C./min. Hold time: 15 min. Flow: 1.0 ml/min, Split: 1:50, Inj. Temp.: 200° C. Injection vol: 1 µL Diluent: Acetonitrile).

LC-MS Equipment: AGILENT 6530 ACCURATE-MASS Q-TOF (Method: Column: ACQUITY UPLC BEH C18, 100×2.1 mm, 1.7 µm. Eluent A: 0.1% HFo in Acetonitrile. Eluent B 0.1% HFo in $H_2O$. Gradient 10% A 90% B at 0 min, 95% A 5% B at 15 min, 95% A 5% B at 20 min. Flow: 0.25 ml/min, Temp: 40° C. Injection vol: 1 µL. Diluent: Acetonitrile.); or LCQ ADVANTAGE THERMO FINNIGAN (Method: Column:

Symmetry Shield RP18, 150×3.0 mm, 3.5 µm, Eluent A: 0.05% TFA in Acetonitrile. Eluent B 0.058% TFA in H2O. Gradient 5% a 95% B at 0 min, 95% A 5% B at 30 min, 95% A 5% B at 36 min, 5% a 95% B at 36.5 min, 5% a 95% B at 42 min. Flow: 0.6 ml/min, Temp. 40° C. Injection vol: 4 µL. Diluent: Acetonitrile).

HPLC Equipment: WATERS 2695 (Method: Column: WATER XBRIDGE C18, 5 µm, 150 mm*4.6 mm. Eluent A: pH 9.0 Ammonium (50 mM) Buffer, Eluent B: Acetonitrile:Methanol 1:1. Gradient: 10% B at 0 min, 100% B at 30 min, 10% B at 30.1 min, 10% B at 36 min. Flow: 1 ml/min, Temp. 40° C. Injection vol: 20 µL. Diluent: Acetonitrile:$H_2O$ (8:2)).

Unless Otherwise Stated, Starting Materials were Obtained from Commercial Sources Such as (but not Limited to) Sigma-Aldrich and Acros.

Example 1a: Preparation of N-(4-fluorobenzyl)-1-methylpiperidin-4-amine (Starting Material 1 (SM1)

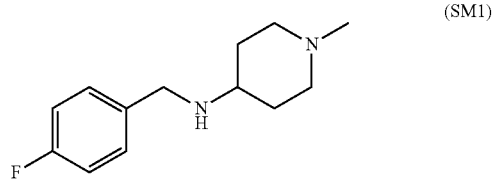 [SMILES: CN1CCC(NCc2ccc(F)cc2)CC1]

(SM1)

Sodium triacetoxyborohydride (6.5 kg) was added over 1.5 h to a solution of N-methylpiperid-4-one (3.17 kg) and 4-fluorobenzylamine (3.50 kg) in methanol (30 L) maintaining the temperature under 27° C. The reaction mixture was stirred for 15-24 h at 20-40° C. The residual amine was checked by HPLC gel chromatography (4-fluorobenzylamine: <5%). A solution of 30% sodium hydroxide (12.1 kg) in water (15-18 kg) was added over 1-2 h maintaining the temperature under 20-30° C. Methanol was distilled off to a residual volume of 26 liters. Ethyl acetate was added (26 L), the solution was stirred for 15-30 min, the phases were separated over 15-20 min and the lower aqueous phase was discarded. Ethyl acetate was distilled under reduced pressure from the organic phase at 70-80° C. At this stage the residue was mixed with a second crude batch prepared according to this method. The combined products were then distilled at 139-140° C./20 mbar to yield 11.2 kg product (>82%).

Example 1b: Scaled-Up Preparation of SM1

The reaction step was performed in three batches, which were each manufactured on the same scale as described below and the resulting products combined for further use in the next step.

N-Methylpiperidone (33.0 kg) and 4-fluorobenzylamine (35.4 kg) were dissolved in methanol (220.1 kg) at 15-19° C. (exothermic dissolution), and a suspension of 5% palladium on charcoal (1.2-1.3 kg) in methanol (17-18 kg) was added under nitrogen and the line rinsed with methanol (5.6 kg). The bulk was heated to 20-30° C. and hydrogenated at the same temperature and ~5 bar until the hydrogen absorption stopped (~12 h). The residual starting material was checked by GC, and the bulk was clarified on a Lens filter equipped with a thin CELTROX pad and 2×G92 filter papers. The line was rinsed with methanol (9.8 kg). The solvent was distilled under reduced pressure (265-60 mbar; 35-40° C.) and the oily residue was purified by fractional distillation under vacuum at ~135-140° C. at 8-0.5 mbar. Impure fractions of the three batches were combined and redistilled.

Total yield (combined three batches and redistilled fractions): 147.4 kg (78.1%).

Example 2a: Preparation of (4-isobutoxyphenyl)methanamine (Starting Material 2 (SM2))

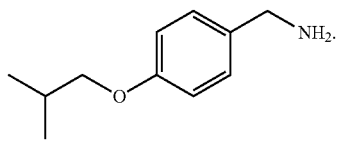

(SM2)

Preparation of

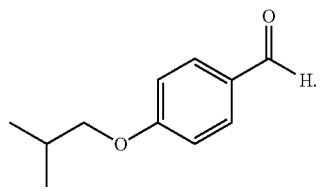

4-Hydroxybenzaldehyde (4.0 kg) and ethanol (20 L) were added to a solution of isobutyl bromide (9.0-10 kg) in ethanol (15-18 L). Potassium carbonate (13-14 kg) was added and the suspension was refluxed (74-78° C.) for 5 days. The residual 4-hydroxybenzaldehyde was checked by HPLC (<10%). The suspension was cooled to 20° C. and used in the next step.

Preparation of

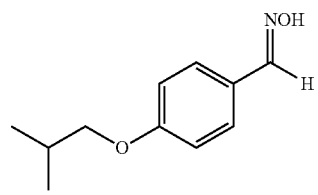

Hydroxylamine (50% in water, 8-9 kg) was added to the aldehyde (4-isobutoxybenzaldehyde) obtained in the previous step (174 L, 176 kg) and ethanol (54 L). The suspension was refluxed (77° C.) for 3-5 h. Unreacted residual aldehyde was checked by HPLC (<5%). The suspension was cooled to 30° C., filtered and the filter was washed with ethanol (54 L). The solution was concentrated by distillation under reduced pressure at 30° C. to a residual volume of 65-70 liters. The solution was cooled to 25° C. and water (110 L) was added. The suspension was concentrated by distillation under reduced pressure at 30° C. to a residual volume of 100-105 liters. Petroleum ether (60-90 fraction, 90-100 L) was added and the mixture was heated to reflux (70-80° C.). The solution was cooled to 40° C. and crystallization was initiated by seeding. The suspension was cooled to 0-5° C. and stirred for 3-6 h. The product was centrifuged and the cake was washed with petroleum ether (60-90 fraction, 32 L). The wet cake was dried at about 40° C. to yield 15-18 kg product (60-70%) used in the next step.

Preparation of

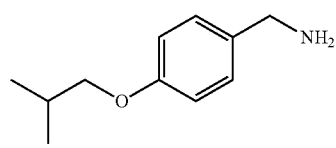

The product from the previous step (15.7 kg) was dissolved in ethanol (120-130 L). Acetic acid (8.0-9.0 kg) and palladium on charcoal 5% wet (1.0-1.5 kg) were added. The oxime was hydrogenated at 22° C. and 1.5 bar for 3-6 h. Consumption of oxime was checked by HPLC. The catalyst was filtered and the solvent was distilled under reduced pressure at 36° C. to a final volume of 30-32 L. Ethyl acetate (60-70 L) was added and the mixture was heated to reflux (75° C.) until dissolution. The solution was cooled to 40-50° C. and the crystallization was initiated by seeding. The suspension was cooled to 0-10° C. and stirred for 2-4 h. The product was centrifuged and the cake was washed with 2 portions of ethyl acetate (2×0.8 L). The wet cake was dried at a temperature of about 40° C. to yield 8-9 kg (40-50%). The obtained material is treated with sodium hydroxide in toluene to generate about quantitative yield of SM2.

Example 2b: Alternative Preparation of SM2

Preparation of

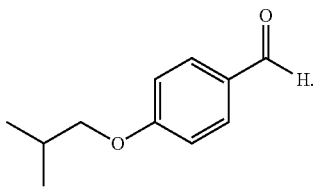

The reaction step was performed in two batches. 4-Hydroxybenzaldehyde (141 kg) was dissolved in dimethylformamide (335 kg) at 15-25° C., then solid potassium carbonate (320-330 kg) and potassium iodide (19-20 kg) were added portion wise at <30° C. and the suspension was heated up to 70-90° C. The temperature of the condenser was fixed to 0-10° C. and isobutylbromide (315-320 kg) was added to the suspension over 4-6 h at 75-90° C. At the end of the addition, the mixture was stirred for 2-4 h at 75-90° C. and residual starting material was checked by HPLC. The suspension was cooled to 20-30° C., diluted with 100% ethanol (500-550 kg, denatured with isopropanol), stirred for 15-30 min at 20-30° C. and centrifuged (3 loadings) to remove the excess of carbonate and potassium bromide. The line and the cake were washed with 100% ethanol (2×32 kg/loading). The solution is used as such in the next step.

Example 2c: Preparation of SM3

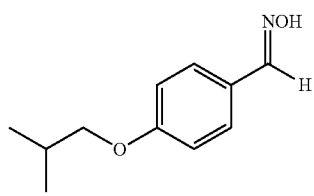

To the aldehyde solution resulting from Step b, 50% hydroxylamine in water (110-120 kg) was added at room temperature over ~0.5 h (the addition is slightly exothermic), the line washed with ethanol (8-10 kg), then the bulk was heated up to 70-77° C. and stirred at this temperature for 2-4 h. The bulk was concentrated under reduced pressure (250-120 mbar, 45-55° C.) to ~850-900 L, the residue quenched with water (900-1000 kg) at 45-55° C. and the residual ethanol distilled under vacuum (270-150 mbar, 45-55° C., residual volume=1466 L). The bulk was diluted with petrol ether 60-90 (500-600 kg) and heated at reflux (~60° C.) to reach complete dissolution (~20 min, visual check). The solution was cooled down to 5-15° C. (crystallization occurs at T=~25-30° C.) over ~5-6 h. After 1-2 h stirring at 10° C., the mixture was cooled to 0-5° C. and stirred at this temperature for 2-4 h. The bulk was centrifuged (3 loadings) and the cake washed with petroleum ether (2×23 kg/loading), then dried under reduced pressure at 40° C. to afford the crude oxime (210-215 kg).

Recrystallization:

The crude product (212 kg) was dissolved in hexane (640-650 kg) at 15-25° C. and the suspension heated up to ~60-70° C. Charcoal (6-10 kg) in hexane (26-30 kg) was added and the suspension was stirred for 0.5-1.5 h. After filtration (the filter was washed with 30-40 kg hexane), the solution was cooled to crystallisation temperature (~50-60° C.), and the mixture was stirred for 1-2 h at this temperature. The suspension was cooled to 10-15° C. After stirring for ~2-4 h at that temperature, the bulk was centrifuged (3 loadings) and the cake washed with cold hexane (2×13 kg/loading), then dried under reduced pressure at 40° C.

Yield oxime: 190-200 kg (80-90% over the two steps)

Example 2d: Preparation of 4-iso-butyloxybenzylammonium Acetate

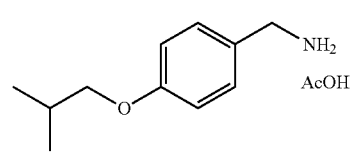

The oxime (198 kg) from Step c was dissolved in ethanol (1140-1150 kg, denatured with isopropanol). Raney nickel catalyst (25-30 kg) was washed with ethanol (690-700 kg) until the water content by Karl Fischer was below 3000 ppm, then the anhydrous Raney-Nickel was added under nitrogen to the oxime solution, the line washed with ethanol (62 kg) and the suspension cooled down to 0-10° C. Ammonia gas (220-230 kg) was added under vacuum over ~5-7 h (the addition is exothermic). Then the suspension was heated to 40-50° C. The internal pressure increased to ~3-5 bar. The bulk was hydrogenated at 40-50° C. and 3-5 bar until the hydrogen absorption stopped (~6-10 h) and the end of reaction was checked by HPLC. The suspension was cooled to 10-20° C., the excess of ammonia was removed, and the bulk clarified by filtration over Celtrox (4-5 kg). The line was washed with ethanol (317 kg). The solvent was distilled under reduced pressure (150-10 mbar, 40-50° C.) and the residue dissolved in toluene (700-800 kg) at ~40° C. The solution was transferred to a new reactor (previous reactor washed with 50-60 kg toluene), and cooled to 20-30° C. Acetic acid (AcOH, 60-70 kg) was slowly added (exothermic reaction) at 20-30° C. and the bulk heated during 20-40 min to ~90-100° C. until complete dissolution was reached. The solution was cooled rapidly to 70-80° C. and seeded with amino acetate product (50 g). The suspension was stirred at the crystallization temperature for 30-60 min, cooled to 0-10° C. and stirred for ~1-2 h at this temperature. The bulk was centrifuged (3 loadings) and the cake washed with cold toluene (2×48 L/loading) and finally dried under vacuum at (9-16 mbar) at ~50° C. for 28 h.

Yield: 200-210 kg (80-90%)

Example 2e: Alternative Preparation of SM2 (4-iso-butyloxybenzylamine)

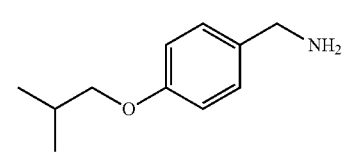

A solution of the aminoacetate (269 kg) from Step c in water (400-500 kg) was basified with 30% sodium hydroxide solution (300-310 kg) to pH 14 at 20-25° C. Then the amino base product was extracted with toluene (900-1000 kg) at 40-50° C. by stirring for 15-30 min. The bulk was decanted during 15-30 min at 40-50° C.; if necessary the pH was adjusted to >12 with additional 30% NaOH, then the layers were separated. The organic layer was washed with water (359 kg), then concentrated under vacuum (200-20 mbar) at 45-50° C. to give the aminobase as an oily residue.

Example 2f: Alternatively 4-iso-butyloxybenzylamine (SM2) and 4-iso-butyloxybenzylamine Acetate (SM2b) are Prepared According to Following Scheme

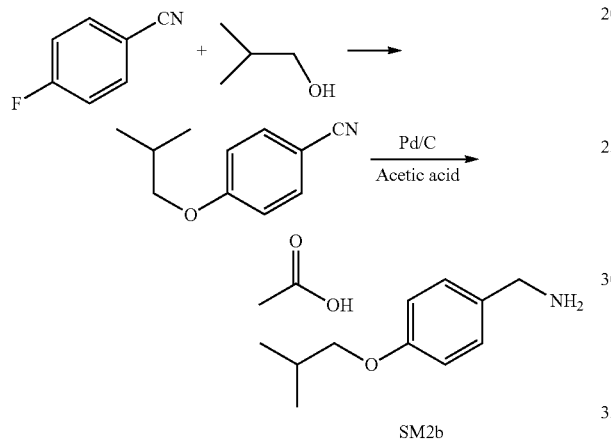

SM2b

To potassium tertbutoxide (KOtBu, 1.4 eq, 77.7 g) 350-400 ml methyl tert-butylether (MTBE) were added under a nitrogren atmosphere. The mixture was stirred at ambient temperature and isobutanol (1.6-2.00 eq, 59-74.2 g) was added during 2 h while keeping a temperature of about 50-60° C., and thereafter heated for about 1 h at about 50-60° C. A solution of 4-fluorobenzonitrile (1 eq, 60 g) in about 60-80 ml MTBE under anitrogen atmosphere were added dropwise to the reactor containing the KOtBu while a temperature of less than about 55-60° C. was maintained, and thereafter the mixture kept at about 50-60° C. for about 1-2 h. The mixture was cooled to about 10-15° C. and 200 ml water added while a temperature of about less than 20° C. was maintained. The mixture was allowed to settle and phase separation occurred, and the aqueous phase separated. The organic phase was washed with water (2×120 ml) and the solvent distilled off. Thereafter 300-400 ml of methanol was added to the residue at ambient temperature, and the mixture transferred to an autoclave. Acetic acid (0.8 eq-1.2 eq, 23.8-35.7 g) and palladium (Pd) catalyst type JM 39 5.5 w % Pd WNASS (0.001 eq-0.01 eq, 2.1-21.0 g) (commercially available from Johnson and Matthey) were added under nitrogen washing together with methanol (15-20 ml). The mixture was heated to about 45-50° C. and hydrogenated at 1-5 bar H₂ for 3-8 h and thereafter allowed to cool to ambient temperature. The mixture was filtered and the solvent was removed and the remaining residue washed with toluene, and the product dried to give SM2b.

Example 2g: Alternatively 4-iso-butyloxybenzylamine (SM2) and 4-iso-butyloxybenzylamine Acetate (SM2b) are Prepared According to Following Scheme

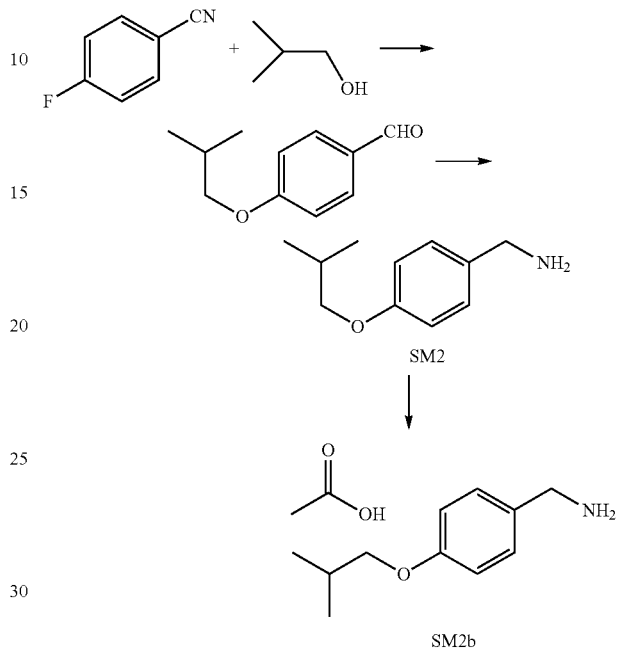

KOH (1.36 g, 24.2 mmol, 3 eq) was dissolved in water (1.4 ml) and added to the solution of 4-fluorobenzaldehyde (1.0 g, 8.1 mmol, 1 eq). Isobutanol (0.66 g, 8.9 mmol, 1.1 eq) and tetrabutyl ammonium hydrogensulfate (TBAH, 0.27 g) in toluene (7 ml). The reaction mixture was vigorously stirred at 50-52° C. overnight and thereafter diluted with water (5 ml), dried and concentrated in vacuo to give 0.877 g of crude product. The crude product was purified by column chromatography using ethyl acetate: heptane to give 0.6 g of 4-isobutoxy benzaldehyde. 4-Isobutoxy benzaldehyde can thereafter be converted to SM2 and SM2b respectively using the procedure outline in example 2b.

Example 2i: Alternatively 4-iso-butyloxybenzylamine (SM2) and 4-iso-butyloxybenzylamine Acetate (SM2b) are Prepared According to Following Scheme

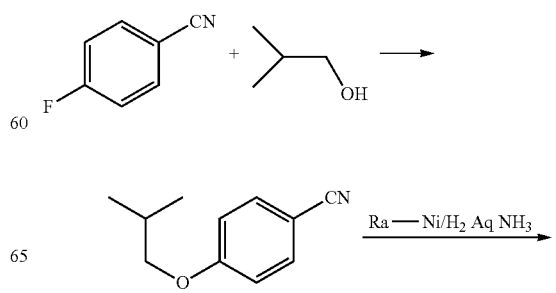

-continued

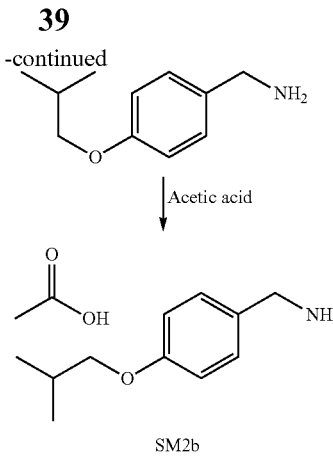

SM2b

To 60% sodium hydride in mineral oil (24.8 g-33.00, 1.5 eq-2.0 eq) suspended in THF (450-500 ml), heated to 50-60° C. isobutanol (45.9 g-61.2 g, 1.5 eq-2.0 eq) was added over 30-60 min and thereafter stirred for 1 h. 4-Fluorobenzonitrile (50 g, 1 eq) in THF (30 ml) was added over 1-2 h followed by stirring for about 2-3 h. The mixture was cooled to room temperature and brine (10%, 300 ml) was added. The reaction mixture was extracted with MTBE (300 g), organic layer was separated, washed with water (100 ml), and evaporated to give 4-isobutoxybenxonitrile.

Alternatively potassium tert-butoxide (KOtBu, 55.5 g-92.5, 1.2-2.0 eq) was suspended in MTBE (250-300 ml) and heated to 50-60° C. Isobutanol (36.3-63.0 g, 1.2-2.0 eq) was added over about 30-60 min. After 1 h a solution of 4-fluorobenzonitrile (50 g, 1 eq) in MTBE (50 ml) was added over about 1 h and the flask was washed with MTBE (10 ml). The mixture was stirred overnight (about 12-18 h) at a temperature of 50-60° C. and thereafter cooled to room temperature and followed by addition of deionized water (200 ml). The layers were separated and solvent (200 g) distilled off from the organic layer under vacuum. MeOH (310-350 ml) was added and solvent (100-150 g) distilled off under vacuum to give a solution, which was diluted with aqueous ammonium chloride (NH$_4$Cl) and extracted with ethyl acetate. The separated organic layer was dried over sodium sulphate, filtered and concentrated to afford crude product which upon column chromatography afforded pure 4-isobutoxybenzonitrile as an oil.

To 4-isobutoxybenzonitrile as obtained by any of the described methods (20 g, 1 eq) dissolved in MeOH (75 ml), aqueous 25% NH$_3$ (25.4 g, 3 eq) and wet activated Raney-Nickel (about 3 g) were added. The mixture was hydrogenated at 4-5 bar and 50° C. for 5 h. and thereafter cooled to RT and the catalyst filtered off. The solvent (about 70 g) was distilled off, followed by dilution with toluene (150 ml), which gave separated layers. About 50 ml solvent was distilled off at 50° C. from the organic layer and acetic acid (AcOH, 4.7-7.8 ml, 0.8 eq-1.2 eq) was added over 15-30 min at 50° C. The resulting suspension was cooled to about 20° C. and stirred for 2-4 h and thereafter filtered and washed using toluene (10-20 ml). Evaporation at 40° C., <50 mbar, during 12 h gave the 4-iso-butyloxybenzylamine acetate (SM2b) as a white powder in about 70-80% yield. The product was determined to have a high performance liquid chromatography (HPLC) purity of about 99.5%.

Example 3a: Preparation of Pimavanserin Via Activation of Dimethyl Carbonate (DMC)

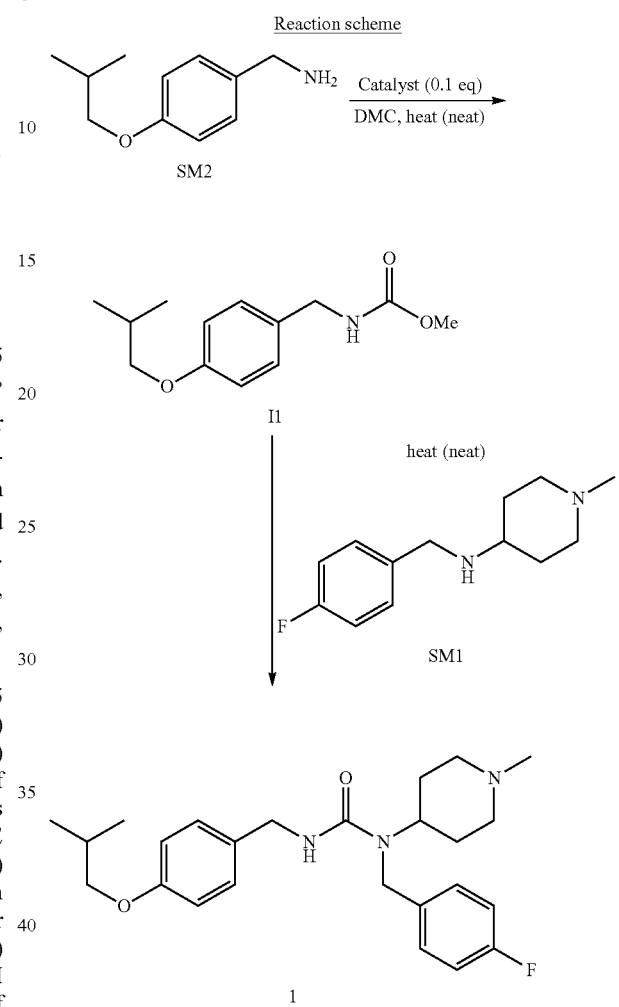

Route 1: SM2 (179 mg, 1.00 mmol) and catalyst (Zr(O$^t$Bu)$_4$/2-hydroxypyridine 0.10 equiv.) were added to DMC (99.0 mg, 1.1 equiv.). Zr(O$^t$Bu)$_4$ is short for zirconium tetra tertiary butoxide. The mixture stirred for about 12 h at 80° C. followed by addition of SM1 (1.10 equiv.) and catalyst (0.10 equiv.). The mixture was stirred at 120° C. for about 24 h. Yield: 22% pimavanserin Route 2: was performed in accordance with route 1 replacing the route 1 catalyst by Sodium tert-butoxide (NaO$^t$Bu, or optionally potassium tert-butoxide)) and stirred at 120° C. for about 72 h. Yield: 20% pimavanserin. Optionally Route 2 was performed using 18-crown-6 as co-catalyst (0.1 equiv.). The crown ether was added to SM1 dissolved in dissolved in toluene (0.3 ml, 2M). Yield: 47% pimavanserin.

Optionally I1 may be isolated, and has for example been isolated from route 1 in about 81% yield. I1 was characterized by NMR: $\delta_H$ (400 MHz, dmso-d6) 7.58 (t, J=6.2 Hz, 1H), 7.15 (d, J=8.6 Hz, 2H), 6.86 (d, J=8.6 Hz, 2H), 4.09 (d, J=6.2 Hz, 2H), 3.70 (d, J=6.5 Hz, 2H), 3.53 (s, 3H), 2.04-1.94 (m, 1H), 0.96 (d, J=6.7 Hz, 6H).

Example 3b: Preparation of Pimavanserin Via Activation of Dimethylcarbonate (DMC)

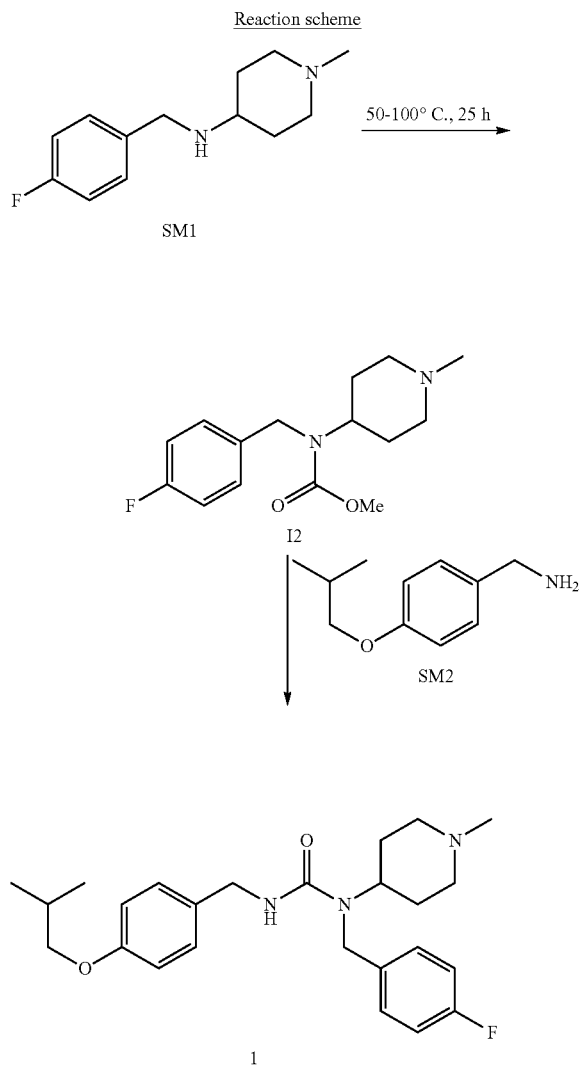

SM1 (222 mg, 1.00 mmol) and catalyst (Zr(O'Bu)₄/2-hydroxypyridine 0.10 equiv.) were added to DMC (99.1 mg, 1.10 equiv.). The mixture was stirred for about 25 h at 50-100° C. followed by addition of SM2 (1.10 equiv.) and co-catalyst (0.10 equiv.). The mixture was stirred at 100° C. for about 25 h to give pimavanserin.

Example 3c: Preparation of Pimavanserin Using Diphenyl Carbonate

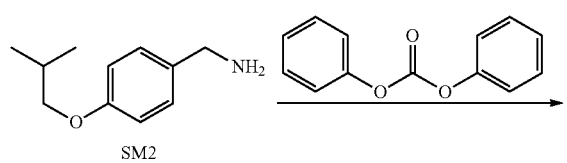

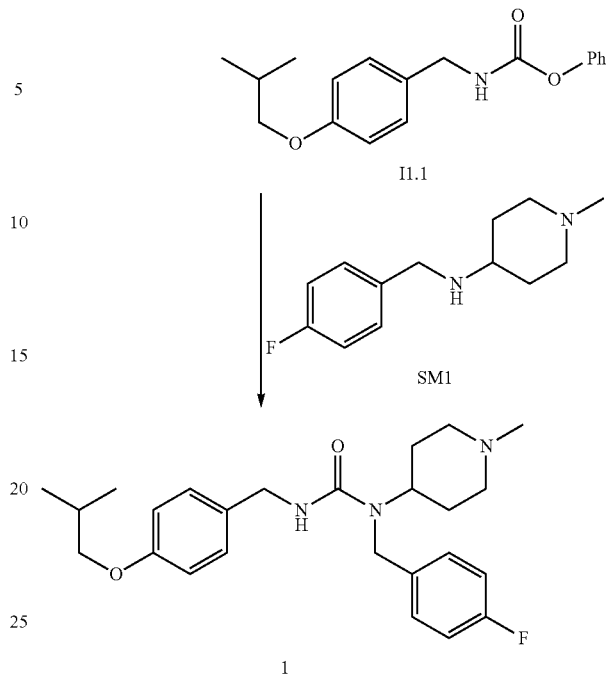

Diphenyl carbonate (14.9-20.31 g, 1.1-1.5 eq) in toluene (35-50 ml) was stirred and heated to about 35° C. until a solution was formed. SM2 (11.3 g) in toluene (about 90 ml) was added over 3 h at a temperature of about 30-40° C. The mixture was maintained at about 30-40° C. for about 14-24 h in order to give phenyl (4-isobutoxybenzyl)carbamate (I1.1) in 99%, and some amounts of SM2 (less than 1.0 a %) (checked by HPLC).

The mixture was cooled to 0° C. and sodium hydroxide (2.25 g) in deionized water (40 g) was added, and the temperature kept below 10° C. Upon completed addition the mixture was stirred and thereafter allowed to settle and the aqueous layer was removed. The organic layer was heated to about 40° C., and hydrochloric acid (0.5 vol %, about 50 ml) was added, and thereafter the mixture maintained for about 10 min before settling for 15 min. The aqueous layer was removed and the organic layer washed with deionized water (20 g), stirred and maintained at about 40° C. before settling for 15 min. Again the aqueous layer was removed and the solvent distilled off from the organic layer under vacuum. The obtained residue was washed with 95/5 (w %/w %) heptane and ethyl acetate. The mixture was maintained at an elevated temperature (about 50° C.) before cooling the resulting suspension to 0-10° C. The suspension was maintained for 3-5 h before obtaining I1.1 by filtration. The crude I1.1 was washed with heptane and dried to provide 17.8 g (95%) I1.1.

$^1$H NMR of I1.1 (CDCl$_3$): δ 1.0 (d, 6H), 2.1 (m, 2H), 3.7 (d, 2H), 4.3 (d, 2H), 5.2 (b, 1H), 6.8 (d, 2H), 7.1 (d, 2H), 7.2 (m, 1H), 7.22 (m, 2H), 7.8 (m, 3H);

Pimavanserin is obtained as described in examples 4e, 4f, and 4g.

Example 3d: Preparation of Pimavanserin Using Diphenyl Carbonate

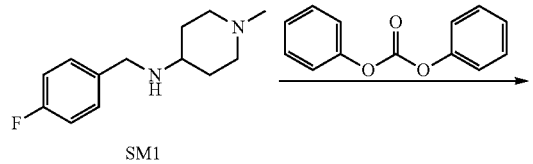

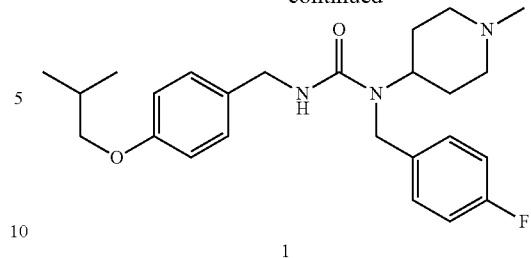

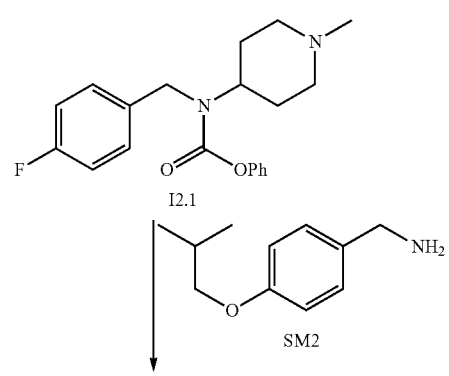

SM2 was added over 10 min to a mixture of diphenyl carbonate (DPC, 1.1-1.5 eq) in toluene (20 eq). The mixture was maintained at room temperature for about 3-5 h in order to give phenyl (4-fluorobenzyl)(1-methylpiperidin-4-yl)carbamate (I2.1) in 98%, and some amounts of 1,3-bis(4-isobutoxybenzyl)urea. To the mixture potassium carbonate (0.5-1.0 eq) and SM1 (1 eq) were added and heated to 65-80° C. for 5 h followed by cooling to 50° C. and addition of sodium hydroxide (1.1 eq) in water, followed by additional water. The organic layer was separated and solvent was distilled off and heptane:ethyl acetate (95:5) was slowly added followed by cooling to room temperature, maintained at about 3 h and thereafter filter washed with heptane:ethyl acetate (95:5) to give pimavanserin in a yield of about 90% and about 99% purity. $^1$H NMR (CDCl$_3$) of I2.1: δ 1.6-2.0 (m, 6H); 2.2 (s, 3H); 2.8 (m, 2H); 4.0 (br m, 1H); 4.5 (br s, 2H), 7.0-7.40 (m, 9H).

The step to obtain pimavanserin can be carried out analogous to the procedures described in examples 4e, 4f, and 4g.

Example 4a: Preparation of Pimavanserin Using Methyl Chloroformate

Reaction scheme

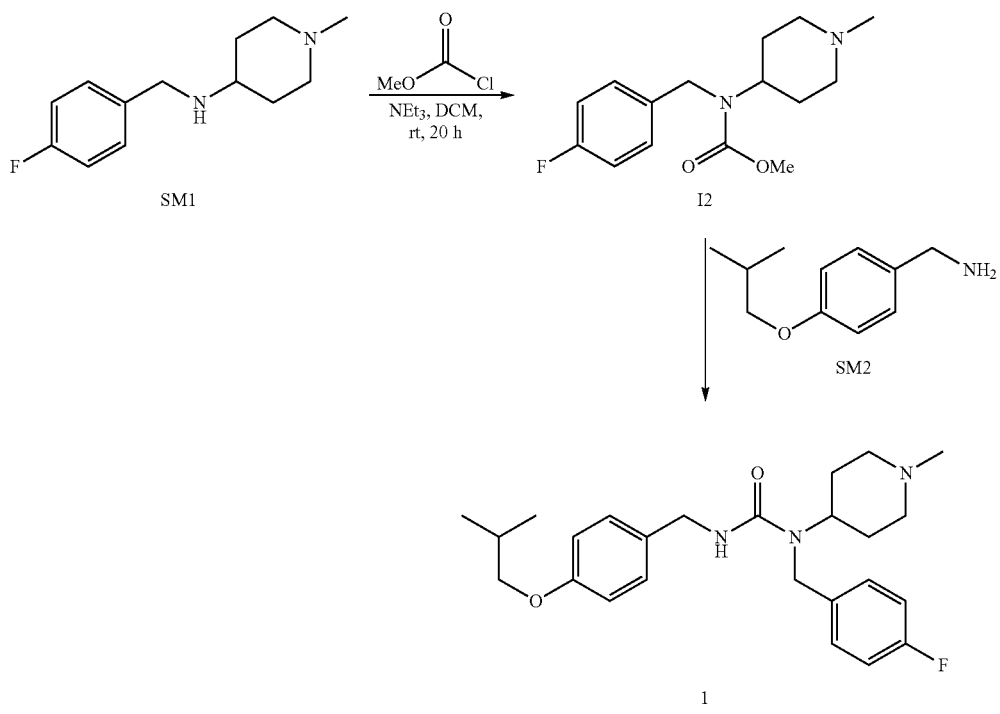

Methyl chloroformate (0.538 ml, 7.00 mmol) was added dropwise to a stirred solution of N-(4-fluorophenylmethyl)-1-methylpiperidin-4-amine SM1 (1.11 g, 5.00 mmol) and triethylamine (0.842 ml, 6.00 mmol) in dichloromethane (20 ml). After 48 h, LCMS analysis indicated full consumption of starting materials. A 5 ml aliquot of the reaction mixture was washed with ice-cold sat. aq. NaHCO$_3$ (5 ml) and water (2×5 ml), dried (Na$_2$SO$_4$) and concentrated under reduced pressure. The crude residue was purified by chromatography on silica gel (1:19 methanol/dichloromethane) to give methyl (4-fluorophenylmethyl)(1-methylpiperidin-4-yl)carbamate (I2) (43 mg, 11%) as a colourless syrup; $\delta_H$ (400 MHz, dmso-d6) 7.28-7.24 (m, 2H), 7.15-7.10 (m, 2H), 4.39 (s, 2H), 3.73 (br s, 1H), 3.62 (br s, 3H), 2.75-2.70 (m, 2H), 2.09 (s, 3H), 1.83 (td, J=11.7, 2.3 Hz, 2H), 1.63 (qd, J=12.1, 3.9 Hz, 2H), 1.49-1.38 (m, 2H); δc (100 MHz, dmso-d6) 161.0, 156.2, 136.0, 128.6, 115.0, 54.8, 54.2, 52.4, 45.6, 45.5, 29.5; LCMS m/z 281.0 (M+H), 109.5, 98.1.

Intermediate I2 was used to obtained pimavanserin as described in Example 4a.

Example 4b: Preparation of Pimavanserin Using Methyl Chloroformate

Methyl (4-isobutoxybenzyl)carbamate was prepared by adding methyl chloroformate (about 1 eq) to SM2 (1 eq) in toluene during 5 h followed by heating at 40° C. followed by layer separation. The solvent was distilled off from the organic layer and heptane:ethyl acetate (95:5) was added slowly to give the methyl (4-isobutoxybenzyl)carbamate (I1) after filtering and washing. Yield: about 80%. $^1$H NMR CDCl$_3$: δ 1.0 (d, 6H); 2.0 (m, 1H); 3.7 (s, 3H); 4.28 (s, 3H); 4.3 (s, 2H); 4.9 (br, 1H); 6.8 (d, 2H); 7.2 (d, 2H).

Methyl (4-isobutoxybenzyl)carbamate (1 eq) was added to methyl (4-fluorobenzyl)(1-methylpiperidin-4-yl)carbamate (SM1, 1 eq) in toluene and triethylamine (1.5 eq) and heated to 110° C. for 20 h. After conventional phase separation work-up pimavanserin was obtained in about 4-5% yield.

Example 4c: Preparation of Pimavanserin Using 2,2,2-trifluoroethyl chloroformate and bis (2,2,2 trifluoroethyl) carbonate 2,2,2-trifluoroethyl (4-isobutoxybenzyl) carbamate was prepared by treating SM2 with a mixture of bis (2,2,2 trifluoroethyl) carbonate and 2,2,2-trifluoroethyl chloroformate (prepared as described in Tetrahedron 67 (2011) 3619-3623) to obtain 2,2,2-trifluoroethyl (4-isobutoxybenzyl) carbamate in about 80% yield. SM2 (1.0 g, 6 mmol, 1 eq,) and the mixture of bis (2,2,2 trifluoroethyl) carbonate and 2,2, 2-trifluoroethyl chloroformate (1.32 g, ~6 mmol, ~1 eq.) and DIPEA (N,N-diisopropylethylamine, 1 ml) in acetonitrile (3 ml) were heated at 70-75° C. in a sealed tube for 2 h and allowed to cool to room temperature. Xylene (0.45 ml) was added to reaction mixture, which was evaporated to dryness to give 1.66 g of 2,2,2-trifluoroethyl (4-isobutoxybenzyl) carbamate. The crude product was dissolved in acetonitrile (3 ml) and SM1 (1.49 g, 7 mmol, 1.2 eq.) and DBU (1,8-Diazabicyclo[5.4.0]undec-7-ene, 0.51 g, 0.5 eq.) added. The mixture was heated at 70-75° C. in a sealed tube for 4 h and allowed to cool to room temperature. Chloroform (10 ml) was added to the reaction mixture and organic was washed with water (3×10 ml), dried and evaporated to dryness to give 2.83 g of crude pimavanserin. After triturating the crude product with n-heptane the purity increased to 70.5 area %. Yield: about 73%.

Example 4d: Preparation of Pimavanserin Using p-nitro-phenyl Chloroformate

Analogous to Examples 4b and 4c 4-nitrophenyl (4-isobutoxybenzyl)carbamate was prepared in a yield of about 80% and thereafter mixed with SM1 and converted to pimavanserin using a procedure similar to the procedure described in Example 4b. Pimavanserin was obtained in about 46% yield and the by-product 1,3-bis(4-isobutoxybenzyl)urea was observed in substantive amounts.

$^1$H NMR (CDCl$_3$): δ 1 (d, 6H), 2.05 (m, 1H), 3.7 (d, 2H), 4.38 (d, 2H), 5.35 (b, 1H), 6.88 (d, 2H), 7.24 (d, 2H), 7.30 (d, 2H), 8.22 (d, 2H).

Example 4e: Preparation of Pimavanserin Using Phenyl Chloroformate

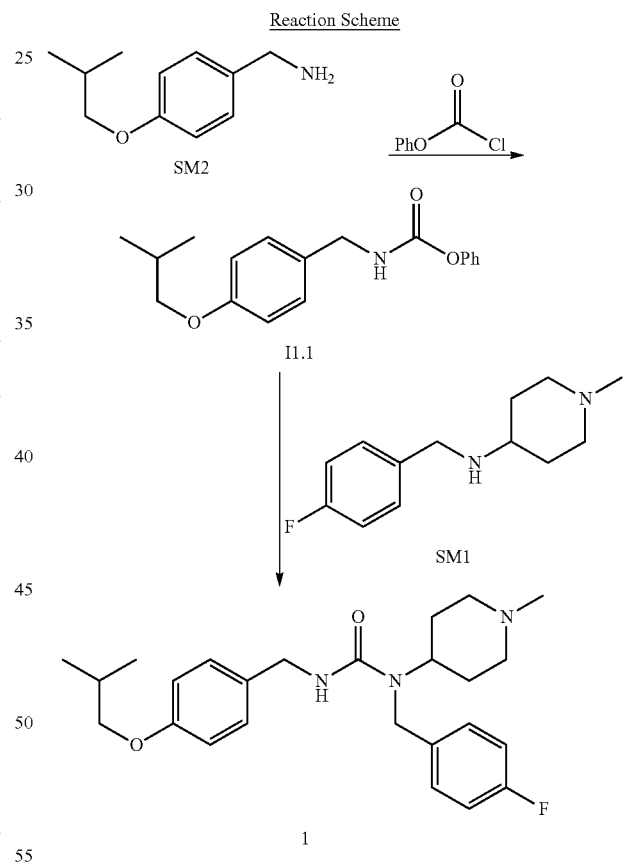

A solution of 4-isobutoxybenzyl amine (1 g, 5.6 mmol, 1 eq) in THF or toluene (5 ml) was added to a flask containing potassium carbonate (1.5 eq) and phenyl chloroformate at room temperature and stirred for 1 h. The mixture was extracted with EtOAc (ethyl acetate), and the organic layer washed with NH$_4$Cl solution followed by water, dried over sodium sulfate and concentrated to afford pure product I1.1 as white solid (optionally I.1.1 may be isolated as described in the following section). Optionally I1.1 does not need to be isolated before next step.

Yield: 1.6 g 95%

Optionally I1.1 may be prepared by free-basing SM2b by dissolving SM2b in water and adding about 1 eq of potassium carbonate followed by toluene and thereafter adding phenyl chloroformate over 5 h at a temperature of about 20° C. and optionally isolating I1.1 by heating to 40° C. followed by layer separation, distillation of the organic phase and slow addition of heptane:ethyl acetate (95:5) to give I1.1 after filtration and washing. Optionally, the free-basing of SM2b may be done by sodium hydroxide as base.

$^1$H NMR of I1.1 (CDCl$_3$): δ 1.0 (d, 6H), 2.1 (m, 2H), 3.7 (d, 2H), 4.3 (d, 2H), 5.2 (b, 1H), 6.8 (d, 2H), 7.1 (d, 2H), 7.2 (m, 1H), 7.22 (m, 2H), 7.8 (m, 3H);

LC/MS of I1.1—Column: Symmetry Shield RP18, 150× 3.0 mm, 3.5 μm, Eluent A: 0.05% TFA in Acetonitrile. Eluent B 0.05% TFA in H2O. Gradient 5% a 95% B at 0 min, 95% A 5% B at 30 min, 95% A 5% B at 36 min, 5% a 95% B at 36.5 min, 5% a 95% B at 42 min. Flow: 0.6 ml/min, Temp. 40° C. Injection vol: 4 μL. Sample preparation 1-3 mg in 1 ml Acetonitrile. Retention time: 21.85 min, M+H$^+$ =299.78 in toluene (453 g) was heated to 65° C. for 5 h and thereafter cooled to 50° C. and washed with a solution of sodium hydroxide (12.9 g, 1.1 eq) in water (348 g) followed by a solution of sodium hydroxide (6.4 g, 0.55 eq) in water (174 g), followed by 200 g water. Solvent was distilled off (about 300 g) and heptane:ethyl acetate (95:5) added slowly. The mixture was allowed to cool to room temperature (RT) during 1 h and thereafter stirred for another 3 h before filtered washing with heptane:ethyl acetate (95:5). The obtained product was dried for 12 h at 50° C. to give pimavanserin as a white powder in a yield of about 94% and a HPLC purity of 99.8 a %, 0.11 a % I1.1 and 0.07 a % 1,3-bis(4-isobutoxybenzyl)urea.

The obtained pimavanserin is thereafter converted into a tartrate salt, for example as described in Example 7.

Example 4g: Preparation of Pimavanserin Using Phenyl Chloroformate

The reaction scheme

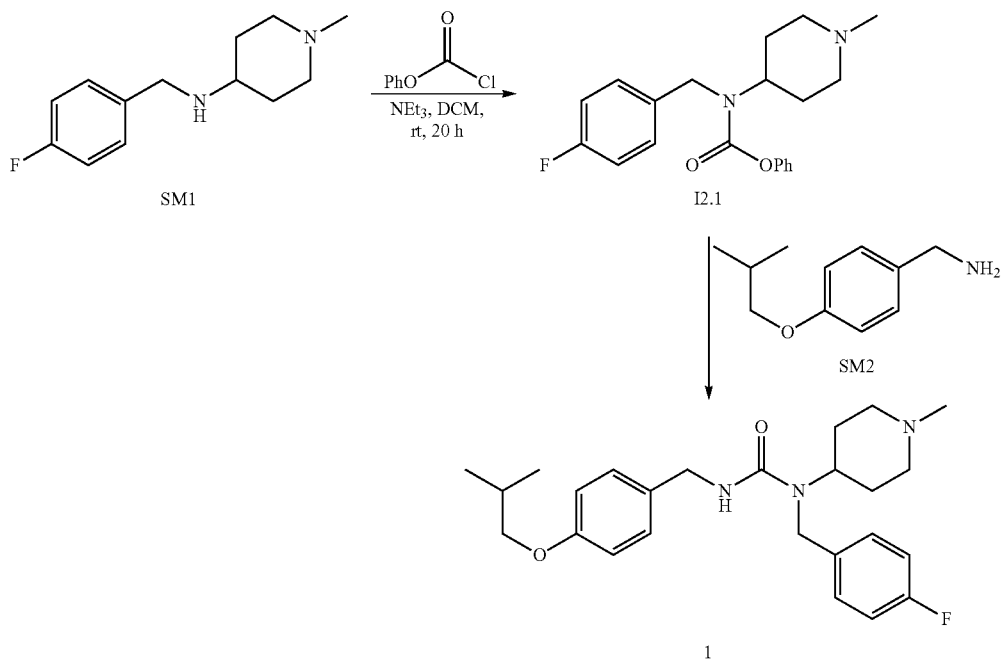

To a toluene solution of phenyl 4-isobutoxybenzylcarbamate (I1.1) (0.2 g, 0.67 mmol, 1 eq) and SM1 (0.15 g, 0.67 mmol, 1 eq) was added K$_2$CO$_3$ (0.2 g, 1.34, 2 eq), and the mixture was heated at 90° C. for 24 h. The reaction mixture was cooled to RT, washed with aq. NH$_4$Cl solution twice to remove phenol, dried over sodium sulfate and concentrated to afford pimavanserin as white solid.

Yield: 0.26 g. 92%.

Example 4f: Scaled-Up Preparation of Pimavanserin Tartrate Via phenyl (4-isobutoxybenzyl)carbamate I.1.1 (87 g, 1 eq) (prepared starting from 4-fluorobenzonitrile via SM2b (see example 2f and i) and further prepared in analogy with example 3c or 4e) and SM1 (54.7 g, 1 eq)

A solution of SM1 (1 g, 4.5 mmol, 1 eq) in toluene (5 ml) was added to a solution of phenyl chloroformate (0.8 g, 5 mmol, 1.1 eq) and potassium carbonate (1.25 g, 9 mmol, 2 eq) in toluene (3 ml). The reaction mixture was stirred for 1 h, then was washed with aqueous NH$_4$Cl solution. The solvent was evaporated to afford I2.1 as white solid. $^1$H NMR (CDCl$_3$): δ 1.6-2.0 (m, 6H); 2.2 (s, 3H); 2.8 (m, 2H); 4.0 (br m, 1H); 4.5 (br s, 2H), 7.0-7.40 (m, 9H); Yield: 1.4 g, 95%

Pimavanserin is obtained by heating the solution of intermediate I2.1 obtained above, with equivalent amount of SM2 in toluene in presence of 2 eq of potassium carbonate, followed by work-up as described in the previous examples.

Example 4h: Preparation of Pimavanserin Using dimethyl 2,2'-(carbonylbis(oxy))dibenzoate (bis(methylsalicyl)-carbonate) as Shown in the Following Scheme

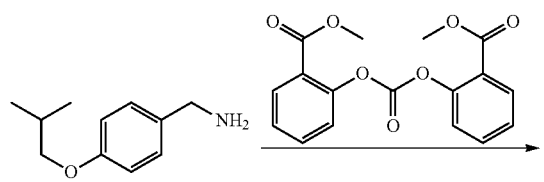

SM2

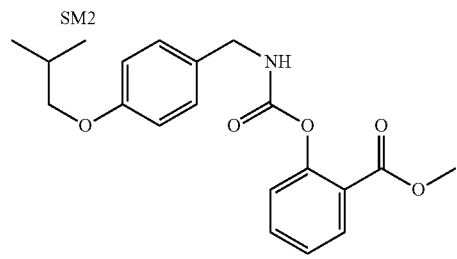

I2.3

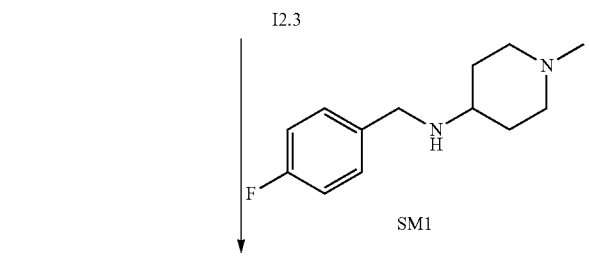

SM1

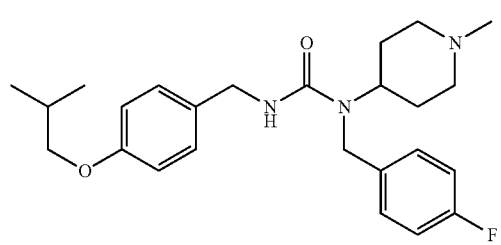

1

A mixture of SM2 (0.27 g, 1.5 mmol, 1 eq) and bis(methylsalicyl)-carbonate (0.50 g, 1.5 mmol, 1 eq) in dichloromethane (2 ml) was stirred at room temperature for 1.5 h to obtain carbamate 12.3. HPLC purity was 48%. The crude product was used as such for the next step and its yield estimated by HPLC as about 40% (area %).

The crude carbamate was dissolved in THF (4 ml) and SM1 (0.34 g, 1.5 mmol, 1 eq) was added, the mixture was heated to 40-50° C. and stirred overnight. The solvent was evaporated to give crude product which was purified by trituration with heptane (1 ml) to obtain 0.51 g pimavanserin in 65% purity (63% yield).

Alternatively, pimavanserin could also be prepared by reacting SM1 with bis (methyl salicyl) carbonate to give intermediate carbamate (I2.4) as shown in scheme. The intermediate carbamate was then treated with SM2 to obtain pimavanserin.

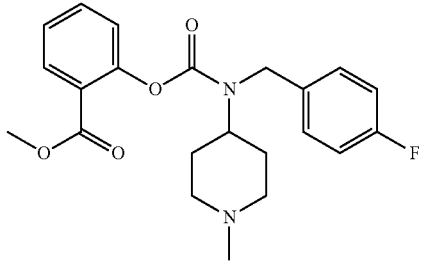

I2.4

Alternatively salicyl chloro 2,2'-(carbonylbis(oxy))dibenzoic acid could be used instead of bis (methyl salicyl) carbonate.

Example 5a: Preparation of Pimavanserin Using Carbonyldiimidazole (CDI)

Reaction Scheme:

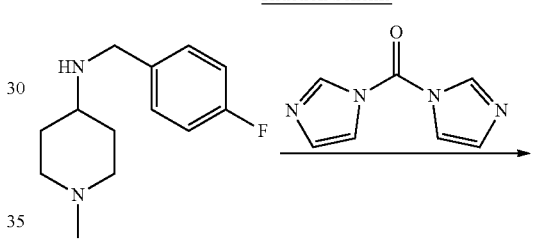

SM1

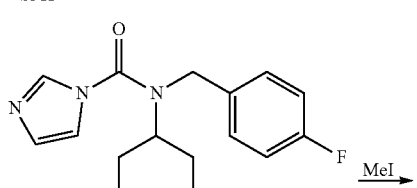

14

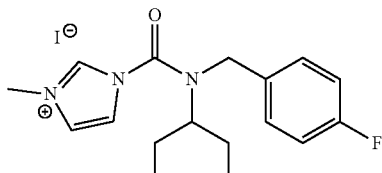

15

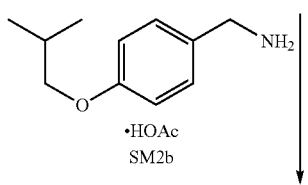

·HOAc
SM2b

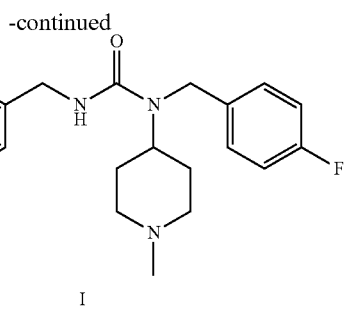

I

N-(4-fluorobenzyl)-1-methylpiperidin-4-amine (SM1, 120 mg) was treated by sodium hydroxide to give the freebase which optionally is isolated and thereafter added to CDT (excess such as 1.1-3 eq, such as 1.5-1.8 eq) in toluene (2 ml). Optionally I4 can be isolated. Optionally methyl iodide is used to convert 13 to 15 and thereafter the mixture was stirred for about 1 h at room temperature (rt) followed by addition of SM2b in toluene (about 1.1 eq.) and thereafter heated at 50° C. for about 15 h. The reaction resulted in pimavanserin being obtained in a quantitative yield (using 1.8 eq CDI) aqueous work up.

Optionally SM2b may be treated with a suitable acid such as HCl, optionally isolated, and thereafter proceeding in accordance with the procedure described. In order to obtain pimavanserin an additional trituration of crude pimavanserin was conducted.

Example 5b: Preparation of Pimavanserin Using Carbonyldiimidazole (CDI)

4-(2-Methylpropyloxy)-phenylmethylamine SM2 (822 mg, 4.59 mmol) was added in portions to a suspension of CDI (1.34 g, 8.25 mmol) in toluene (5 ml) at room temperature. The resulting mixture was stirred at room temperature for 4.5 h. The mixture was diluted with dichloromethane (45 ml), washed with aqueous 1M NaOH (25 ml) and water (2×50 ml), dried (Na$_2$SO$_4$) and concentrated to give N-(4-(2-methylpropyloxy)-phenylmethyl)imidazol-1-ylcarboxamide (I6) (1.20 g, 96%) as a colourless, amorphous powder; $\delta_H$ (400 MHz, CDCl$_3$) 8.09 (s, 1H), 7.35 (s, 1H), 7.29-7.18 (m, 2H), 7.02 (s, 1H), 6.92-6.83 (m, 2H), 6.52 (br s, 1H), 4.51 (d, J=5.4 Hz, 2H), 3.71 (d, J=6.5 Hz, 2H), 2.14-2.01 (m, 1H), 1.02 (d, J=6.7 Hz, 6H); $\delta_C$ (100 MHz, CDCl$_3$) 159.4, 148.9, 136.0, 130.6, 129.6, 128.8, 116.2, 115.1, 74.7, 44.7, 28.4, 19.4; LCMS m/z 274.5 (M+H), 107.2, 69.1. I6 can then be brought into contact with SM1 to obtain pimavanserin.

Optionally 4-(2-Methylpropyloxy)-phenylmethylamine (SM2) (90.0 mg, 0.502 mmol) was added in one portion to a suspension of CDI (146 mg, 0.900 mmol) in toluene (2 ml) at room temperature. The resulting mixture was stirred at room temperature for 1 h followed by addition of N-(4-fluorophenylmethyl)-1-methylpiperidin-4-amine (SM1) (116 mg, 0.522 mmol) and heating at 50° C. for 15 h. The mixture was diluted with dichloromethane (18 ml), washed with aqueous 1M NaOH (10 ml) and water (2×20 ml), dried (Na$_2$SO$_4$) and concentrated to give pimavanserin (206 mg, 96%) as a colourless, amorphous powder.

Reaction scheme

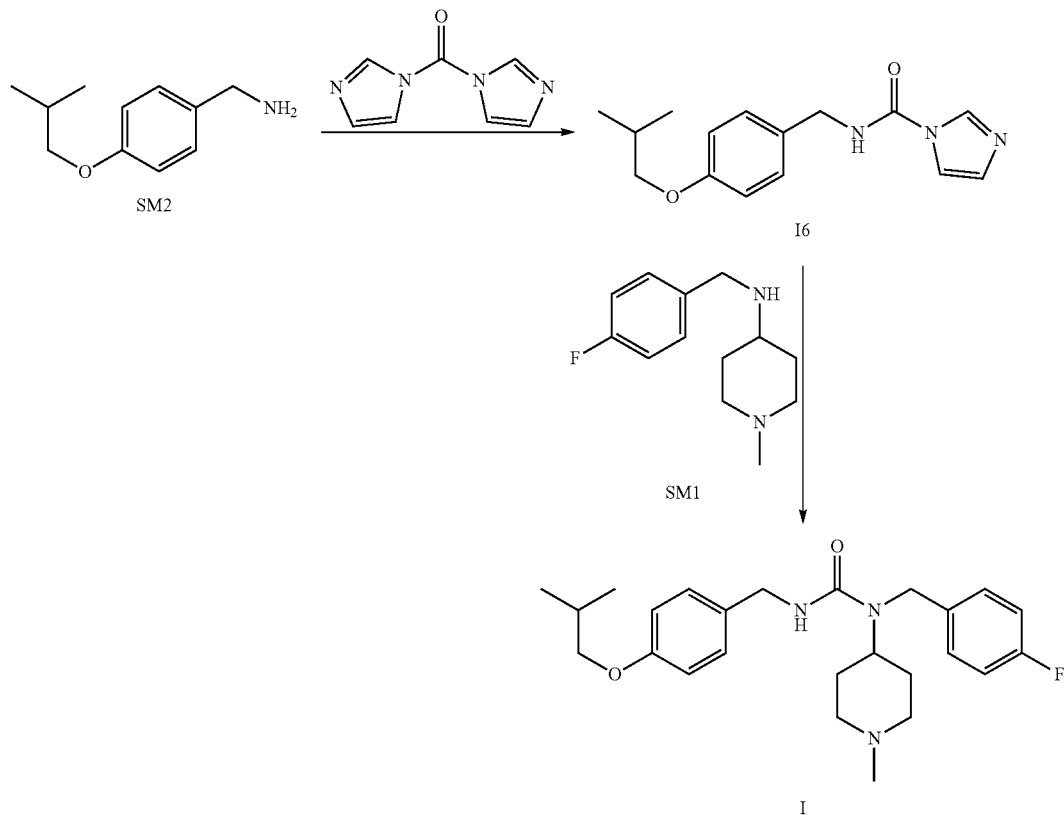

Example 5c: Scaled-Up Preparation of Pimavanserin Using Carbonyldiimidazole (CDI)

(4-isobutoxyphenyl)methanamine acetate (SM2b, 60 g, 1 eq) was dissolved in water (96 ml) and aqueous 30% sodium hydroxide (75 ml) followed by addition of toluene (300 ml). The mixture was heated to 55° C. and the layers separated. Toluene (105 ml) was added to the organic layer and solvent distilled off. THF (15 ml) was added and the solution cooled to 20° C. The obtained solution was added at a temperature 20-30° C. to CDI (49.2-57.4 g, 1.2-1.4 eq) in toluene (195 ml) and thereafter maintained for about 1.5 h. The mixture was cooled to 10° C. and deionized water (120 ml) added slowly. The organic layer was collected and washed with another portion of deionized water. The solvent (about 450-500 g) was distilled off and heptane:THF (9:1, 240 ml) added slowly. The precipitate was filter washed at 20° C. using heptane:THF (9:1, 60 ml). The obtained product I6 was obtained in about 89% yield and thereafter reacted with SM1 in analogy with the procedures described in Example 4f, and pimavanserin obtained in about 86% yield. Optionally I6 does not need to be isolated but directly used in the next step.

The obtained pimavanserin is thereafter converted into a hemi-tartrate salt for example as described in Example 7.

Example 5d: Preparation of Pimavanserin Via Using di-tert-butyl Dicarbonate (Boc$_2$O)

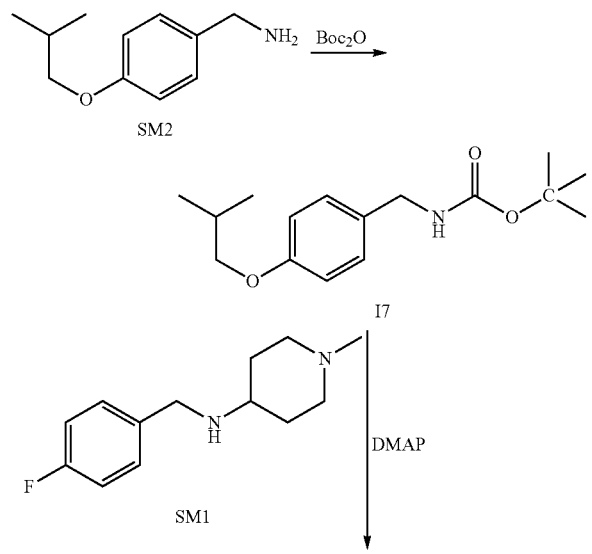

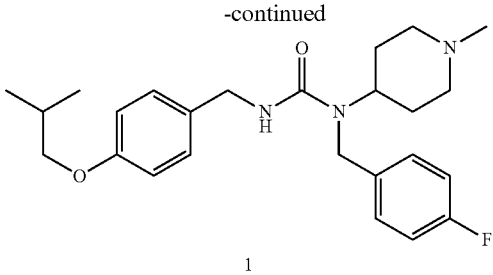

Di-tert-butoxycarbonyl anhydride (Boc$_2$O, 1.46 g, 6.69 mol, 1.2 eq) was dissolved in CH$_3$CN 10 ml and cooled to −10° C. Dimethylamino pyridine (DMAP, 0.14 g, 1.12 mol, 0.2 eq) was added and stirred for 10 min. After 10 min 4-isobutoxybenzyl amine (SM2) in 10 ml CH$_3$CN added rinsing it with CH$_3$CN (10 ml). The reaction was stirred for 15-30 min at −10° C. and diluted with chloroform (50 ml). The reaction mixture was washed with 5% HCl aqueous solution, dried over MgSO4 and evaporated to dryness to give crude product which was a mixture of the desired product 4-isobutoxybenzyl isocyanate (60-70%), 20% N-tert-butoxycarbonyl-4-isobutoxybenzyamine and other minor by products. The crude product was not purified. The analysis is based on the 1H NMR of the crude product mixture. $^1$H NMR (CDCl3): δ 1.0 (d, 6H); 2.0 (m, 1H); 3.7 (d, 2H); 4.3 (s, 2H), 6.9, d, 2H); 7.2 (d, 2H). Optionally 17 may be isolated. The mixture was stirred for about 1 h at room temperature (rt) followed by addition of a slight excess of SM1 in toluene and the catalyst added. The mixture stirred at 50° C. for about 15 h resulting in pimavanserin being obtained in a quantitative yield (using 1.8 eq CDI) upon aqueous work up.

Optionally SM2b may be treated with a suitable acid such as HCl, optionally isolated, and thereafter proceeding in accordance with the procedure described. In order to obtain pimavanserin an additional trituration of crude pimavanserin was conducted.

Example 6a: Preparation of Pimavanserin Via Urea Derivative

Reaction scheme

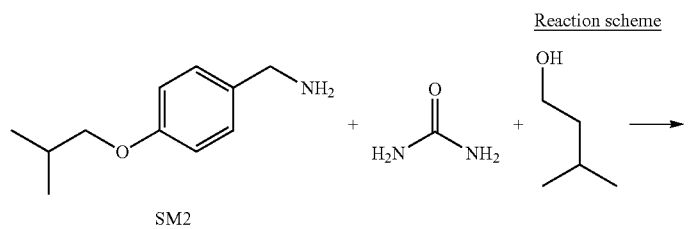

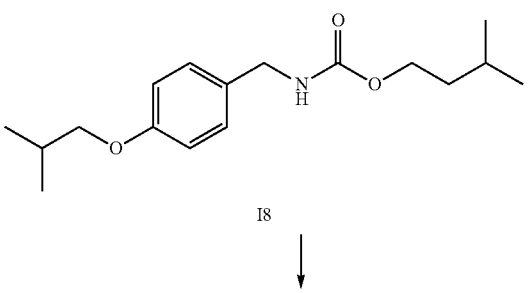

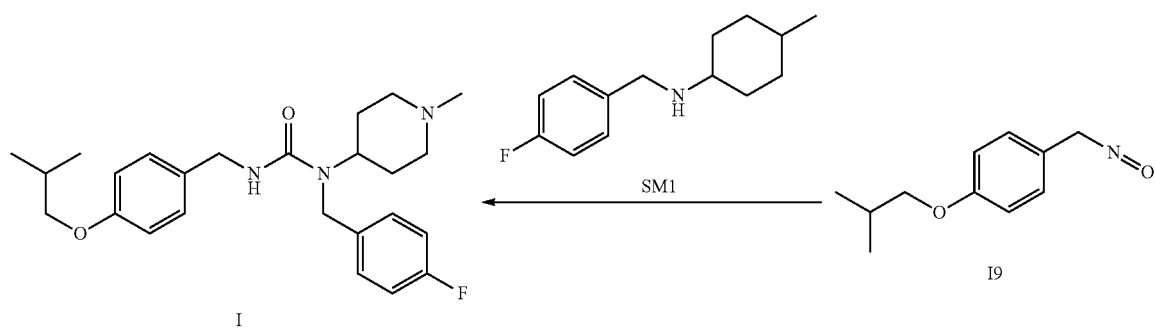

SM2 (1 eq) was treated by urea (2 eq) and 3-methylbutan-1-ol (2 eq) in toluene (10 ml) and heated to 160° C. for 4 h to give isopentyl (4-isobutoxybenzyl)carbamate (I8) (M+H=385) which was converted to the isocyanate I9 by distillation. I9 is then converted into pimavanserin according to already established methods, for example by reacting I9 with a slight excess of SM1 in THF followed by precipitation from EtOH to give pimavanserin.

Example 6b: Preparation of Pimavanserin Via Urea Derivative

Reaction scheme

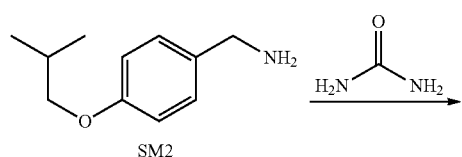

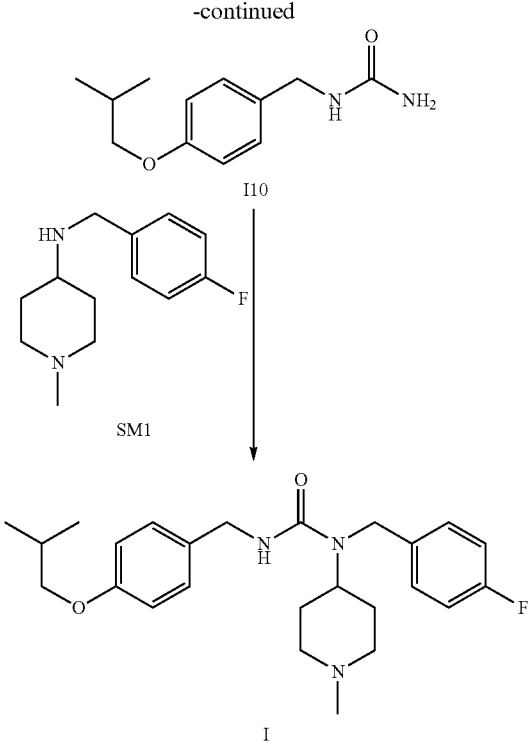

SM2 is brought into contact with a small excess of urea, and thereafter the mixture stirred at elevated temperature such as 150° C. in order to obtain I10. To I10 in toluene SM1 was added and the reaction proceeded as described above. The mixture was stirred until consumption of SM1 in order to give pimavanserin.

Example 6c: Preparation of Pimavanserin Via Second Urea Derivative
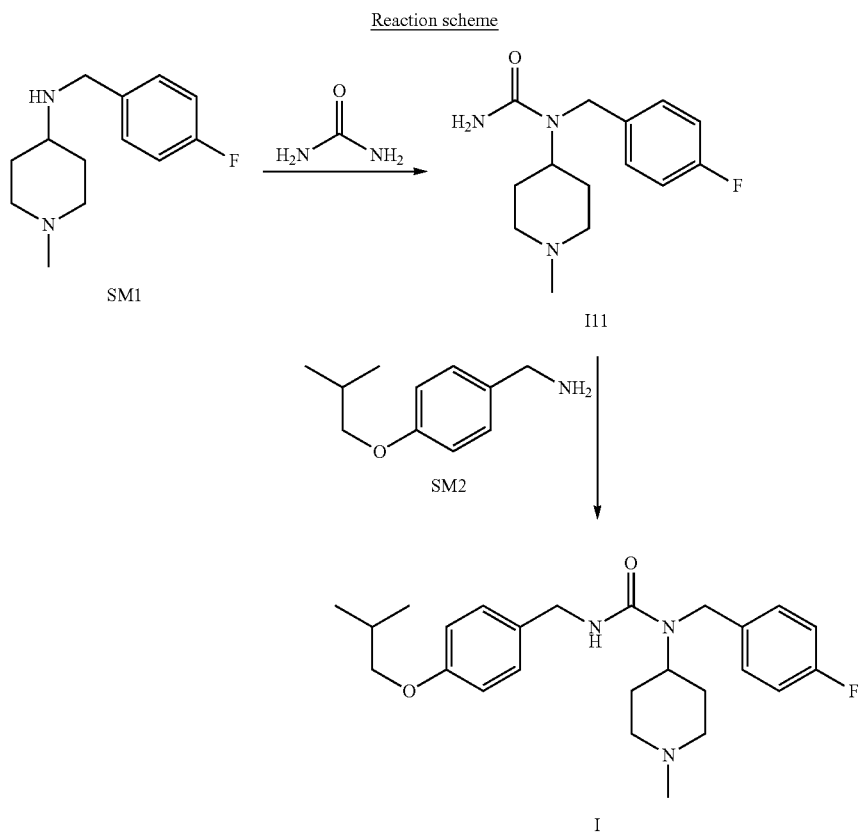
SM1 is brought into contact with a small excess of urea mixed at elevated temperature such as 150° C. to obtain I11 which thereafter is mixed with SM2. The mixture was stirred until consumption of SM2 in order to give pimavanserin.
Example 6d: Preparation of Pimavanserin Using a Carbamate Reagent
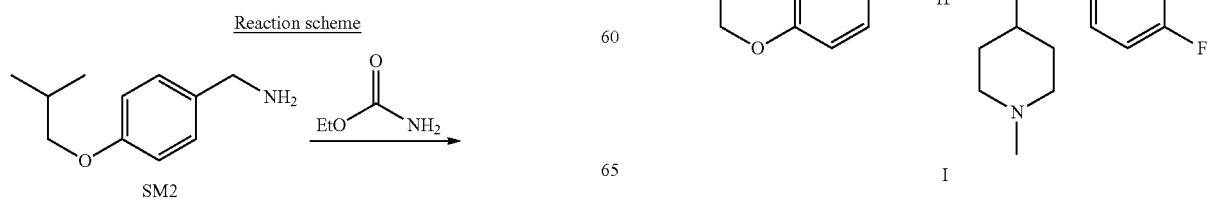

SM2 is brought into contact with a small excess of ethyl carbamate, and thereafter the mixture stirred followed by addition of SM1. The mixture was stirred until consumption of SM1 in order to give pimavanserin.

Optionally other alkyl carbamates such as methyl carbamate can be used.

Example 6e: Preparation of Pimavanserin Using a Reversed Carbamate Reagent

Reaction scheme

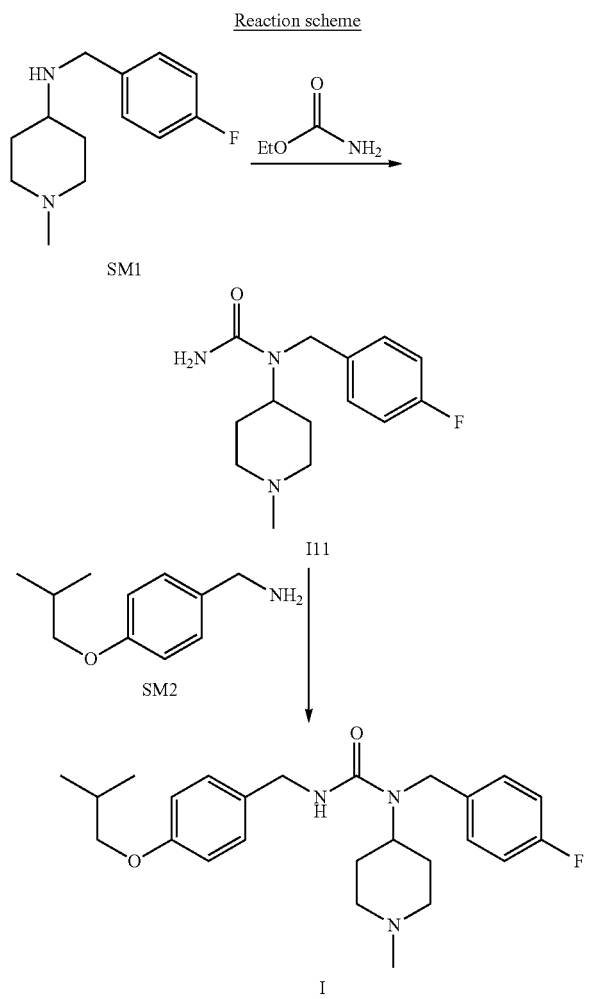

SM1 is brought into contact with a small excess of ethyl carbamate, and thereafter the mixture stirred followed by addition of SM2. The mixture was stirred until consumption of SM2 in order to give pimavanserin. Optionally other alkyl carbamates such as methyl carbamate can be used.

Optionally I11 (obtained for example as described above) may be reacted with 4-isobutoxybenzaldehyde (described herein) using titanium isopropoxide (slight excess) in THF and refluxing for 6 h to give pimavanserin followed by treatment by sodium borohydride; or I11 may be reacted with (4-isobutoxyphenyl)methanol (commercially available) using (Pentamethylcyclopentadienyl)iridium(III) chloride dimer as a catalyst, in tert-amyl alcohol and sodium hydroxide at 60° C. for 16 h to obtain pimavanserin.

NMR of I11 (400 MHz, DMSO-$d_6$) δ 7.30-7.21 (m, 2H), 7.15-7.04 (m, 2H), 5.97-5.92 (m, 2H), 4.37 (s, 2H), 3.82 (td, J=11.4, 5.3 Hz, 1H), 2.68 (dq, J=10.9, 2.6, 1.8 Hz, 2H), 2.08 (s, 3H), 1.87 (td, J=11.6, 2.6 Hz, 2H), 1.59-1.37 (m, 4H).

Example 7: Process Scale Preparation of Pimavanserin and Pimavanserin Tartrate

SM2b (350 g) dissolved in water (700 g) was added to toluene (1780 g), followed by potassium carbonate (200-220 g) in water (467 g). The vessel containing the potassium carbonate was washed with 87 g water and added to the mixture containing SM2b. Phenyl chloroformate (252-260 g) was added over 1.5 h while maintaining a temperature between 15-30° C. The vessel containing the phenyl chloroformate was washed with toluene (47 g) and added to the mixture containing SM2b followed by stirring at about 20-30° C. for 1-2 h. The mixture was heated to 50-60° C. and solvent was distilled off (about 940 g) from the organic layer. The mixture was heated to about 70° C. and heptane (1000-1200 ml) added at a rate maintaining the temperature at or above 65° C., and thereafter stirred at 70° C. for 1 h. Thereafter the mixture was cooled to ambient temperature and stirred for 12-18 h, and thereafter filtered. The product was washed, with heptane/ethyl acetate (9:1), and dried to give about 400 g of I1.1.

I1.1 (350 g), potassium carbonate (80.0-90 g) were suspended in toluene (about 1600-2000 g), and SM1 (e.g. prepared as outline in Example 1a or b) (272.9 g) was added and the vessel containing SM1 was washed with toluene (about 140 g), added to the mixture containing I1.1. The mixture was heated to about 60-70° C. for 4-8 h. Thereafter the mixture was cooled to about 50° C., and washed with 30% sodium hydroxide (195 g) in water (1376 g). The organic layer was washed with water (805 g) at a temperature of about 50° C. and thereafter solvent was distilled off (about 1200 g), followed by addition of ethyl acetate (483 g) and heptane (1931 g). The mixture was heated to about 60° C. for 1 h and allowed to cool to 20° C. at a rate of about 0.2° C./min, and thereafter stirred for 3-5 h followed by filtering and washing with 20 w % ethyl acetate in heptane (604 g). The obtained compound of Formula (I) (pimavanserin) was dried at about 50° C. for 12 h (<50 mbar).

The compound of Formula (I) can be converted into a hemi-tartrate salt. Examples of the salt formation are: suspending the compound of Formula (I) (400 g) in methyl ethyl ketone (MEK, 2368 g), heat to dissolve at about 50° C. and filter into a reactor through a 1 µm filter washing with MEK (95 g). (L)-tartaric acid (70.22 g), dissolved in MEK (758 g) and methanol (112 g), heated to about 50° C. and filtered through a 1 µm filter into a vessel. Seed crystals (15.7 g) of pimavanserin tartrate form C was added to the mixture and the (L)-tartaric acid solution added over approximately 2 h while a temperature of above about 45° C. was maintained. Solvent was distilled off, and MEK (804 g) added and additional solvent distilled off under vacuum at a temperature between 20 and 50° C. The mixture was heated to about 60-75° C. and maintained for 1-14 h and thereafter cooled to a temperature of about 5° C. over approximately 6 h, followed by stirring for about 2 h, and thereafter filter washed with MEK. The product was dried at about 50° C. to give a tartrate salt of the compound of Formula (I) as polymorphic Form C.

The formation of the hemi-tartrate salt of the compound of Formula (I), as well as polymorphic Form C, may be performed as an integrated process step, or as a separate subsequent process step. Hence Form C can be obtained in a direct formation from pimavanserin without the need for intermediate isolation.

Optionally the tartrate salt of the compounds of Formula (I) may be obtained by a preparing a solution of tartaric acid in ethanol by heating at about 40-50° C., and part of the solution added the compound of Formula I in ethanol (prepared according to any one of examples 1-6). The solution was seeded with pimavanserin tartrate, e.g. a mixture of polymorphic forms, and stirred the slurry for 30-60 min at 40-50° C. Thereafter the rest of the tartaric acid solution was added and the slurry stirred for additional 30 min. The reaction mixture was cooled to 0-10° C. over 5-6 h and stirred at this temperature for 1 h. The product was isolated by centrifugation and washed with cold ethanol. The crude product thus obtained was dried under vacuum at 45° C., sieved at 3 mm followed by another drying in order to obtain pimavanserin as a salt.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of preparing pimavanserin (N-(4-fluorophenylmethyl)-N-(1-methylpiperidin-4-yl)-N'-(4-(2-methylpropyloxy)phenylmethyl)carbamide) or a salt thereof, the method comprising:
    contacting i) isobutyl methanesulfonate or isobutyl p-toluenesulfonate with 4-hydroxybenzaldehyde, or ii) contacting isobutanol with 4-fluorobenzaldehyde, thereby producing (4-isobutoxyphenyl)methanamine;
    contacting (4-isobutoxyphenyl)methanamine with carbonyldiimidazole to produce the intermediate according to Formula (I6);

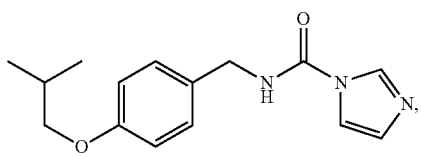

(I6)

contacting the intermediate according to Formula (I6) or a salt thereof with an intermediate according to Formula (B2),

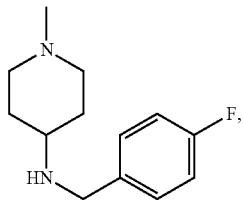

(B2)

or a salt thereof, to produce pimavanserin or a salt thereof.

2. The method according to claim 1, wherein the produced intermediate according to Formula (I6) is isolated prior to being contacted by the intermediate according to Formula (B2).

3. The method according to claim 1, wherein the (4-isobutoxyphenyl)methanamine is contacted by carbonyldiimidazole to produce the intermediate according to Formula (I6), which is subsequently contacted by the intermediate according to Formula (B2) in a telescoping synthesis.

4. The method according to claim 1, further comprising contacting the pimavanserin produced from the previous step with (L)-tartaric acid to produce a pimavanserin tartrate salt.

5. The method according to claim 4, wherein the pimavanserin tartrate salt is a hemi-tartrate salt.

6. The method according to claim 4, wherein the produced pimavanserin is contacted with (L)-tartaric acid in methyl ethyl ketone to produce a pimavanserin tartrate salt obtained as a polymorphic Form C characterized by having an endotherm with an onset of between 167 and 177° C. as obtained by differential scanning calorimetry (DSC).

7. The method according to claim 6, wherein the DSC shows no peak between 120 and 140° C.

8. The method according to claim 4, wherein the produced pimavanserin is isolated prior to being contacted with (L)-tartaric acid to produce the pimavanserin tartrate salt.

9. The method according to claim 4, wherein the produced pimavanserin is not isolated prior to being contacted with (L)-tartaric acid to produce the pimavanserin tartrate salt.

10. The method according to claim 1, wherein the intermediate according to Formula (I6) is contacted with the intermediate according to Formula (B2) in the presence of a base.

11. The method according to claim 10, wherein the base is selected from the group consisting of triethyl amine, diisopropyl amine, pyridine, alkali metal carbonates, sodium hydroxide, potassium hydroxide, sodium phosphate and potassium phosphate.

12. The method according to claim 11, wherein the base is sodium carbonate or potassium carbonate.

13. The method according to claim 11, wherein the base is potassium carbonate.

* * * * *